(12) United States Patent
Lira et al.

(10) Patent No.: US 9,814,632 B2
(45) Date of Patent: Nov. 14, 2017

(54) BODY ADHERING ABSORBENT ARTICLE

(71) Applicant: Kimberly-Clark Worldwide, Inc., Neenah, WI (US)

(72) Inventors: Carmen Lira, Downers Grove, IL (US); Candace Dyan Krautkramer, Neenah, WI (US); Melissa Jean Dennis, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 160 days.

(21) Appl. No.: 14/163,260

(22) Filed: Jan. 24, 2014

(65) Prior Publication Data
US 2014/0142530 A1      May 22, 2014

Related U.S. Application Data

(60) Division of application No. 12/364,406, filed on Feb. 2, 2009, now Pat. No. 8,672,911, which is a
(Continued)

(51) Int. Cl.
*A61F 13/56*   (2006.01)
*A61F 13/82*   (2006.01)
(Continued)

(52) U.S. Cl.
CPC .......... *A61F 13/472* (2013.01); *A61F 13/551* (2013.01); *A61F 13/56* (2013.01); *A61F 13/82* (2013.01)

(58) Field of Classification Search
CPC .................. A61F 13/56; A61F 13/82; A61F 2013/15569; A61F 2013/16;
(Continued)

(56) References Cited

U.S. PATENT DOCUMENTS 2,842,897 A    7/1958  Finn
3,288,346 A    11/1966 Peppler
(Continued)

FOREIGN PATENT DOCUMENTS

DE    69232589    12/2002
EP    0353972     2/1990
(Continued)

OTHER PUBLICATIONS

American Society for Testing Materials (ASTM) Designation: D1300-53 T, "Tentative Specifications and Methods of Test for Laminated Terhmosetting Decorativ esheets," pp. 148-166, issued 1953.
(Continued)

*Primary Examiner* — Peter S Vasat
(74) *Attorney, Agent, or Firm* — Armstrong Teasdale LLP

(57) ABSTRACT

A feminine care absorbent article includes an absorbent structure configured for disposition adjacent a female wearer's vaginal region to absorb bodily fluids discharged by the wearer. A shell is provided for supporting the absorbent structure at the vaginal region. The shell has a body-facing surface and a garment-facing surface. The body-facing surface has an adhesive thereon for adhering the shell directly to the wearer's body. The adhesive has a non-uniform adhesive pattern.

20 Claims, 42 Drawing Sheets

Related U.S. Application Data continuation-in-part of application No. 12/182,937, filed on Jul. 30, 2008, now Pat. No. 8,197,456, which is a continuation-in-part of application No. 11/890,093, filed on Aug. 3, 2007, now Pat. No. 8,251,969, and a continuation-in-part of application No. 12/005,793, filed on Dec. 28, 2007, now Pat. No. 7,947,027.

(51) Int. Cl.
*A61F 13/472* (2006.01)
*A61F 13/551* (2006.01)

(58) Field of Classification Search
CPC ............. A61F 13/5605; A61F 5/443; A61F 2013/00804; A61F 2013/00421; A61F 13/025; B32B 37/1292
USPC ............. 604/358, 387; 427/208.4, 208.6; 442/151
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,598,123 A | 8/1971 | Zaffaroni | |
| 3,692,618 A | 9/1972 | Dorschner et al. | |
| 3,731,683 A | 5/1973 | Zaffaroni | |
| 3,802,817 A | 4/1974 | Matsuki et al. | |
| 3,811,438 A * | 5/1974 | Economou | 602/55 |
| 3,849,241 A | 11/1974 | Butin et al. | |
| 3,885,559 A * | 5/1975 | Economou | 602/55 |
| 3,963,029 A | 6/1976 | Brooks | |
| 3,972,328 A | 8/1976 | Chen | |
| 3,998,215 A | 12/1976 | Anderson et al. | |
| 4,072,151 A | 2/1978 | Levine | |
| 4,340,563 A | 7/1982 | Appel et al. | |
| 4,488,928 A | 12/1984 | Ali Khan et al. | |
| 4,505,976 A | 3/1985 | Doehnert et al. | |
| 4,631,062 A | 12/1986 | Lassen et al. | |
| 4,673,403 A | 6/1987 | Lassen et al. | |
| 4,743,245 A | 5/1988 | Lassen et al. | |
| 4,758,241 A | 7/1988 | Papajohn | |
| 4,781,712 A | 11/1988 | Barabino et al. | |
| 4,798,603 A | 1/1989 | Meyer et al. | |
| 4,804,380 A | 2/1989 | Lassen et al. | |
| 4,846,824 A | 7/1989 | Lassen et al. | |
| 4,909,244 A | 3/1990 | Quarfoot et al. | |
| 4,977,892 A | 12/1990 | Ewall | |
| 5,051,259 A | 9/1991 | Olsen et al. | |
| 5,114,419 A | 5/1992 | Daniel et al. | |
| 5,133,705 A | 7/1992 | Nakanishi et al. | |
| 5,147,938 A | 9/1992 | Kuller | |
| 5,160,328 A | 11/1992 | Cartmell et al. | |
| 5,194,299 A | 3/1993 | Fry | |
| 5,194,550 A | 3/1993 | Rance et al. | |
| 5,221,275 A | 6/1993 | Van Iten | |
| 5,277,954 A | 1/1994 | Carpenter et al. | |
| 5,369,155 A | 11/1994 | Asmus | |
| 5,382,400 A | 1/1995 | Pike et al. | |
| 5,387,208 A | 2/1995 | Ashton et al. | |
| 5,419,956 A | 5/1995 | Roe | |
| 5,445,627 A | 8/1995 | Mizutani et al. | |
| 5,554,381 A | 9/1996 | Roos et al. | |
| H1602 H | 10/1996 | Brock | |
| 5,591,146 A | 1/1997 | Hasse | |
| 5,599,335 A | 2/1997 | Goldman et al. | |
| 5,611,790 A | 3/1997 | Osborn, III et al. | |
| 5,614,310 A | 3/1997 | Delgado et al. | |
| 5,618,281 A | 4/1997 | Betrabet et al. | |
| 5,618,282 A | 4/1997 | Schlangen | |
| 5,632,736 A | 5/1997 | Block | |
| 5,658,270 A | 8/1997 | Lichstein | |
| 5,662,633 A | 9/1997 | Doak et al. | |
| 5,669,894 A | 9/1997 | Goldman et al. | |
| 5,706,950 A | 1/1998 | Houghton et al. | |
| 5,714,225 A | 2/1998 | Hansen et al. | |
| 5,716,621 A | 2/1998 | Bello et al. | |
| 5,759,560 A | 6/1998 | Dillon | |
| 5,769,837 A | 6/1998 | Parr | |
| 5,800,417 A | 9/1998 | Goerg-Wood et al. | |
| 5,807,367 A | 9/1998 | Dilnik et al. | |
| 5,811,116 A | 9/1998 | Gilman et al. | |
| 5,830,202 A | 11/1998 | Bogdanski et al. | |
| 5,885,265 A | 3/1999 | Osborn, III et al. | |
| 5,897,546 A | 4/1999 | Kido et al. | |
| 5,910,125 A | 6/1999 | Cummings et al. | |
| 5,994,613 A | 11/1999 | Cummings et al. | |
| 6,045,900 A | 4/2000 | Haffner et al. | |
| 6,155,265 A | 12/2000 | Hammerslag | |
| 6,156,818 A | 12/2000 | Corzani et al. | |
| 6,177,482 B1 | 1/2001 | Cinelli et al. | |
| 6,187,989 B1 | 2/2001 | Corzani et al. | |
| 6,191,189 B1 | 2/2001 | Cinelli et al. | |
| 6,211,263 B1 | 4/2001 | Cinelli et al. | |
| 6,213,993 B1 | 4/2001 | Zacharias et al. | |
| 6,255,552 B1 | 7/2001 | Cummings et al. | |
| 6,316,524 B1 | 11/2001 | Corzani et al. | |
| 6,336,935 B1 | 1/2002 | Davis et al. | |
| 6,362,389 B1 | 3/2002 | MDowall et al. | |
| 6,365,645 B1 | 4/2002 | Cinelli et al. | |
| 6,369,126 B1 | 4/2002 | Cinelli et al. | |
| 6,383,630 B1 * | 5/2002 | Jauchen | A61F 13/02 427/208.2 |
| 6,386,203 B1 | 5/2002 | Hammerslag | |
| 6,479,724 B1 | 11/2002 | Areskoug et al. | |
| 6,491,953 B1 | 12/2002 | Sojka et al. | |
| 6,495,229 B1 | 12/2002 | Carte et al. | |
| 6,565,961 B2 | 5/2003 | Koslow | |
| 6,566,575 B1 | 5/2003 | Stickels et al. | |
| 6,582,411 B1 | 6/2003 | Carstens et al. | |
| 6,613,955 B1 * | 9/2003 | Lindsay | A61F 13/4704 604/378 |
| 6,616,643 B1 | 9/2003 | Costa | |
| 6,617,490 B1 | 9/2003 | Chen et al. | |
| 6,620,143 B1 | 9/2003 | Zacharias et al. | |
| 6,632,210 B1 | 10/2003 | Glasgow et al. | |
| 6,641,569 B1 | 11/2003 | Coles et al. | |
| 6,657,009 B2 | 12/2003 | Zhou | |
| 6,670,402 B1 | 12/2003 | Lee et al. | |
| 6,683,143 B1 | 1/2004 | Mumick et al. | |
| 6,733,483 B2 | 5/2004 | Raufman et al. | |
| 6,756,520 B1 | 6/2004 | Krzysik et al. | |
| 6,803,420 B2 | 10/2004 | Cleary et al. | |
| 6,997,915 B2 | 2/2006 | Gell et al. | |
| 7,033,342 B2 | 4/2006 | Mizutani et al. | |
| 7,045,559 B2 | 5/2006 | Yahiaoui et al. | |
| 7,053,131 B2 | 5/2006 | Ko et al. | |
| 7,063,859 B1 | 6/2006 | Kanios et al. | |
| 7,122,022 B2 | 10/2006 | Drevik | |
| 7,125,401 B2 | 10/2006 | Yoshimasa | |
| 7,198,689 B2 | 4/2007 | Van Gompel et al. | |
| 7,217,259 B2 | 5/2007 | McDaniel | |
| 7,265,158 B2 | 9/2007 | Risen, Jr. et al. | |
| 7,358,282 B2 | 4/2008 | Krueger et al. | |
| 7,378,450 B2 | 5/2008 | Erkey et al. | |
| 7,918,837 B2 | 4/2011 | Rosenfeld | |
| 2001/0039407 A1 | 11/2001 | Widlund | |
| 2002/0013565 A1* | 1/2002 | Cinelli et al. | 604/385.03 |
| 2002/0013566 A1 | 1/2002 | Chappell et al. | |
| 2002/0037977 A1 | 3/2002 | Feldstein et al. | |
| 2002/0193766 A1 | 12/2002 | Gell et al. | |
| 2003/0004484 A1 | 1/2003 | Hammons et al. | |
| 2003/0044380 A1 | 3/2003 | Zhu et al. | |
| 2003/0065302 A1 | 4/2003 | Kuroda et al. | |
| 2003/0065304 A1 | 4/2003 | Bernhard et al. | |
| 2003/0078554 A1* | 4/2003 | Drevik | A61F 13/47254 604/385.03 |
| 2003/0106825 A1 | 6/2003 | Molina et al. | |
| 2003/0170308 A1 | 9/2003 | Cleary et al. | |

(56) References Cited

U.S. PATENT DOCUMENTS

| | | |
|---|---|---|
| 2003/0203011 A1 | 10/2003 | Abuelyaman et al. |
| 2003/0208112 A1 | 11/2003 | Schmidt et al. |
| 2003/0212416 A1 | 11/2003 | Cinelli et al. |
| 2004/0005830 A1 | 1/2004 | Anderson et al. |
| 2004/0059310 A1 | 3/2004 | Gagliardi et al. |
| 2004/0115251 A1 | 6/2004 | Goldman et al. |
| 2004/0116883 A1 | 6/2004 | Krautkramer et al. |
| 2004/0122385 A1 | 6/2004 | Morman et al. |
| 2004/0133143 A1 | 7/2004 | Burton et al. |
| 2004/0151930 A1 | 8/2004 | Rouns et al. |
| 2004/0158221 A1* | 8/2004 | Mizutani ........... A61F 13/47209 604/385.17 |
| 2004/0167488 A1 | 8/2004 | Bellucci et al. |
| 2004/0167491 A1 | 8/2004 | Mizutani |
| 2004/0209075 A1 | 10/2004 | Maloney |
| 2005/0010185 A1* | 1/2005 | Mizutani ........... A61F 13/47209 604/385.03 |
| 2005/0014901 A1 | 1/2005 | Osae et al. |
| 2005/0059918 A1 | 3/2005 | Sigurjonsson et al. |
| 2005/0124960 A1 | 6/2005 | Ruman |
| 2005/0136023 A1 | 6/2005 | Yahiaoui et al. |
| 2005/0136077 A1 | 6/2005 | Yahiaoui et al. |
| 2005/0137549 A1 | 6/2005 | Lindsay et al. |
| 2005/0137561 A1 | 6/2005 | Mizutani et al. |
| 2005/0148984 A1 | 7/2005 | Lindsay et al. |
| 2005/0182378 A1 | 8/2005 | Bonelli et al. |
| 2005/0226917 A1 | 10/2005 | Burton |
| 2005/0233149 A1 | 10/2005 | Ansell |
| 2005/0261652 A1 | 11/2005 | Digiacomantonio et al. |
| 2006/0058760 A1 | 3/2006 | Rosenfeld et al. |
| 2006/0058764 A1 | 3/2006 | Bohlen et al. |
| 2006/0063322 A1 | 3/2006 | Hsu et al. |
| 2006/0129114 A1 | 6/2006 | Mason, Jr. et al. |
| 2006/0142722 A1 | 6/2006 | Koenig et al. |
| 2006/0148352 A1 | 7/2006 | Munro et al. |
| 2006/0148917 A1 | 7/2006 | Radwanski et al. |
| 2006/0161125 A1 | 7/2006 | Bohlen et al. |
| 2006/0188940 A1 | 8/2006 | Cima et al. |
| 2006/0195053 A1 | 8/2006 | Oelund et al. |
| 2006/0205835 A1 | 9/2006 | Husemann et al. |
| 2006/0206077 A1 | 9/2006 | Warren et al. |
| 2006/0216523 A1 | 9/2006 | Takaki |
| 2006/0224133 A1 | 10/2006 | Gannon et al. |
| 2006/0224134 A1 | 10/2006 | Luizzi et al. |
| 2006/0240087 A1 | 10/2006 | Houze et al. |
| 2006/0258788 A1 | 11/2006 | Coggins et al. |
| 2006/0264884 A1 | 11/2006 | Carstens |
| 2007/0031463 A1 | 2/2007 | Fotinos et al. |
| 2007/0100313 A1 | 5/2007 | Luizzi |
| 2007/0124850 A1 | 6/2007 | Buettner |
| 2007/0250028 A1 | 10/2007 | Woltman et al. |
| 2007/0275068 A1 | 11/2007 | Martens et al. |
| 2007/0287973 A1 | 12/2007 | Cohen et al. |
| 2008/0015535 A1 | 1/2008 | Gannon et al. |
| 2008/0057811 A1 | 3/2008 | Yahiaoui et al. |
| 2008/0071237 A1 | 3/2008 | Chen et al. |
| 2008/0147035 A1 | 6/2008 | Snell |
| 2008/0161492 A1 | 7/2008 | Cleary et al. |
| 2008/0207779 A1 | 8/2008 | Yahiaoui et al. |
| 2008/0234647 A1 | 9/2008 | Arterburn |
| 2009/0062761 A1 | 3/2009 | Goereg-Wood et al. |
| 2009/0071862 A2 | 3/2009 | Snell |
| 2009/0118691 A1* | 5/2009 | Rosenfeld ......... A61F 13/47236 604/385.03 |
| 2010/0121304 A1 | 5/2010 | Zhou et al. |
| 2011/0092945 A1 | 4/2011 | Carstens |
| 2011/0135726 A1 | 6/2011 | Munro et al. |

FOREIGN PATENT DOCUMENTS

| | | |
|---|---|---|
| EP | 0638303 | 11/1997 |
| EP | 0850628 | 7/1998 |
| EP | 909662 | 4/1999 |
| EP | 0609236 | 5/2002 |
| EP | 1407737 A1 | 4/2004 |
| EP | 1468661 | 10/2004 |
| EP | 1407743 | 1/2010 |
| GB | 2284767 | 6/1995 |
| JP | 04279159 | 10/1992 |
| JP | 9117473 | 5/1997 |
| KR | 10-2001-0022000 | 3/2001 |
| KR | 10-0563880 | 3/2006 |
| RU | 2276998 | 5/2006 |
| RU | 2277891 | 6/2006 |
| RU | 2286801 | 11/2006 |
| WO | 9307841 | 4/1993 |
| WO | 9516424 | 6/1995 |
| WO | 9827910 | 7/1998 |
| WO | 9827912 | 7/1998 |
| WO | 9827913 | 7/1998 |
| WO | 9827915 | 7/1998 |
| WO | 9827916 | 7/1998 |
| WO | 9827917 | 7/1998 |
| WO | 9827918 | 7/1998 |
| WO | 9828015 | 7/1998 |
| WO | 9828017 | 7/1998 |
| WO | 9828019 | 7/1998 |
| WO | 9828022 | 7/1998 |
| WO | 9828023 | 7/1998 |
| WO | 9847454 | 10/1998 |
| WO | 9855065 | 12/1998 |
| WO | 9857609 | 12/1998 |
| WO | 9901094 | 1/1999 |
| WO | 9901095 | 1/1999 |
| WO | 9930659 | 6/1999 |
| WO | 0000235 | 1/2000 |
| WO | 0287642 | 5/2002 |
| WO | 03062343 | 7/2003 |
| WO | 2004093766 | 11/2004 |
| WO | 2006028612 | 3/2006 |
| WO | 2010077306 | 7/2010 |

OTHER PUBLICATIONS

Australian Patent Examination Report for Patent Application No. 2008285169, dated Nov. 22, 2012; 4 pages.
Berner et al., Photo Initiators—An Overview, J. Radiation Curing (Apr. 1979), pp. 29.
Chinese First Office Action for Application No. 201080006001.7, dated Jan. 31, 2013; 12 pages.
Chinese Second Office Action for Application No. 200980138546.0, dated Sep. 13, 2013; 15 pages.
Final Rule for U.S. Antiperspirant Drug Products for Over-the-Counter Human Use; Final Monograph, vol. 68, No. 110 Fed. Reg. 34273-34293 (Jun. 9, 2003).
International Search Report for PCT/IB2009/053073 dated Mar. 26, 2010; 13 pages.
International Search Report for PCT/IB2009/053074 dated Mar. 26, 2010; 11 pages.
International Search Report for PCT/IB2009/054647 mailed May 31, 2010; 12 pages.
International Search Report for PCT/IB2010/050407 dated Oct. 21, 2010; 10 pages.
International Search Report for PCT/IB2010/050408 dated Nov. 1, 2010; 10 pages.
Jillian Lloyd, Naomi Crouch, Catherine Minto, Lih-Mei Liao, Sarah Creighton, Female Genital Appearance: 'Normality' Unfolds, BJOG: An International Journal of Obstetrics and Gynecology, May 2005, vol. 112, pp. 643-646, Blackwell Publishing.
Mahdavi et al., A Biodegradable and Biocompatible Gecko-inspired Tissue Adhesive, PNAS, vol. 105: 7, pp. 2307-2312.
Matsumoto; "Characteristic polymerization behaviour of microgel-like poly(allyl methacrylate) microspheres"; Macromolecular Symposia; 2002; pp. 141-152; vol. 179; No. 1.
Non-Final Office Action regarding U.S. Appl. No. 12/267,806, dated May 28, 2013.
Supplemental European Search Report from EP Application No. 08789525.6 dated Sep. 21, 2012.

(56) References Cited

OTHER PUBLICATIONS

Translation of Russian Patent Examination Report for Patent Application No. 2011123315, dated Feb. 25, 2013; 3 pages.
Second Office Action from Russian Patent Application No. 2011136300, dated Jul. 10, 2014; 4 pages.
Non-final Office action issued for U.S. Appl. No. 12/267,806 (dated Oct. 3, 2014).
21 C.F.R. 350.3 (2008).
21 C.F.R. 350.10 (2008).
International Search Report for PCT/IB2010/050416 dated Nov. 1, 2010; 8 pages.
Non-Final Office Action received in U.S. Appl. No. 12/364,421 dated Sep. 6, 2011.
Office Action received in EP Application Serial No. 04750195.2, dated Jul. 6, 2010.
Product specification of Reemay® Spunbonded Polyester Nonwovens, Style# 2214, found at http://filters.kavonfilter.com/item/filter-paper/reemay-spunbonded-polyester-nonwovens/item-1117? (1 page).
Second Examination Result received in Columbian Patent Application No. 11-95035, dated Oct. 18, 2013.
Second Office Action from CN Application No. 200980138546.0, dated Sep. 13, 2013; 11 pages.
Supplemental European Search Report for Patent Application No. 09824477.5-1303, dated Jun. 7, 2013; 4 pages.
Spindler, et al., "Poly-Pore, a microparticle delivery system: this material offers sustained release, protects sensitive materials and provides multifunctional benefits in personal care formulations," Household & Personal Products Industry, May 1, 2002.
Office action issued in Korean Patent Application No. 10-2011-7018003 (dated May 2016), 4 pages.
First Office Action from Russian Patent Application No. 2011136300, dated Jan. 31, 2014; 3 pages.

\* cited by examiner

BODY ADHERING ABSORBENT ARTICLE

CROSS REFERENCE TO RELATED APPLICATIONS

This application is a divisional of U.S. patent application Ser. No. 12/364,406 filed Feb. 2, 2009, which is a continuation-in-part of U.S. patent application Ser. No. 12/182,937 filed Jul. 30, 2008 (now U.S. Pat. No. 8,197,456), which is a continuation-in-part application of U.S. patent application Ser. No. 11/890,093 filed Aug. 3, 2007 (now U.S. Pat. No. 8,251,969), and U.S. patent application Ser. No. 12/005,793 filed Dec. 28, 2007 (now U.S. Pat. No. 7,947,027). Each of these applications and patents is hereby incorporated by reference in its entirety.

BACKGROUND

The present invention relates generally to an absorbent article for absorbing bodily fluids.

Absorbent personal care articles intended to absorb discharged bodily fluids are well known in the art. Such absorbent articles generally comprise a fibrous mass or other absorbent core which can absorb and hold body fluids. Similarly, it is well known that feminine care articles have been employed to absorb and hold liquids, such as urine and/or menses. A typical structure of an absorbent article includes a fluid impermeable back sheet, a fluid permeable top sheet and an absorbent core positioned between the back sheet and the top sheet. Prior absorbent articles have also included various other features to improve fluid handling, such as intake layers, distribution layers, retention layers and the like. In these absorbent personal care articles, the top sheet is the body-facing side of the absorbent article and the back sheet is the garment-facing side of the absorbent article.

Generally, the absorbent articles are held in place during use by using the wearer's waist and elastic materials in the waist portion of the absorbent product in place during use, in the case of pant-like garments, such as diapers and training pants, or by attaching the absorbent article to the underwear or undergarment of a wearer, in the case of pads or liners. Current methods of attaching the absorbent article to the underwear or undergarment of a wearer include placing an adhesive on the garment-facing side of the back sheet, having optional flaps (wings) that extend from the longitudinal sides of the absorbent article which wrap around the crotch portion of the underwear or undergarment of the wearer and a combination of the adhesive and the flaps.

It has also been suggested to use an adhesive to adhere the absorbent article to the skin of the wearer. However, the design of these absorbent articles was essentially the same as the absorbent articles which were attached to the underwear or undergarment of the wearer. That is, the adhesive is applied to the body-facing surface of the top sheet. Alternatively, in another design, a portion of the back sheet was wrapped around and over the top sheet. This portion of the back sheet which is wrapped around and over the top sheet becomes a body facing surface. An adhesive is applied to the portion of the back sheet which is wrapped over the top sheet. While these designs were effective for adhering the absorbent article to the skin of a wearer, these absorbent articles were not comfortable for wearers to wear, since the shape and size of the absorbent articles were the same as those absorbent articles which were attached to the undergarment or underwear of the wearer.

Similarly, absorbent articles that are attached to the underwear or undergarment of a wearer can also be uncomfortable for the wearer. This is because during normal movement of the body, portions of the body place opposed forces on the undergarment, which may cause the undergarment to be bunched or twisted. When this occurs, any absorbent article attached to the underwear or undergarment may also become bunched or twisted, causing discomfort to the wearer of the absorbent article. For example, the presence and absence of pressure from the absorbent article on the inner thighs as the wearer moves, which is often described by wearers as feeling "like a diaper", is one source which compromises comfort for wearers of conventional absorbent articles, including liners, ultra-thin absorbent pads and maxi pads. In addition, the movement of the wearer or deformation of the underwear while being worn may also cause the absorbent article to have a poor fit against the body of the wearer, which could result in leaks from the absorbent article.

Another disadvantage of conventional absorbent articles is that the silhouette or outline of the absorbent article may be visible to others through the clothing of the wearer. Even currently available ultra-thin absorbent articles may be visible through tight fitting outer clothing of a wearer. Therefore, conventional absorbent personal care articles do not always provide discretion for wearers.

There is a need in the art to provide wearers of absorbent articles with a discrete absorbent product, which is as easy to use as a conventional pad and is comfortable to wear and will effectively prevent or reduce premature leakage from the absorbent article.

SUMMARY

In one aspect, a feminine care absorbent article generally comprises an absorbent structure configured for disposition adjacent a female wearer's vaginal region to absorb bodily fluids discharged by the wearer. A shell is provided for supporting the absorbent structure at the vaginal region. The shell has a body-facing surface and a garment-facing surface. The body-facing surface has an adhesive thereon for adhering the shell directly to the wearer's body. The adhesive has a non-uniform adhesive pattern.

In another aspect, a feminine care absorbent article generally comprises an absorbent structure configured for disposition adjacent a female wearer's vaginal region to absorb bodily fluids discharged by the wearer. A shell is provided for supporting the absorbent structure at the vaginal region. The shell has a body-facing surface and a garment-facing surface. The body-facing surface has an adhesive thereon for adhering the shell directly to the wearer's body. The adhesive has a pattern and the body-facing surface has a visual cue associated with the adhesive for conveying the presence of the adhesive to the wearer.

In still another aspect, a feminine care absorbent article generally comprises an absorbent structure configured for disposition adjacent a female wearer's vaginal region to absorb bodily fluids discharged by the wearer. A breathable shell is provided for supporting the absorbent structure at the vaginal region. The shell has a body-facing surface and a garment-facing surface. The body-facing surface has an adhesive thereon for adhering the shell directly to the wearer's body. At least a portion of the body-facing surface is free from adhesive for maintaining at least some of the breathability of the shell.

In yet a further aspect, a feminine care absorbent article generally comprises an absorbent structure configured for disposition adjacent a female wearer's vaginal region to absorb bodily fluids discharged by the wearer. A shell is provided for supporting the absorbent structure at the vaginal region. The shell has a body-facing surface and a garment-facing surface. The body-facing surface has an adhesive thereon for adhering the shell directly to the wearer's body. The adhesive is applied to a first area of the body-facing surface to provide a first adhesive strength and the adhesive is applied to a second area of the body-facing surface to provide a second adhesive strength that is less than the first adhesive strength at the first area.

In still another aspect, a feminine care absorbent article generally comprises an absorbent structure configured for disposition adjacent a female wearer's vaginal region to absorb bodily fluids discharged by the wearer. A shell is provided for supporting the absorbent structure at the vaginal region. The shell has a body-facing surface and a garment-facing surface. The body-facing surface has a first region and a second region. The first region has an adhesive with a first formulation and the second region has an adhesive with a second formulation that is different than the first formulation.

DEFINITIONS

Figure 1:
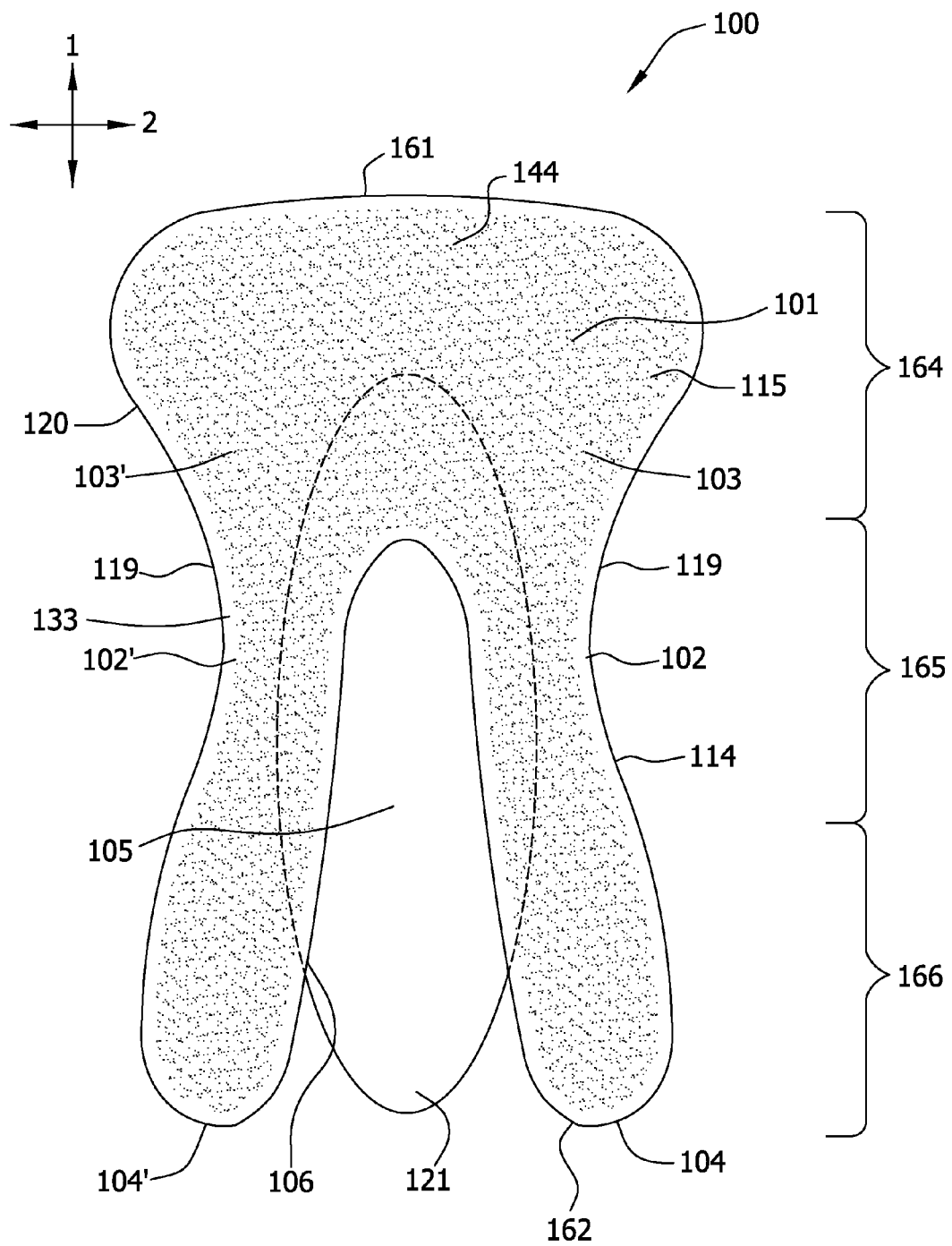
FIG. 1 shows a top view of an embodiment of an absorbent article of the present invention.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

It should be understood that the term "absorbent product" or "absorbent article", as used herein, refers to any article used to control bodily fluids that are configured to absorb and retain bodily exudates, including urine, blood, menses, and other bodily discharges, such as sweat and vaginal secretions resulting from sexual activity and the like. In addition, the term is intended to include odor absorbing articles.

As used herein, the term "polymer" generally includes, but is not limited to, homopolymers, copolymers, such as, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, "body-facing surface" means that surface of the absorbent article which is intended to be disposed toward or placed adjacent to the body of the wearer during ordinary use. The "garment-facing surface" is on the opposite side of the absorbent article from the body-facing surface. The garment-facing surface is an outward surface of the absorbent article and is intended to be disposed to face away from the wearer's body during ordinary use. The garment-facing surface is generally arranged to face toward or placed adjacent to the wearer's undergarments when the absorbent article is worn.

As used herein, the term "connected" is intended to mean directly connected and indirectly connected. By directly connected, it is intended that the connected elements are in contact with one another or affixed to one another. By indirectly connected, it is intended that one or more intervening or intermediate elements are between the two elements which are secured or "connected" together. The intervening elements may be affixed.

As used herein, the term "absorbent structure" is intended to mean a configuration of an absorbent material which allows bodily fluids to be absorbed by the absorbent material.

DETAILED DESCRIPTION

The absorbent product of the present invention provides an absorbent article which is designed to adhere to the body of a wearer in the area of the body of the wearer which may need bodily fluids absorbed. In one particular use of the absorbent article, the absorbent article is attached to the body of a female wearer to or around the vulva region of the body. By "to or around the vulva region", it is meant adjacent regions of the body of a female including the pubic region and the perinea region. When applied to or around the vulva region of the female body, the absorbent article may be used as a panty-liner, sanitary napkin or incontinence article. In addition, the absorbent article may be worn as an underwear substitute since the absorbent article of the present invention does not need underwear to hold the absorbent article in place. As an underwear substitute, the absorbent article provides protection to the vulva area by creating a barrier between the outer clothing and the vulva of a wearer. When worn as an underwear substitute, the absorbent article serves to protect the outer clothing of the wearer from bodily discharges from the vulva region of the wearer's body. In addition, when the absorbent article is worn as an underwear substitute, the absorbent article also serves to protect the sensitive skin and body features of the vulva region from roughness of the outer clothing, thereby preventing or alleviating irritation to the sensitive skin and body features of the vulva region.

Figure 2:
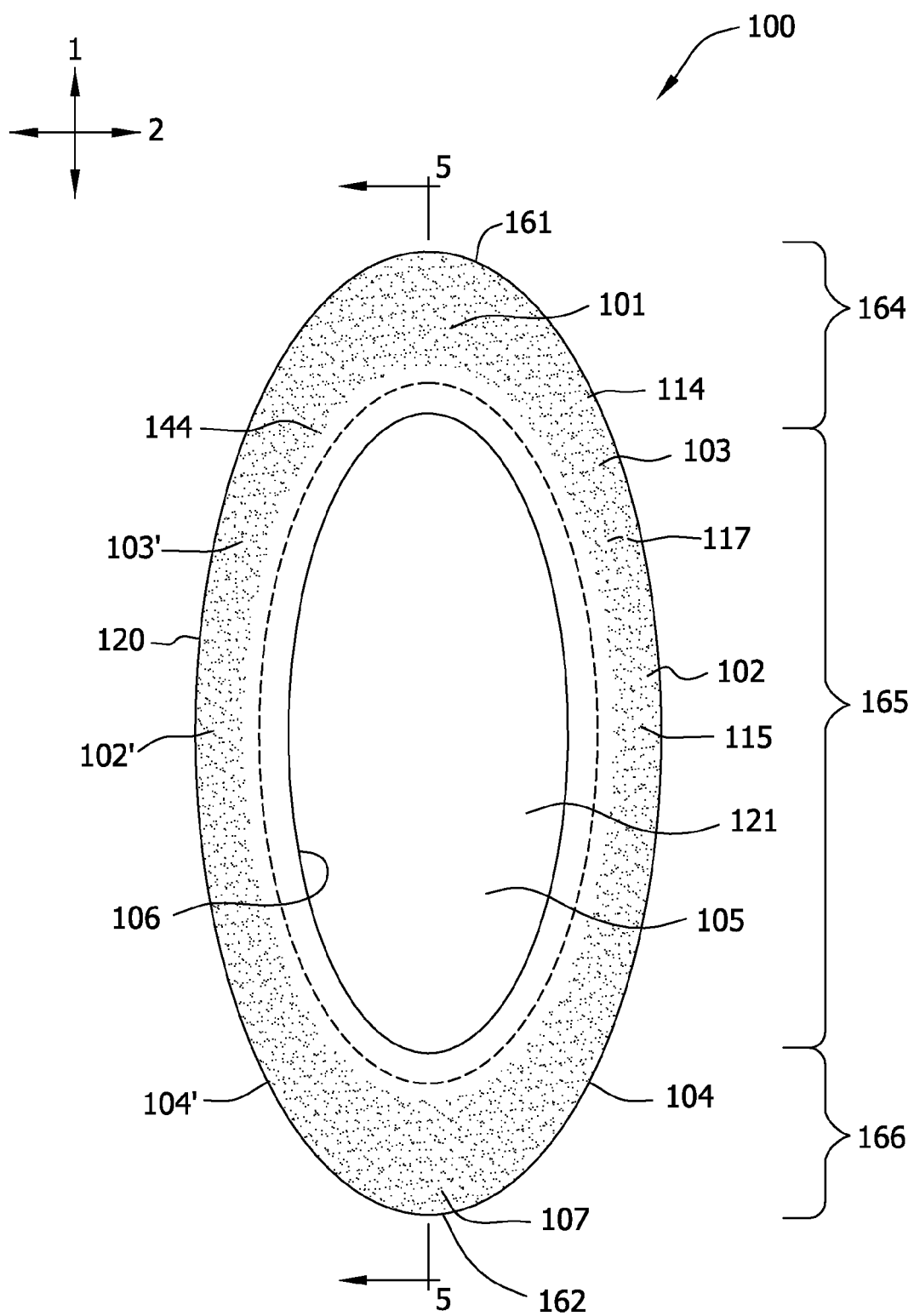
FIG. 2 shows a top view of another embodiment of an absorbent article of the present invention.
Figure 3:
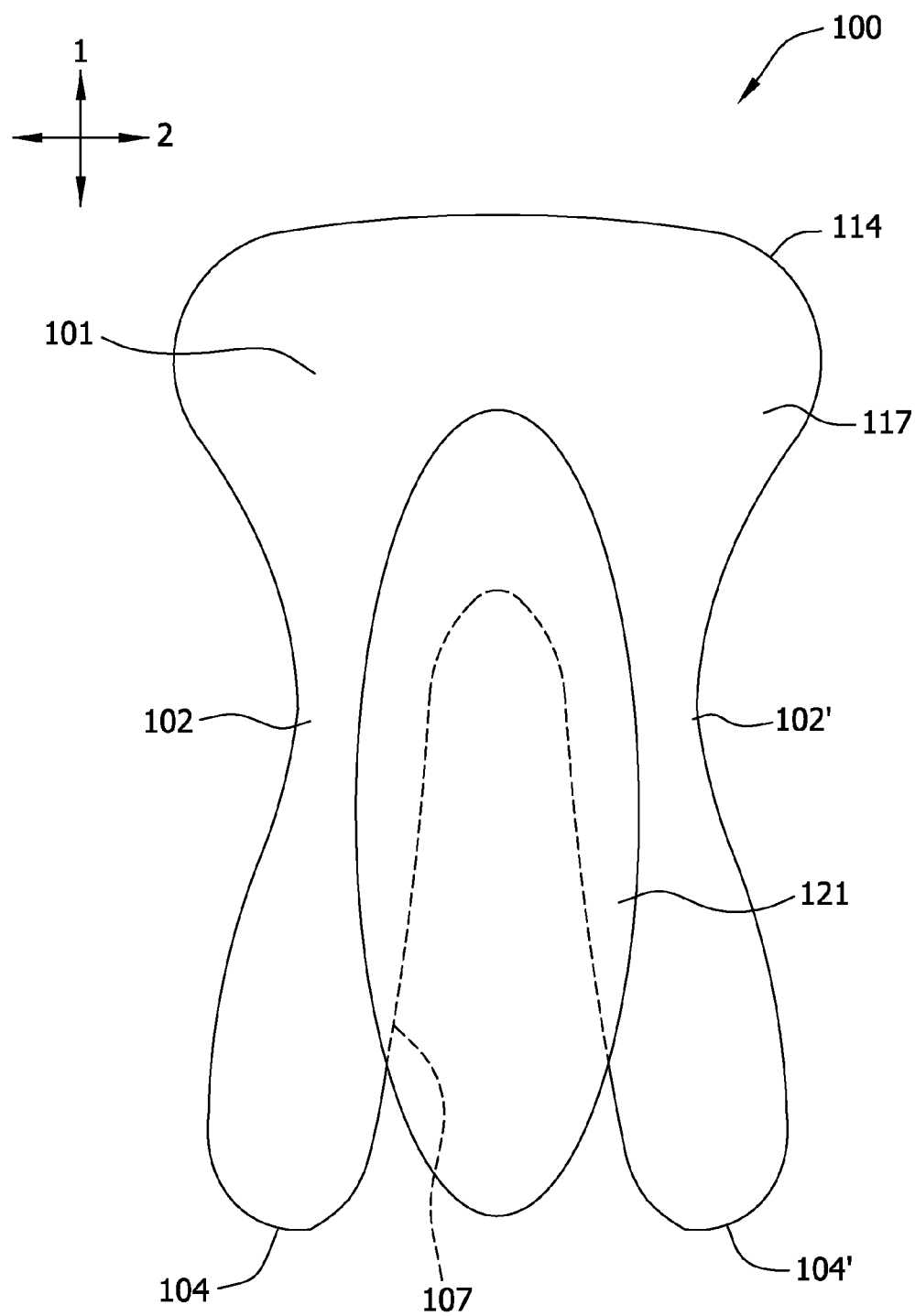
FIG. 3 shows a bottom view of the absorbent article shown in FIG. 1.
Figure 4:
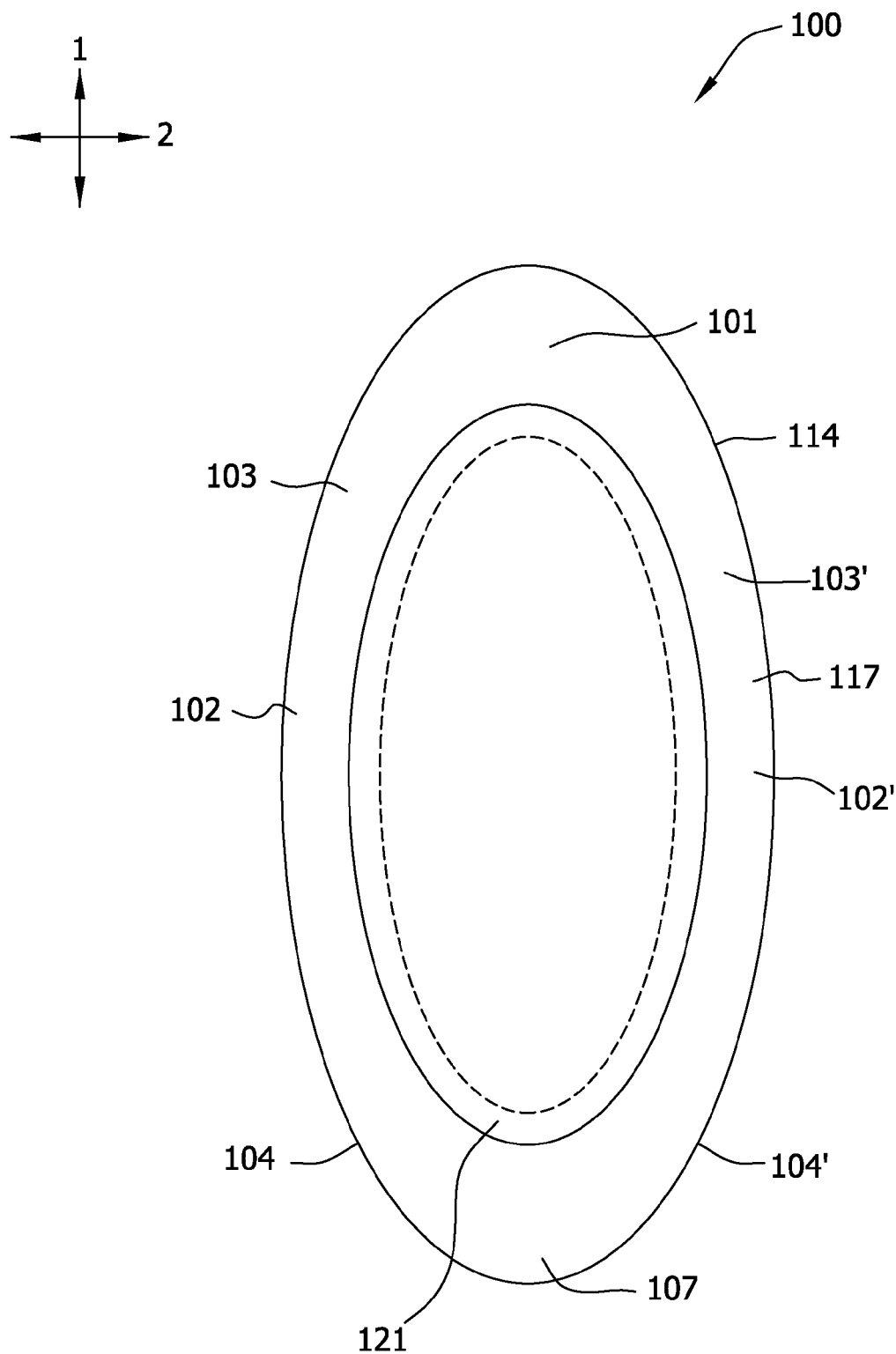
FIG. 4 shows a bottom view of the absorbent article shown in FIG. 2.

To gain a better understanding of the present invention, attention is directed to the Figures of the present specification. As is shown in each of the Figures, in particular FIGS. 1 and 2, the absorbent article 100 has a longitudinal direction 1 and a lateral direction 2. One component of the absorbent article 100 is a shell 114. This shell 114 has a first side 115, as shown in FIGS. 1 and 2, and a second side 117, as is shown in FIGS. 3 and 4. The shell 114 serves to provide the overall contour or silhouette of the absorbent article of the present invention. In addition, the shell 114 also provides a surface for attachment or adhesion of the absorbent article 100 to the body of a wearer.

The first side 115 of the shell 114 is the body facing side of the absorbent article 100 and the second side 117 of the shell 114 is the garment facing side of the absorbent article. The shell 114 of the absorbent article 100 has a first region 101. This first region 101 has a pair of lateral side regions 102, 102' extending from the first region. This pair of lateral side regions each has a proximate end 103, 103' adjacent the first region 101 and a distal end 104, 104'. The pair of lateral side regions 102, 102' and the first region 101 together define an opening 105 in the shell 114. This opening 105 may be open near the distal ends 104, 104' of the lateral side regions 102, 102', as is shown in FIG. 1 or, as shown in FIG. 2, the lateral side regions 102, 102' may be joined at the distal end 104, 104' to form a second region 107. The portions of the lateral side regions 102, 102' and the first region 101 adjacent the opening 105 form a circumference or edge 106 around the opening 105. This circumference or edge 106 typically has thickness in the z-direction 3 which is about equal to the thickness of the shell. However, the thickness of the edge may be increased or decreased to improve comfort for a wearer or performance of the absorbent article.

The absorbent article 100 further has an absorbent structure 121 attached to the second side 117 of the shell 114, as is shown in FIGS. 1-6. At least a portion of the absorbent structure 121 is positioned in the absorbent article such that a majority of the opening 105 in the shell has the absorbent structure 121 positioned therein, as can be seen in FIGS. 1 and 2. In one particular embodiment, the entire area of the opening 105 has the absorbent structure 121 positioned therein. Generally to hold the absorbent structure in place, a portion of the absorbent structure 121 is attached to the second side 117 of the shell 114. Suitable methods of attaching the absorbent structure 121 to the second side 117 of the shell 114 includes adhesives, mechanically bonding the absorbent structure 121 to the second side 117 using bonding means such as ultrasonic bonding, heat and pressure bonding and the like, which are discussed in more detail below.

In one embodiment of the present invention, the opening 105 in the shell may be a hole, which is devoid of any material, or and in another embodiment of the present invention the opening 105 may be a region which is permeable to body fluids. If the opening is a region which is permeable, the opening may have a material such as hydrogel or similar material that will allow body fluids to flow through the material.

In one embodiment, the first side 115 of the shell 114 is adapted to be the body contacting side of the absorbent article. The first region 101, the lateral sides regions 102, 102' and the second region 107, when present, on the first side 115 of the shell 114 are designed or adapted to contact, attach or adhere to the wearer's skin. In one particular embodiment, the first region 101 of the shell 114 is designed or adapted to contact a female wearer's skin surrounding the vulva region of the female torso when the absorbent article 100 is applied to the wearer. By "designed or adapted to contact a female wearer's skin surrounding the vulva region of the female torso", it is meant that the size and shape of the shell 114, including the first region and the lateral side regions and second region, if present, is such that the shell 114 fits in the vulva region and possibly the surrounding pubic region and perinea regions of the female torso. Generally, the shell 114 is sized and shaped such that the extent of the first side 115 of the shell 114 only contacts and attaches or adheres to the skin surrounding and proximate to the vulva area and possibly the pubic and perinea regions of the wearer. In addition to contacting the skin in the vulva, pubic and perinea regions of the wearer, the first side 115 of the shell 114 may also contact and attach or adhere to any hair in the vulva area of the wearer which may be present. The first side 115 of the shell 114 is what holds the absorbent article in place on the body of a wearer.

To gain a better understanding of the vulva region and surrounding regions of the female body, a general description of the anatomical structures can be found in *The Illustrated Running Press Edition of the American Classic Gray's Anatomy* (1974) by Henry Gray and *Structure and Function in Man* (1974) by Stanley W. Jacob, M.D., F.A.C.S. and relevant portions are included herein by reference. The general form can be found in *Anatomy for an Artist: Elements of Form* by Eliot Goldfinger and relevant portions are included herein by reference. The general description of the pubic hair covering these regions can be found in *Woman's Body: A Manual for Life* and relevant portions are included herein by reference.

The female anatomical structures to be described include the leg and the lower torso. The external anatomical structures of the lower torso include gluteal region and perineum region. The gluteal region includes the buttocks and the anus. The anatomical structure involved on the leg is the medial surface of the upper thigh.

The gluteal region includes generally the buttocks and anus and is typically bound in front by the line of the buttocks and the gluteal folds, in the back by the sacral triangle and the sides by lines extending through the greater trochanters. The shape of the gluteal region is roughly hemi-spherical and convex, and is determined by a series of muscles including the gluteus maximus and a series of fat pads including the posterior gluteal fat pad. The line of the buttocks separates the gluteal region and the perineum region.

The upper thigh region includes typically the right and left thigh and is typically bound on top by the thigh lines and the sides by the front and back of the leg. The thigh lines are two lines that are on either side of the labia and each of the lines runs along the line of the inguinal ligament to the gluteal folds and marks where the upper thigh meets the lower torso. The shape of the region is roughly a portion of a tapered cylinder and convex, and is shaped by a series of muscle groups including the gracilis, pectineus, adductor longus, adductor brevis, and adductor magnus and series of fat pads including the inner thigh fat pad.

The perineum region, which extends from the inferior outlet of the pelvis to the bony structure of the coccyx, is comprised of two divisions, the urogenital triangle and the anal division or obstetrical perineum. The region includes the external organs of reproduction; the mons pubis, labia majora and minora, clitoris, meatus urinarius and the opening to the vagina. The region is generally bound in front by the lower abdominal line, on the sides the thigh lines, and in the back the line of the buttocks. The abdominal line is a line that passes across the top of the pubis. The lines of the buttocks are lines that connect the thigh lines to the gluteal cleft. For convenience in describing the form and created spaces in the perineum region, this region will be subdivided into three regions an anterior region including the mons pubis, a central region including the labia majora and minora, and posterior region. The anterior region is bound in front by the lower abdominal line, in back by anterior commissure, and on the sides by line of the labia. The central region is bound in front by the anterior commissure, in the back by the posterior commissure, and on the side by the line of the labia. The posterior region is bound in front by the line of the labia, in the back by the lines of the buttocks, and on the sides the thigh line.

The vulva region includes the female external genitalia and generally includes the anterior and central regions of the perineum. The mons pubis [or veneris] is generally a rounded eminence in front of the symphysis pubis, formed by a collection of fatty tissue including the pubic fat pad beneath the integument and is generally covered with pubic hair. The labia majora are generally two prominent longitudinal cutaneous folds extending downward from the mons veneris to the anterior boundary of the perineum, and generally enclosing the common urinary-sexual opening. The space between the two folds is the labial cleft. Each labium has generally two surfaces, an outer, which is pigmented and covered generally with strong, crisp pubic hairs, and an inner within the labia cleft, which is smooth and is beset with large sebaceous follicles and is continuous with the genito-urinary mucous tract; between the two there is considerable quantity of areolar tissue, fat including the labia fat pad, and tissue besides vessels, meeting the anterior commissure. Posteriorly they are typically not joined, but generally appear to become lost in the neighboring integument, terminating close to, and nearly parallel with each other. Together with the connecting skin between them, they form the posterior commissure or posterior boundary of the vulval orifice. The interval between the posterior commissure and the anus constitutes the perineum region. The fourchette is the anterior edge of the perineum, and between it and the hymen is a depression, the fossa navicularis. The line of the labia separates the labia and the perineum region.

The labia minora are two small cutaneous folds, situated generally within the labia majora, and extending from the clitoris obliquely downward, outward, and backward on each side of the orifice of the vagina.

The form of the perineum, gluteal, and upper thigh regions combine to form a very intricate skin topography and spaces. The roughly two-hemispherical-like forms of the buttocks, the roughly tapered-cylinder-like form of the upper thigh, split-teardrop-like form of the vulvar region create intricate generally convex topography with intersections to form a series of recesses. The generally convex topography of the buttocks, the vulvar region, and upper thigh join to create spaces including two inner thigh grooves along two thigh lines, a depression in the posterior perineum region and a cleft extending through the labia and gluteal clefts. The grooves, depression, and cleft are like interconnected recesses in the topography. The central region general has lateral sides separated by a distal surface created by the labial cleft and includes the labial cleft.

Pubic hair generally cover some of these regions and fill in a portion of these recesses especially the labial cleft and the portion of the groove of the thigh parallel to the labial cleft to create a hair surface topography. The hair topography is the surface topography of an imaginary distal surface created by the hair. The depression of the perineum, thigh groove parallel to the gluteal cleft, and the gluteal cleft generally has little or no pubic hair. The skin topography combines with the hair topography to create an overall body topography.

This intricate space created by the intricate body form in this region of the body varies between women in both size and form, and varies with the position and movement of the women. Some of these variations are summarized in "Female genital appearance: 'normality' unfolds" by Jillian Lloyd et. al., BJOG: An International Journal of Obstetrics and Gynecology, May 2005, Vol. 112, pp. 643-646 and is included herein by reference.

As a woman ages, many changes occur to the vulva region. Skin begins to lose its elasticity and hangs more loosely from the body. In addition, the fat pads tend to be reduced, changing the topography of the vulva region. As a result, there is a need for a product which can be adapted to these changing conditions.

When the absorbent article of the present invention is positioned for use on a wearer, generally the first side 115 of the shell, including the first region 101, the lateral side regions 102, 102' and the second region 107, if present, are positioned on the wearer outside the labia majora of the wearer. This will allow any fluid coming from the vulvo-vaginal area of the body of a wearer to pass through the opening 105 present in the shell 114, so that the fluid may flow into the absorbent structure 121. The opening 105 could be an area which is devoid of the shell material or any other material. Alternatively, the opening may be a permeable area, which is permeable to body fluids, containing a material which is permeable. Typically, the absorbent structure 121 is the portion of the absorbent article which provides absorbency to the absorbent article. In an alternative embodiment, the first side 115 of the shell 114 may also provide some absorbency to the absorbent article. For example, the second first side 115 of the shell 114 may contain an absorbent material integrated into the shell 114, such that the first side of the shell 114 has some degree of absorbency. The first side 115 of the shell 114 may have an absorbent material coated or impregnated into the shell material.

When the second region 107 is present, as shown in FIG. 2, the entire opening 105 is surrounded by the shell 114. When the second region 107 is not present, as shown in FIG. 1, the opening 105 has an unbound end, meaning that the distal ends 104, 104' of the lateral side regions 102, 102' are not connected. Each configuration of the absorbent articles shown in FIGS. 1 and 2 have advantages. For example, the configuration shown in FIG. 1, where the second region 107 is not present in the absorbent article 100, the absorbent article 100 may provide more comfort to the wearer when being worn. That is, in use of the absorbent article 100, the first region 101 is designed to be placed towards the anterior region of the vulva region of the wearer. By not having the second region, the absorbent article 100 will not be positioned in the perinea region of the wearer, which may provide improved comfort to the wearer. Alternatively, by having the second region 107 present, the absorbent article may provide superior leak protection to the wearer, by creating a seal completely surrounding the labia majora of a wearer. As a result, any and all fluid leaving the vaginal cavity will be confined to the absorbent article.

Figure 6:
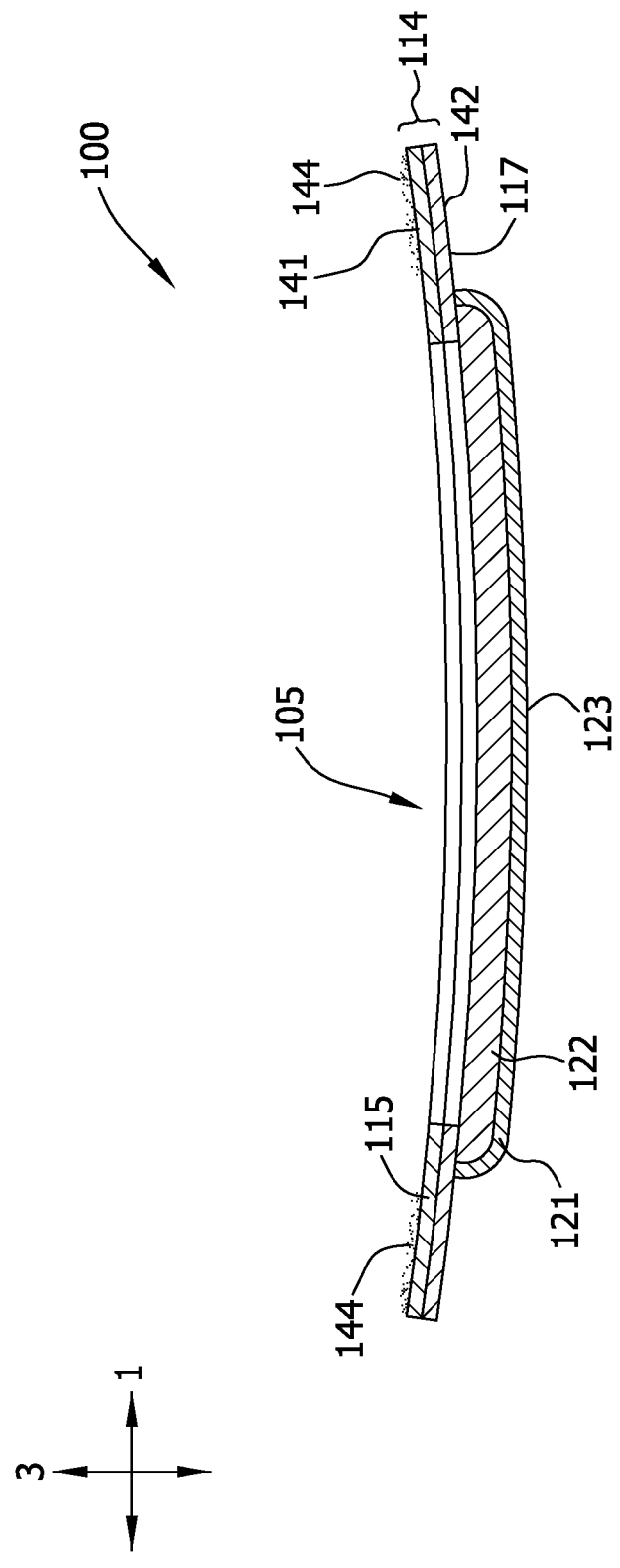
FIG. 6 shows a side cut-away view of an embodiment of an absorbent article of the present invention shown in FIG. 2 along line 5-5 having a two-layer shell.

The shell 114 of the absorbent article 100, which may be either liquid impermeable or liquid permeable, can be prepared from a variety of materials. In one embodiment, the shell may include a layer constructed of any material which will function to be operatively liquid impermeable. The shell 114 may, for example, include a polymeric film, a woven fabric, a nonwoven fabric or the like, as well as combinations or composites thereof. For example, the shell 114 may include a polymer film laminated to a woven or nonwoven fabric. A laminate shell 114 structure is shown in FIG. 6, having an upper layer 141 and a lower layer 142, wherein the upper layer 141 is the body-facing side of the shell 114 and the lower layer 142 is the garment facing side of the shell 114. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the shell 114 can operatively permit a sufficient passage of air and moisture vapor out of the absorbent article 100, particularly out of an absorbent structure 121 while blocking the passage of bodily fluids and odors often associated with bodily fluids. An example of a suitable shell material can include a breathable, microporous film, such as those described in, for example, U.S. Pat. No. 6,045,900 to Haffner et al., the entire disclosure of which is incorporated herein by reference and made a part hereof. Other shell materials which are extensible may be used in the present invention, including, for example foams. One example of a suitable foam is a polyurethane foam with a negative Poissons ratio. Examples of extensible backsheet materials are described in U.S. Pat. No. 5,611,790, issued Mar. 18, 1997, to Osborn, III et al., herein incorporated by reference in its entirety. Other materials that are inherently breathable, such as polyurethanes, may be used to form the shell 114. It is contemplated that is some embodiments, the shell 114 can be liquid permeable without departing from the scope of this invention.

In one particular embodiment of the present invention, the shell 114 may be a laminate of a woven or nonwoven fabric with a silicone polymer, wherein the silicone polymer has adhesive properties. The second side 117 of the shell will be woven or nonwoven fabric and the first side 115 of the shell will be silicone polymer. One commercially available laminate is an Oleeva Fabric® 1 available from Bio Med Sciences, Inc., which have offices at 7584 Morris Court, Suite 218 Allentown, Pa. 18106. The Oleeva Fabric® is a silicone sheeting having adhesive properties laminated to a fabric backing. The silicone sheeting will form the body facing first side 115 of the shell material. Relating this particular structure to the Figures, in FIG. 6, the silicone polymer is the upper layer 141 of the shell 114 and the nonwoven or woven layer is the lower layer 142 of the shell.

Bicomponent films or other multi-component films can also be used as the shell 114 material. In addition, woven and/or nonwoven fabrics which have been treated to render them operatively liquid-impermeable can also be used as an effective shell 114 material. Another suitable shell material can include foams. Examples of foam include a closed-cell polyolefin foam, a foam with a negative Poissons ration and other similar foams. Other suitable polymeric materials include a polyurethane polymer material, a silicone polymer or other similar materials. Silicone polymers having naturally occurring adhesive properties, or silicone polymers having a silicone adhesive layer applied thereto are of particular interest for the shell material. Such silicone polymers will allow the first side 115 of the shell 114 to adhere to the body of the wearer without the need of an additional adhesive. These materials may be laminated to another material, such that the second side 117 of the shell 114, which is the garment facing side of the absorbent article 100 is laminated to the other material, so that the adhesive nature of the silicone polymer does not adhere the garment to the undergarments of the wearer. In another embodiment of the present invention, the shell material may be prepared from an interpenetrating polymer network or two or more polymers. Generally, one of the polymers of the interpenetrating polymer network may be a silicone material. Examples of interpenetrating polymer networks are described in U.S. Pat. No. 5,759,560, issued to Dillion, which is hereby incorporated by reference in its entirety.

The shell material should be selected such that the overall properties of the shell allow the shell material to move with the skin of the wearer during normal use and normal movements by the wearer during use. By "normal movement by the wearer" it is meant any movement that normally occurs during use of the absorbent article, including walking, running, sitting, standing, kneeling, riding a bicycle, exercising, playing sports, getting into and out of an automobile, and other similar movements made by wearers when wearing an absorbent article. The shell should not be too rigid, such that the shell detaches from the skin of the wearer during use and the shell should not be so flexible that the shell tends to twist and bunch during use. The shell should have sufficient flexibility to conform to the skin of the wearer and become similar to a second skin of the wearer. The shell should also have the ability to remain attached to the body of the wearer under moist or wet conditions. In addition, the shell should be sufficiently stretchable so that it stretches, as needed, during movement of the wearer.

Generally, the shell material should have sufficient thickness to allow the shell 114 to mold to the body of the wearer, but not too thick that the shell 114 becomes uncomfortable for the wearer to wear. In addition, the shell 114 should not be so thin that it ineffectively forms a seal with the skin of the wearer when applied to the wearer, or becomes detached from the skin of the wearer during use and normal movement of the wearer during use or that it does not adequately conform to the shape and skin of the wearer at the point of attachment to the wearer. Depending on the material used for the shell, the typical thickness of the shell is between 0.03 mm and about 5.0 mm, more particularly between 0.1 mm and 3.0 mm. In one particular embodiment, the thickness of the shell is between 0.25 mm and about 3.0 mm. Again, the actual thickness used is dependent of several factors including rigidity of the material, the flexibility of the material and the ability of the material to assume the shape of the skin of the wearer at the location of use, which is typically the vulva region of a wearer.

The second side 117 of the shell 114 may form a portion of the garment-facing side of the absorbent article 100 when worn by a wearer. The shell material should be selected such that the second side 117 of the shell will freely move against the undergarment or clothing of a wearer. One way to achieve this result is to construct the second side 117 of the shell 114 to have a fairly low coefficient of friction. This will allow the second side 117 of the shell 114 to freely move against the undergarment or other clothing worn by the wearer. If the second side 117 of the shell 114, does not freely move against the undergarment or other clothing worn by the wearer, the absorbent article may catch on the undergarment or clothing, which may result in the absorbent article being prematurely and undesirably removed from the wearer or may cause the absorbent article to be shifted from its desired placement against the body of a wearer.

In order to achieve the desired coefficient of friction on the second side 117 of the shell 114, the materials used to prepare the shell could be selected such that the second side 117 of the shell material will inherently have the desired coefficient of friction. Alternatively, the second side 117 of the shell 114 may be treated with a coating composition, such a polytetrafluoroethylene containing coating, a silicone containing coating or other similar coating having low coefficient of friction properties. Alternatively, the shell 114 could be made from a laminate of two or more materials such that the first side 115 of the shell 114 is prepared from a material which meets the needed properties of the first side 115, while the material selected for the second side 117 of the shell 114 meets the desired coefficient of friction such that the second side 117 will move freely against the undergarment or garment being worn by a wearer.

Figure 5:
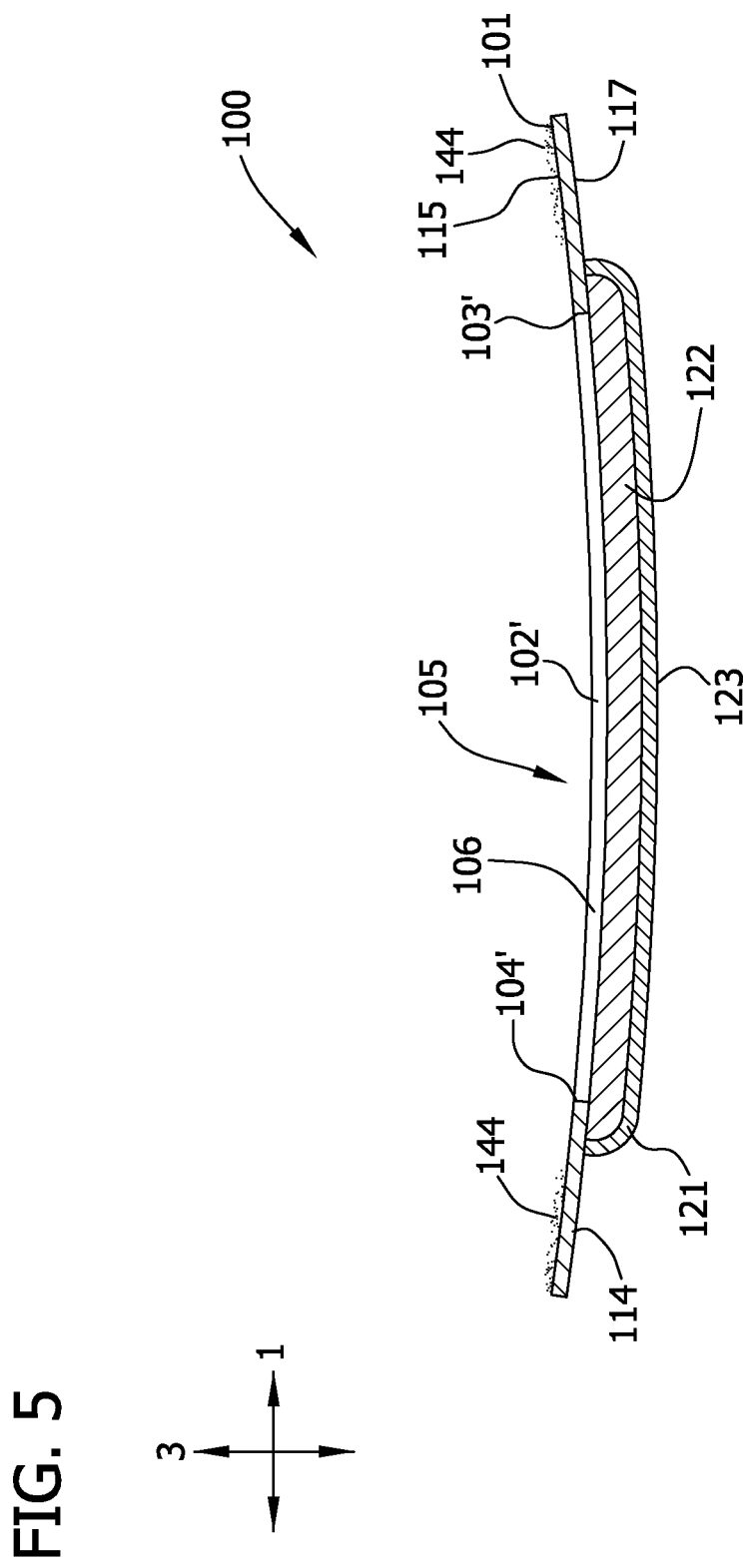
FIG. 5 shows a side cut-away view of an embodiment of an absorbent article of the present invention shown in FIG. 2 along line 5-5.

The shell 114 of the absorbent article 100 may be flat or may have a three-dimensional shape. As is shown in FIG. 5, which is a cross-sectional side view of the absorbent article, the shell 114 has a three-dimensional concave shape. Alternatively, as is shown in cross-sectional side views of FIG. 6, the shell 114 may have a generally flat shape. By providing the absorbent article 100 with a three-dimensional concave shape, as is shown in FIG. 5, placement of the article may be easier for the wearer. Generally, the three-dimensional shape could be such that it closely matches the overall general curvature of the vulva region and optionally the pubic and perinea regions of most women, when the absorbent article is used as a panty-liner, sanitary napkin or a feminine incontinence article. To form the shell 114 with a three-dimensional shape, the shell may be molded in any manner known to those skilled in the art, for example heat molding. The manner in which the three-dimensional shape is imparted to the shell 114 is not critical to the present invention.

When the shell 114 is a generally flat shape, for example as shown in FIG. 6, meaning that the shell does not have a third dimension other than thickness, the shell 114 should be made to be flexible enough that the shell 114 can conform to the body of the wearer at the point of attachment. In addition to being flat, the overall shape of the shell 114 may be contoured, as is shown in FIG. 1. In one embodiment, the contour shape may be such that the narrowest point of the contour is in the crotch area of the shell 114 nearest the vulva region, as is shown in FIG. 1. The contour shape shown in FIG. 1 is one of many possible shapes, in which the shell 114 and absorbent article may be prepared. Other shapes may be used, without departing from the scope of the present invention. Generally, the shape selected should be such that the shell 114 and absorbent article 100 are comfortable for the wearer to wear, while providing leakage protection to the wearer. It is noted that a contour shape may also be used in conjunction with a three-dimensional shell. Further discussion of the overall shape of the absorbent article may be found below.

The shell may be any desired color or may be translucent. In addition, the shell may have a matte finish, satin finish or a smooth finish. The particular finish color or translucency can be a matter of choice for the manufacturer of the absorbent article of the present invention. However, a translucent shell may assist the user in placing the absorbent article 100 since the user may be able to see where the article is compared to the genitalia of the user.

The absorbent structure 121 is designed to absorb body exudates, including menstrual fluid, blood, urine, and other bodily fluids, such as sweat and vaginal discharges. The absorbent structure 121 has a longitudinal direction 1 and a lateral direction 2 and is shown in FIGS. 1-4, and a thickness in the z-direction 3, as is shown in FIGS. 5 and 6. This absorbent structure 121 may be a single layer or may be multiple layers. Typically, the absorbent structure 121 has an absorbent core 122 and a generally liquid impermeable backsheet 123. This absorbent core 122 may contain one or more layers of absorbent materials. That is, the absorbent core 122 may be a single layer of absorbent materials or may be a multilayer structure. Each of the layers of the absorbent core 122 can contain similar materials or different materials. In the absorbent article 100 of the present invention, the materials which may be used to form the absorbent core 122 include those materials conventionally used in absorbent articles and includes materials, such as, for example, foam, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A desired material is wood pulp fluff, for it is low in cost, relatively easy to form, and has good absorbency.

The absorbent core 122 can also be formed from a composite comprised of a hydrophilic material which may be formed from various natural or synthetic fibers, wood pulp fibers, regenerated cellulose or cotton fibers, or a blend of pulp and other fibers. One particular example of a material which may be used as the absorbent core is an airlaid material. The absorbent core 122 may have other properties including extensibility, which will allow the absorbent core to be extended or fit to a particular wearer. One example of extensible absorbent cores is described in U.S. Pat. No. 5,611,790, issued Mar. 18, 1997, to Osborn, III et al., herein incorporated by reference in its entirety.

In one embodiment, the absorbent core 122 may also include a superabsorbent material, in addition to or in place of the hydrophilic material, which increases the ability of the absorbent core to absorb a large amount of fluid in relation to its own weight. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g., saline with 0.9 wt % NaCl). The superabsorbent materials can be inserted as particles or in sheet form. The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Hydroxyfunctional polymers have been found to be good superabsorbents for sanitary napkins. Such superabsorbents are commercially available from Evonik Industries, among others, and are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

Selection of the actual materials used for the absorbent core 122 is within the skill of those skilled in the art. The actual materials used for the absorbent core are not critical to the present invention.

The generally liquid impermeable backsheet 123 is present in the absorbent structure 121 to prevent fluid entering the absorbent core 122 from flowing through the absorbent core 122 and onto a garment or undergarment being worn by a wearer. Suitable liquid impermeable backing sheets include, for example, a polymeric film, a woven fabric, a nonwoven fabric or the like, as well as combinations or composites thereof. Generally, any material that may be used as the shell material described above may be used as the backsheet 123 of the absorbent structure 121. The liquid impermeable backsheet 123 may be a polymeric film, a woven fabric, a nonwoven fabric or the like, as well as combinations or composites thereof. For example, the liquid impermeable backsheet 123 may include a polymer film laminated to a woven or nonwoven fabric. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the liquid impermeable backsheet 123 can operatively permit a sufficient passage of air and moisture vapor out of the absorbent article 100, particularly out of an absorbent structure 121 while blocking the passage of bodily fluids and odors often associated with bodily fluids. An example of suitable materials for the liquid impermeable backsheet 123 can include a breathable, microporous film, such as those described in, for example, U.S. Pat. No. 6,045,900 to Haffner et al., the entire disclosure of which is incorporated herein by reference and made a part hereof.

The side of the backsheet 123 which faces the undergarment or garments of a wearer should have a low coefficient of friction for the same reasons that the second side 117 of the shell should have a low coefficient of friction. This will allow the garment facing side of the backsheet 123 to move freely against the undergarment or clothing of a wearer. If the garment facing side of the backsheet 123 does not freely move against the undergarment or other clothing worn by the wearer, the absorbent article may catch on the undergarment or clothing, which may result in the absorbent article or the absorbent structure being prematurely and undesirably removed from the wearer or may cause the absorbent article to be shifted from its desired placement against the body of a wearer. In addition by having both the garment facing side of the backsheet 123 and the second side 117 of the shell freely move against the undergarment or clothing of the wearer, the body attached absorbent article will be comfortable for a wearer to wear and may provide improved protection since the undergarment or clothing will not cause the absorbent article to shift during use.

Generally, the absorbent structure will be positioned adjacent to the second side 117 of the shell 114, as can be clearly seen in FIGS. 1-6. By "adjacent to the shell", it is meant that the absorbent structure 121 is directly in contact with the second side 117 of the shell 114 or may be separated by one or two additional layers or a construction or pressure sensitive adhesive. The absorbent structure should be positioned such that the absorbent core 122 is beneath the opening 105 so that any fluid flowing through the opening 105 will come into contact with the absorbent core 122.

In addition to the absorbent core 122, the absorbent structure 121 may have other additional layers which aid the absorbent core 122 in capturing and holding the bodily fluid into the absorbent core 122. These other layers, when present and in combination with the absorbent core 122, form the absorbent structure 121 of the absorbent article 100. There may be a single layer or multiple layers in addition to the absorbent core 122 in the absorbent structure 121.

One particular example of an additional layer which may be used in addition to the absorbent core 122 in the absorbent structure 121 is a top sheet 124, which is generally a liquid permeable material, which allows bodily fluids to pass through the top-sheet into the absorbent core. The top sheet 124 also may provide a wearer with a dry feeling by separating the absorbent core 122 from the body of the wearer. That is, the top sheet 124 is placed between the absorbent core 122 and the body of the wearer and such that the absorbent core 122 is between the top sheet 124 and the shell 114.

Optionally, the top sheet 124 may be formed from one or more materials. The top sheet 124 should be able to manage different body excretions depending on the type of product. In feminine care products, often the top sheet 124 must be able to handle menses and urine. In addition, the top sheet 124 may be comfortable, soft and friendly to the wearer's skin. In the present invention, the top sheet 124 may include a layer constructed of any operative material, and may be a composite material. For example, the top sheet can include a woven fabric, a nonwoven fabric, a polymer film, a film-nonwoven fabric laminate or the like, as well as combinations thereof. Examples of a nonwoven fabric useable in the top sheet 124 include, for example, an airlaid nonwoven web, a spunbond nonwoven web, a meltblown nonwoven web, a bonded-carded web, a hydroentangled nonwoven web, a spunlace web or the like, as well as combinations thereof. Other examples of suitable materials for constructing the top sheet 124 can include rayon, bonded-carded webs of polyester, polypropylene, polyethylene, nylon, or other heat-bondable fibers, finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials. When the top sheet is a film or a film laminate, the film should be apertured or otherwise be made to allow fluids to flow through the top sheet to the absorbent core.

Other examples of suitable materials for the top sheet 124 are composite materials of a polymer and a nonwoven fabric material. The composite materials are typically in the form of integral sheets generally formed by the extrusion of a polymer onto a nonwoven web, such as a spunbond material. In a particular arrangement, the top sheet 124 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the liner or body contacting layer. The apertures or other openings can help increase the rate at which bodily liquids can move through the thickness of the liner or body contacting layer and penetrate into the other components of the article (e.g. into the absorbent core 122). The selected arrangement of liquid permeability is desirably present at least on an operative portion of the top sheet 124 that is appointed for placement on the body-side of the article. The top sheet 124 can provide comfort and conformability, and can function to direct bodily exudates away from the body and toward the absorbent core 122. The top sheet 124 can be configured to retain little or no liquid in its structure, and can be configured to provide a relatively comfortable and non-irritating surface next to the body tissues of a wearer. In the present invention, the top sheet 124 positioned over the absorbent core may have a surface which is embossed, printed or otherwise imparted with a pattern.

Additional layers or substrates, including for example, the liquid acquisition and distribution layer, also referred to as a surge or transfer layer, and an optional tissue layer are also incorporated into the absorbent structure 121 of the absorbent product 100, for example, between the top sheet 124 and the absorbent core 122. The distribution layer may be shorter than the absorbent core or have the same length as the absorbent core 122. The distribution layer serves to temporarily hold an insulting fluid to allow the absorbent core sufficient time to absorb the fluid, especially when a superabsorbent material is present.

In another embodiment, the absorbent core, transfer layer and other components, such as tissue layers, may be free floating (unattached) between the shell 114 and the top sheet 124, and are secured along only the peripheral edges thereof. Alternatively, the absorbent core 122, transfer layer, if present, and any other layer or component, if present, may be attached to one or both of the second side 117 of the shell 114 and top sheet 124 and/or to each other.

The absorbent structure 121, including the absorbent core 122, is generally attached to the second side 117 of the shell 114, such that the absorbent core is positioned under the opening 105 in the shell. The absorbent structure 121 may be attached to the shell 114 in a permanent manner, meaning that the absorbent structure is generally intended not to be removable by the wearer of the absorbent article 100. Alternatively, the absorbent structure 121 may be made to be removably attached to the shell, such that the absorbent structure 121 may be removed by a wearer of the absorbent article 100 and replaced with the same absorbent structure 121 or with another new absorbent structure 121. When the absorbent structure 121 is attached to the shell 114 in a permanent manner, meaning that the absorbent structure is not intended to be removed by the wearer, a construction adhesive may be used. Examples of useable construction adhesives include any adhesive which will effectively hold the absorbent structure 121 in place, so as not to be separated from the shell 114. Commercially available construction adhesives usable in the present invention include, for example Rextac adhesives available from Huntsman Polymers of Houston, Tex., as well as adhesives available from Bostik Findley, Inc, of Wauwatosa, Wis. Other means may be used to hold the absorbent structure 121 to the shell, including heat bonding, ultrasonic bonding or other similar mechanical attachments.

When the absorbent structure 121 is removably attached, the absorbent structure 121 is held in place to the second side 117 of the shell 114 by a means which will allow the wearer to remove the absorbent structure. One such means of holding the absorbent structure is by using a pressure sensitive adhesive. Suitable pressure sensitive adhesives include any commercially available pressure sensitive adhesive. Examples of suitable pressure sensitive adhesives usable to removably hold the absorbent structure 121 in place on the second side 117 of the shell 114 include pressure sensitive adhesives available from Henkel International. By providing an absorbent structure 121 which is removable, the shell 114 may be reused several times without the need to again place the shell 114 when the absorbent structure needs to be replaced. Other means, such as mechanical attachment may also be used to removably attach the absorbent structure 121 to the shell 114. Also by having a removable absorbent structure 121, the absorbent structure can be selected by the wearer prior to use. This would allow the wearer to select an appropriate level of protection for a given day or allow the wearer to select a size or shape of the absorbent which the wearer finds to be more comfortable. When the absorbent structure 121 is removable, and adhesively attached to the shell 114, the adhesive could be designed to remain on the shell or remain only on the absorbent structure. Generally, the adhesive should be placed on the absorbent structure 121, since this will provide fresh adhesive to hold the new absorbent in place each time the absorbent structure 121 is replaced. If the adhesive is present on the absorbent structure 121, a release sheet may be placed over the adhesive so that the adhesive is not contaminated with dirt or debris which may have an adverse effect in holding the absorbent structure 121 to the shell 114.

To aid a wearer in replacing the absorbent structure 121, placement aid may be present on the shell 114 and/or the absorbent structure. Suitable placement aids include the use of color, tactile indicators or any other means that would assist the wearer in replacing a removed absorbent structure.

Figure 7:
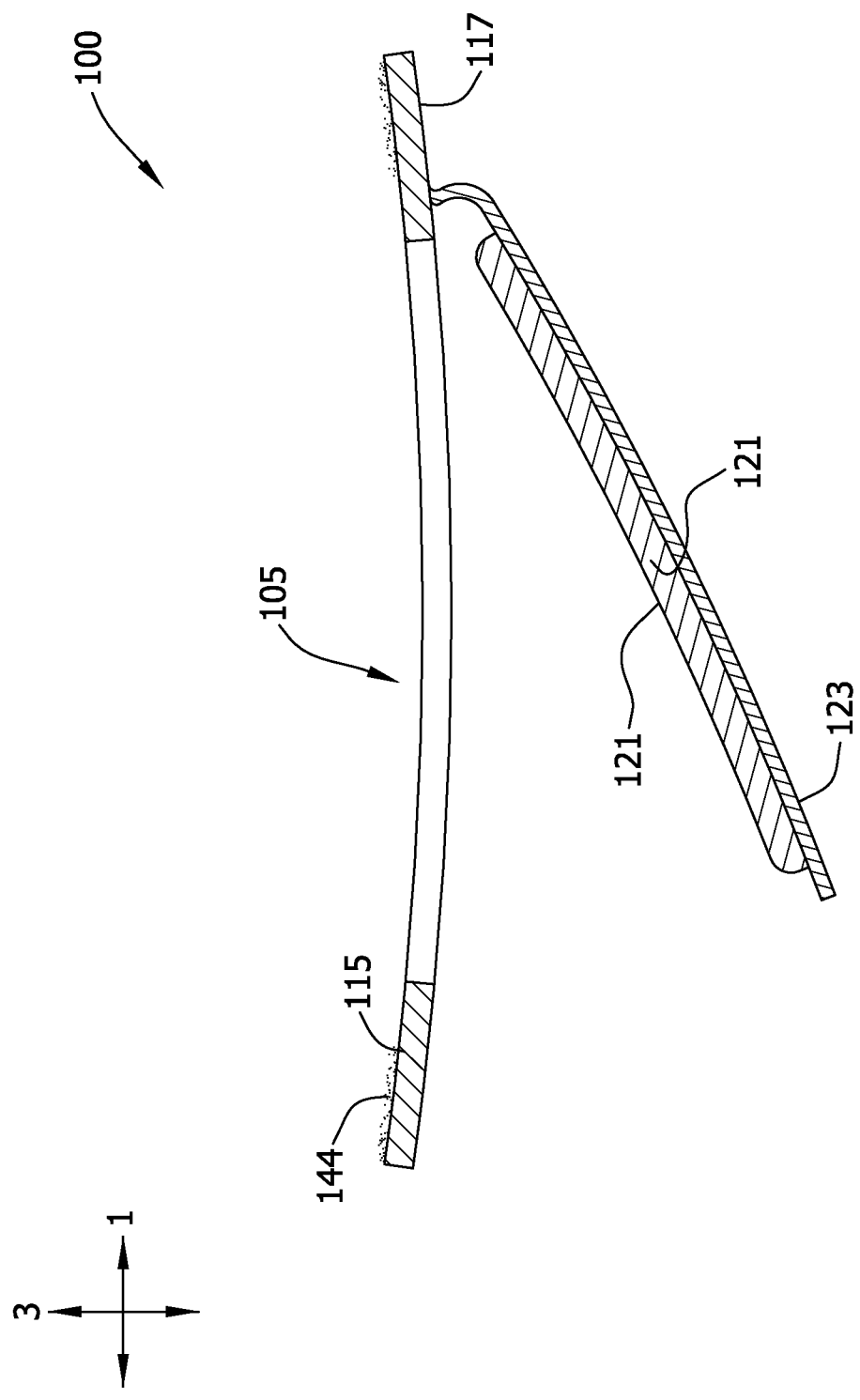
FIG. 7 shows a cross-sectional view of an embodiment of an absorbent article of the present invention having a hinged absorbent structure.

Another important advantage of having an absorbent structure, which is removable, is that the wearer may be able to perform normal bodily functions, such as urination. By having the absorbent which is removable, a wearer could remove the absorbent, urinate and replace the absorbent. This would alleviate the need of a wearer to have to replace the entire absorbent article 100 in order to form bodily functions. As another alternative, the absorbent structure 121 could be attached to the shell in such a manner that the absorbent structure is hinged with a hinging means, as is shown in FIG. 7.

The absorbent structure 121 may be a relatively flat structure, as shown in FIG. 6 or the absorbent structure 121 may be curved to match the shape of the shell 114, as is shown in FIG. 5. The size, location and shape of the absorbent structure 121 may also be selected for an intended use. For example, in an overnight use, the absorbent may be located further back on the wearer towards the perinea region of the wearer. In an overnight use, the absorbent structure may be larger than in a product intended for daytime use. In a daytime use, the absorbent structure will generally be centrally located in the vulva region.

In an alternative embodiment of the present invention, the shell 114 material may also be provided with some absorbency in addition to the absorbent structure 121. One way to achieve absorbency in the shell is to have the shell 114 prepared from a material which is a laminate of two or more materials. The first side 115 of the shell 114 contains an absorbent material within the body facing side of the laminate. For example, superabsorbent particles or materials may be incorporated into the material making up the body facing layer of the laminate. Another way is to place a very light coating onto the first side 115 of the shell material, wherein the coating contains superabsorbent particles or materials. Of course other absorbent materials, other than superabsorbent materials may be used in place of or in addition to the superabsorbent materials.

The absorbent core 122 of the absorbent structure 121 may be located entirely within the opening 105 in the shell 114, or the absorbent core 122 of the absorbent structure may extend past the opening 105 in the shell, as is shown in FIGS. 5 and 6, meaning that a portion of the absorbent core 122 contacts or is facing the second side 117 of the shell 114. Alternatively, the absorbent structure 121 may extend past the ends 104, 104' of the shell 114 or the second region 107 of the shell.

The liquid backsheet 123 may be a polymeric film, a woven fabric, a nonwoven fabric or the like, as well as combinations or composites thereof. For example, the liquid backsheet 123 may include a polymer film laminated to a woven or nonwoven fabric. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the liquid backsheet 123 can operatively permit a sufficient passage of air and moisture vapor out of the absorbent article 100, particularly out of an absorbent structure 121 while blocking the passage of bodily fluids and odors often associated with bodily fluids. An example of a suitable material for the liquid backsheet 123 can include a breathable, microporous film, such as those described in, for example, U.S. Pat. No. 6,045,900 to Haffner et al., the entire disclosure of which is incorporated herein by reference and made a part hereof. Other materials that may be used in preparing the backsheet 123 include materials which are inherently breathable, such as polyurethanes.

As is stated above, the first side 115 of the shell 114 either directly or indirectly attaches to the body of a wearer. Stated another way, the shell is the body attachment member and the first area 115 is the portion of the shell 114 which is attached to the body of the wearer. Depending on the material selected for the shell, the shell may actively attach to the body of the wearer using electrostatic means; suction means or a body adhesive may be placed on the first side 115 of the shell 114 to attach the absorbent article to the body of a wearer. Electrostatic means which can be used is by selecting the shell material to be a material which has an affinity for the body of a wearer, such that the shell material "clings" to the body of the wearer. Examples of such materials include ethylene vinyl acetate, low density polyethylene and other similar materials know to those skilled in the art. Suction means may be achieved by shaping the shell to conform to the body of the wearer, much like a contact lens fits to the eye. Generally, suction means can be achieved by forming the shell 114 into a three-dimensional shape. The easiest way to achieve body attachment is to place a body adhesive in the first side 115 of the shell 114.

A body adhesive 144 is positioned on the first side 115 of the shell 114. The body adhesive 144 contacts the skin and hair, if present, in the vulva region and possibly the pubic region and/or the perinea region of the wearer's body, thereby supporting and holding the absorbent article 100 against the body of the wearer during use. The body adhesive 144 can overlie a portion of the first side 115 or can overlie the first side 115 of the shell 114. Generally, the body adhesive 144 will be present on at least the outer portion first side of the shell near the edge 120 of the absorbent article 100. The adhesive may cover the entire first side 115 of the absorbent article (not shown in the drawings). Alternatively, the body adhesive 144 may be placed on a portion of the first side, as is shown in FIGS. 1 and 2. The body adhesive 144 may also be placed in a pattern of the first side 115 of the absorbent article. The body adhesive 144 can be applied to the first side 115 of the shell 114 of using any known process including inkjet printing, screen printing or extruding the body adhesive 144 from one or more nozzles, slot coating and the like.

Generally, any pressure sensitive adhesive known to those skilled in the art may be used, provided that the pressure sensitive adhesive is not a known irritant to human skin or that the adhesive is so aggressive that it causes pain to the wearer when the absorbent article is removed from the skin. It is also desirable that the adhesive is selected such that the adhesive does not leave a substantial amount of an adhesive residue on the surface of the skin of the wearer, when the absorbent article 100 is removed by the wearer after use. Particularly suitable pressure sensitive adhesive materials are disclosed in the commonly assigned U.S. Pat. No. 6,213,993 to Zacharias et al., U.S. Pat. No. 6,620,143 to Zacharias et al., the entire disclosure of each is incorporated herein by reference and made a part hereof. Other suitable adhesives are disclosed in U.S. Pat. No. 5,618,281 to Batrabet et al., the entire disclosure of which is incorporated herein by reference and made a part hereof. Other known body adhesives, such as those described in U.S. Pat. No. 6,316,524 to Corzani et al. which is hereby incorporated in its entirety, may also be used. Additional examples of pressure sensitive adhesives include hydrogels, hydrocolloids, acrylics based adhesives, and rubber based adhesives, such as Kraton based adhesives.

The body adhesive 144 may be positioned on the first side 115 of the shell 114 in an open pattern or a closed pattern. By "open pattern" is meant that the adhesive can have an intermittent or discontinuous pattern which does not substantially encircle the entire opening 105. For example, there may be breaks in the body adhesive at certain portions of the first side 115. "Closed pattern" means the adhesive 144 would encircle the entire opening 105 in the shell. In one embodiment, the pattern of the body adhesive 144 will substantially surround the cover of the first side 115 and substantially surround the opening 105. An example of an "open" pattern of the adhesive would be to have individual beads of adhesive applied in a discontinuous fashion. In the present invention, the closed pattern can be advantageous since the body adhesive 144 may form a seal with the body of the wearer which will assist in preventing leaks from the absorbent article 100. The body adhesive may form a dam, which may prevent leaks from the entire perimeter of the absorbent article 100.

In one embodiment of the present invention, the body adhesive 144 may be placed on the entire first side 115 of the shell 114, as is shown in FIG. 1. In another alternative embodiment of the present invention, as is shown in FIG. 2, the body adhesive 144 may be placed along the outer portions of the first side 115 near the periphery of the shell 114, such that no adhesive is near the opening 105. The body adhesive 144 may also be placed on the absorbent structure 121 positioned on the second side 117 of the shell 114 to help hold the absorbent article in place on the wearer. Generally, however, the body adhesive 144 is confined to being placed on the first side 115 of the shell 114, since placing the body adhesive on an area of the absorbent product 100 which contacts the female genitalia such as the labia majora may cause discomfort to the wearer of the absorbent product 100.

The adhesive may be applied in a pattern of small discrete dots so as to leave numerous areas free from adhesive. Alternatively, the adhesive may be applied as a continuous bead, or may be applied as a series of semi-continuous beads. Other suitable adhesive patterns may be selected for applying the body adhesive 144 to the body-contacting first side 115 of the absorbent article 100. For example, adhesive patterns can be oval, swirls, various linear or non-linear arrays of adhesive longitudinally, and/or transversely oriented and reticulated webs having unobstructed interstices between the adhesive fibers or combinations thereof. As stated above, the adhesive patterns may be open or closed. The weights of adhesives are limited to less than about 800 g/m2, and generally less than about 400 g/m2. Generally, the weight of the adhesive is at least 20 g/m2. Typically, the adhesive is applied in an amount of about 100 to about 400 g/m2. The limitations on the basis weight of the adhesive are important to provide the correct adhesive characteristics for applying directly to the wearer's vulva region and optionally the pubic and perinea regions of the wearer's body. If the basis weight is too high, the absorbent article will have a sticky feeling or otherwise uncomfortable feeling. If the basis weight of the adhesive is too low, there may be insufficient adhesion to the body of the wearer.

Generally, the body adhesive 144 is applied in a manner which is symmetrical about the longitudinal axis which bisects the absorbent article 100 and divides the absorbent article 100 into substantially equal portions. This symmetrical pattern provides the wearer a balanced feel when wearing the absorbent article 100. The symmetrical pattern also reduces the perception of any associated discomfort when the absorbent article 100 is removed from the body.

Figure 8:
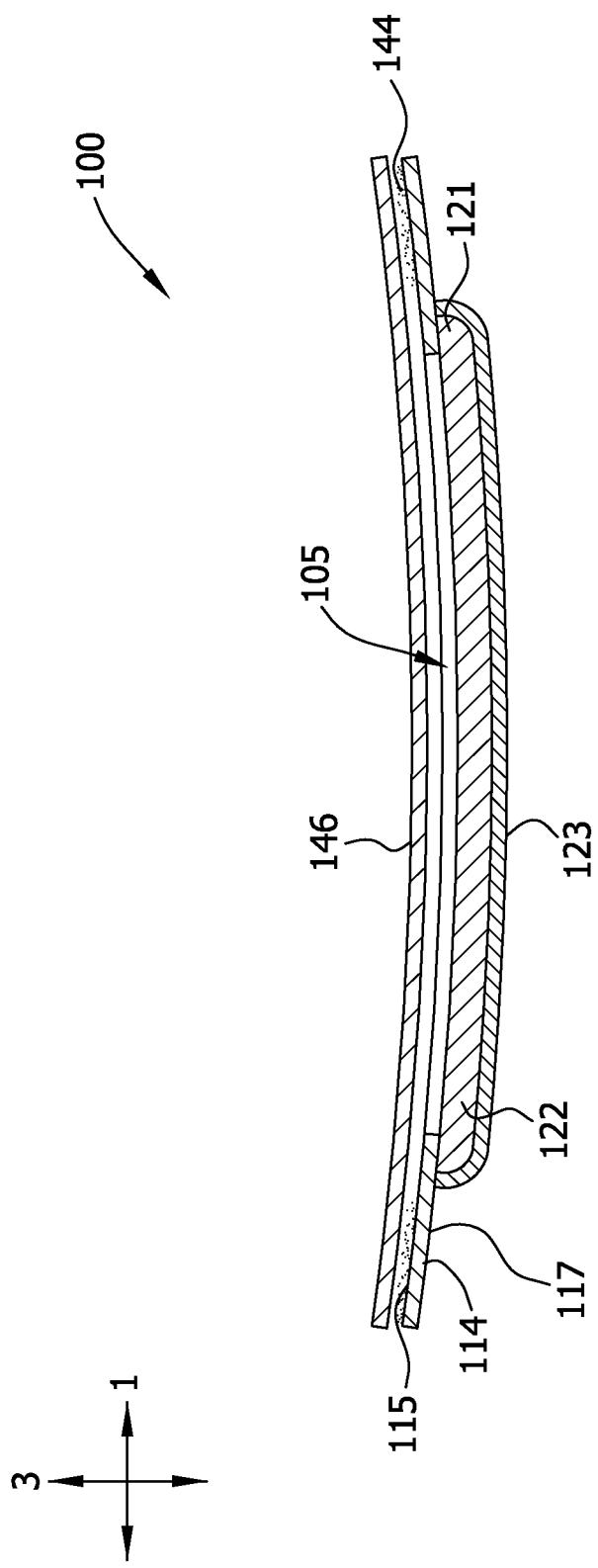
FIGS. 8 and 9 each show an absorbent article of the present invention having a release sheet applied thereto.
Figure 9:
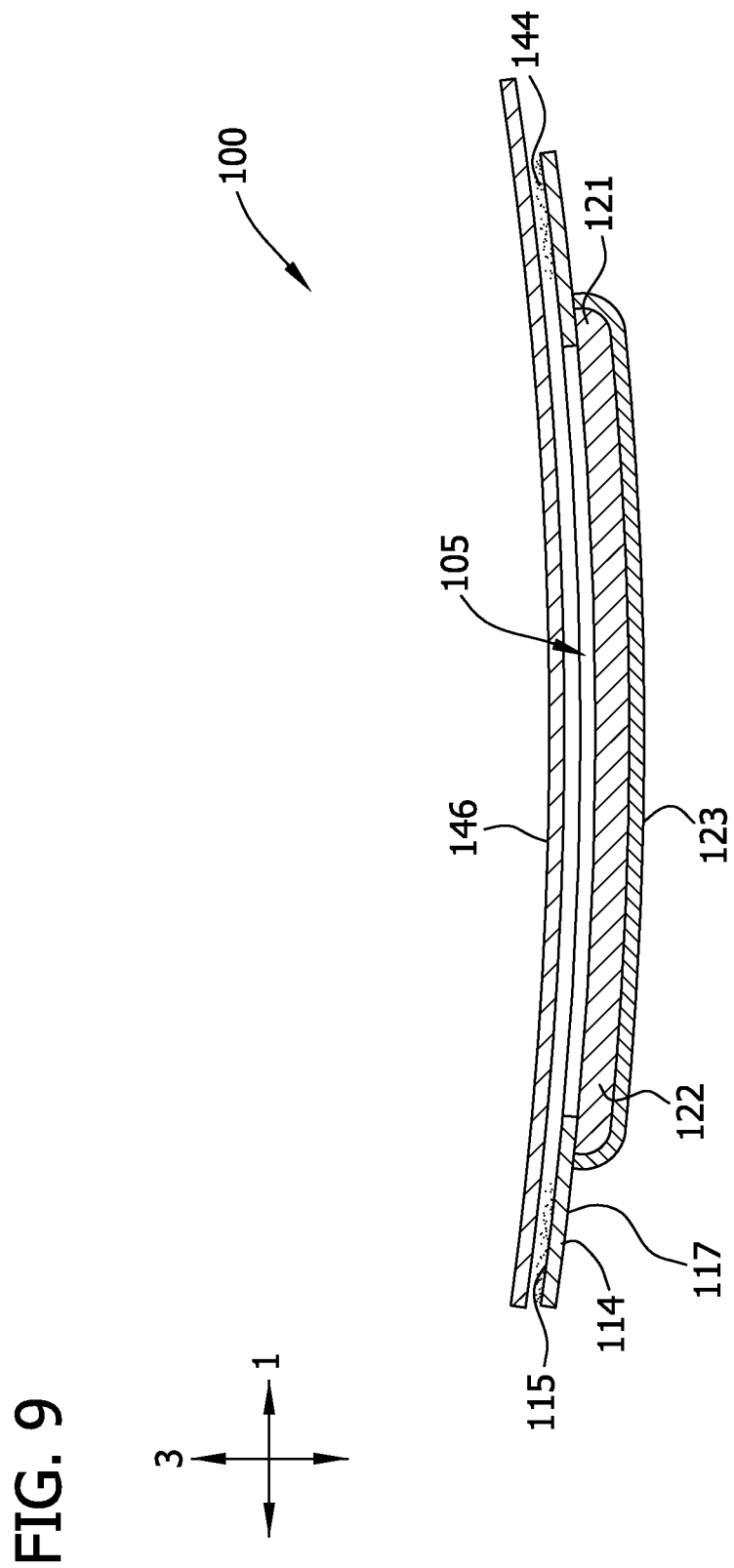

As is shown in FIGS. 8 and 9, to protect the body adhesive 144, a peel sheet or release sheet 146 may be used to prevent the body adhesive 144 from becoming contaminated, thus loosing its ability to stick to the body of a wearer and/or prematurely adhering to an unintended surface. Suitable materials for use as a peel strip 146 are well known in the art and are commercially available. Examples of suitable peel sheets or release sheets include, a silicone coated Kraft paper, a silicone coated film or the like. Other release coating includes coating containing polytetrafluoroethylene. The peel sheet or release sheet 146 may extend beyond one or both of the ends and/or sides of the shell, as shown in FIG. 9. Alternatively, the release sheet 46 may be sized to only cover the body adhesive on the first side 115 of the shell 114, as is shown in FIG. 8. In yet another embodiment of the present invention, the release sheet may extend beyond the adhesive at one or more locations, such as one of the ends or one of the sides of the shell 114 by providing the release sheet 146 with a tab (not shown) for the wearer to grasp to remove the release sheet 146 from the absorbent article 100 and the body adhesive 144 on the absorbent article 100. When the release sheet 146 extends beyond the adhesive, it is generally easier for the wearer to remove the release sheet 146 to place the absorbent article 100 for use.

Alternatively, the release sheet 146 may be provided with a pressure sensitive adhesive to hold the release sheet 146 in place when the absorbent article is devoid of an adhesive for body attachment. In this configuration, the release sheet 146 serves to protect the absorbent structure and first side of the shell from dirt and damage prior to use.

In another alternative, a release sheet may not be necessary. For example, the absorbent article may be rolled, folded onto itself or stacked upon each other. In these configurations, a release sheet is not needed. If rolled, the body adhesive 144 will generally contact the second side 117 of the shell 114 or the liquid impermeable backsheet 123 of the absorbent structure. The body adhesive 144 should releasably stick to one second side of the shell by readily releasing when unrolled by the wearer. In addition, the body adhesive 144 should not leave a residue on the second side 117 of the shell 114, of the backsheet 123. This should similarly occur when the absorbent articles 100 are stacked upon each other such that the body adhesive 144 of one article will attach the second side 117 of the shell and/or backing sheet of a second article. In another possible configuration, the absorbent article 100 may be folded along the longitudinal axis 1 of the lateral axis such that the body adhesive 144 in one area comes into contact with body adhesive in another area. In the folded configuration, the body adhesive should be selected such that the body adhesive will release from itself when manipulated by a wearer.

The dimensions and shape of the shell 114 should be such that it is appropriately sized for its intended use. The same is true for the size and shape of the absorbent structure 121 and the size of the opening 105. Generally, the size and shape of the absorbent structure 121 will dictate the size of the shell 114. The shape of the shell 114 is selected so that the absorbent article will have a comfortable feeling for the wearer, thereby providing protection against leaks and preventing the absorbent article from becoming dislodged from the body of the wearer during use. Generally, the shell 114 will be curved to fit the body of a wearer. The shell 114 also generally gives the absorbent article 100 its overall size and shape in the longitudinal 1 and lateral 2 directions. That is, the shell is generally longer and wider than the absorbent structure, as can be seen in the figures. In other words, the shell 114 will be wider in the lateral direction 2 than the absorbent structure 121, and the shell will be longer in the longitudinal direction 1 than the absorbent structure 121. As is mentioned above, it is possible for the absorbent structure 121 to be longer than the shell 114 but it is not generally wider.

When the absorbent article 100 is intended for use as a pantiliner, a sanitary napkin or a feminine incontinence article, the shell 114 should be wider and longer than the absorbent structure 121 attached to the second side 117 of the shell 114. The opening 105 in the shell 114 should generally be at least as wide and as long as the labia majora of the wearer. This will prevent the shell 114 from contacting the sensitive parts of a wearer's body. The absorbent structure 121 should be as large as or larger than the opening 105. As a result, to fit most women, the absorbent structure 121 is longer in the longitudinal direction 1 than it is wide in the lateral direction 2 of the absorbent structure. Generally, for most women, the labia majora are generally between about 40 mm and about 70 mm in width and between about 80 mm and 150 mm in length. Ideally, the absorbent structure 121 and opening 105 should be wider than the labia majora and slightly longer than the labia minora and slightly longer than or equal to the labia majora. Generally, the absorbent structure 121 and opening 105 should be between about 40 mm and 90 mm in width in the lateral direction 2 and between about 95 mm and about 150 mm in length in the longitudinal direction 1. The shape of the absorbent structure 121 and opening 105 will generally tend to be oblong and may be an oval, a rectangle, tear drop shaped, hourglass shaped or racetrack shaped. As can be seen in FIGS. 1 and 2, the absorbent structure 121 may be generally elliptical or oval in shape to match the size and shape of the vaginal area of most women.

Generally, the shape of the shell 114 may vary from a generally oval shape, as shown in FIGS. 2 and 4, to a shape which is a generally hourglass-like shape, shown in FIGS. 1 and 3. By a generally hourglass shape, it is meant shape in which the sides 119 of the shell 114 converge towards one another at a point along the longitudinal axis of the shell 114 to form a narrowest portion 133 of the absorbent article 100. Generally, the hourglass-like shape provides a cut-out for the wearer's legs. By having an hourglass-like shape, the shell 114 will not be attached to the legs of a wearer during use. This will provide more comfort for the wearer of the absorbent article 100. The shape of the shell 114 should be selected such that the absorbent article 100 will be comfortable to wear, while providing very effective leakage protection to the wearer. The shell 114 and the absorbent structure 121 should be able to adapt to the curvature of a wearers body during use. Other possible shapes for the shell 114 not specifically shown may also be used, provided that the shape will provide comfort to the wearer of the absorbent article.

To obtain an effective attachment of the absorbent article to the wearer, when the absorbent article is used as a sanitary napkin or an incontinence article, generally the width of the shell should be at least 10 mm on either side of the labia majora. Generally, the shell 114 of the absorbent article 100 will have a width, in the lateral direction 2, between about 50 mm up to 200 mm or more. Typically, the shell will be between about 60 and 120 mm at its narrowest point. This will allow the shell 114 to have a first side 115 that can be effectively attached to the skin of a wearer on either side of the labia majora.

In addition, the absorbent article 100 may also be configured to have an anterior region 164, a central region 165 and a posterior region 166, as is shown in FIG. 1. As used herein, the term "anterior" refers to the direction towards the front of the wearer during use. As used herein, the term "posterior" refers to the direction towards the back of the wearer during use. A particular embodiment is shown in FIG. 1 of an absorbent article having a configuration designed to fit specific areas of the vulva region of a wearer. By providing specific portions for attachment to specific areas of the body of the wearer, the absorbent article may be configured to better fit the body of the wearer. The anterior region 164 of the absorbent article will be the portion of the absorbent article between the absorbent structure 121 and the first end 161 of the absorbent article 100. The posterior region 166 of the absorbent article 100 will be the portion of the absorbent article between the absorbent structure 121 and the second end 162 of the absorbent article 100. Generally, the posterior region 166 will be designed to be placed between the vagina area and the anal area of the wearer. The anterior region 164 is designed to be placed on the mons Veneris region of a female wearer. The central region 165 of the absorbent article 100 is designed to cover the vagina area of the wearer and the skin area surrounding the lateral sides of the labia majora, when the absorbent article is used as a pantiliner, sanitary napkin or an incontinence article. In an alternative use, the absorbent article of the present invention may also be used as an underwear replacement, or a guard for a swimming suit.

Figure 10:
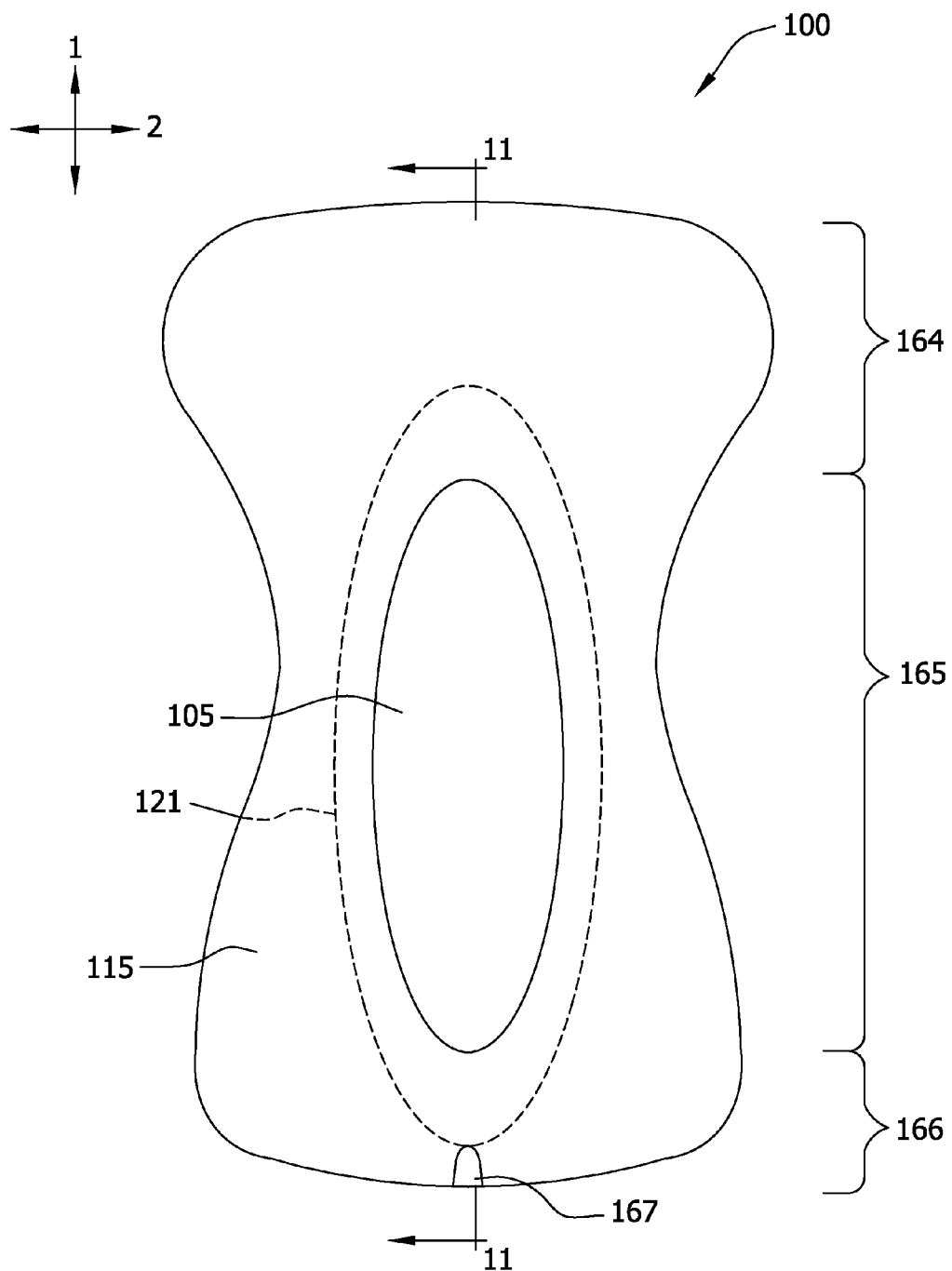
FIG. 10 shows a top view of another absorbent article of the present invention having a design for attachment to specific area of the body.
Figure 11:
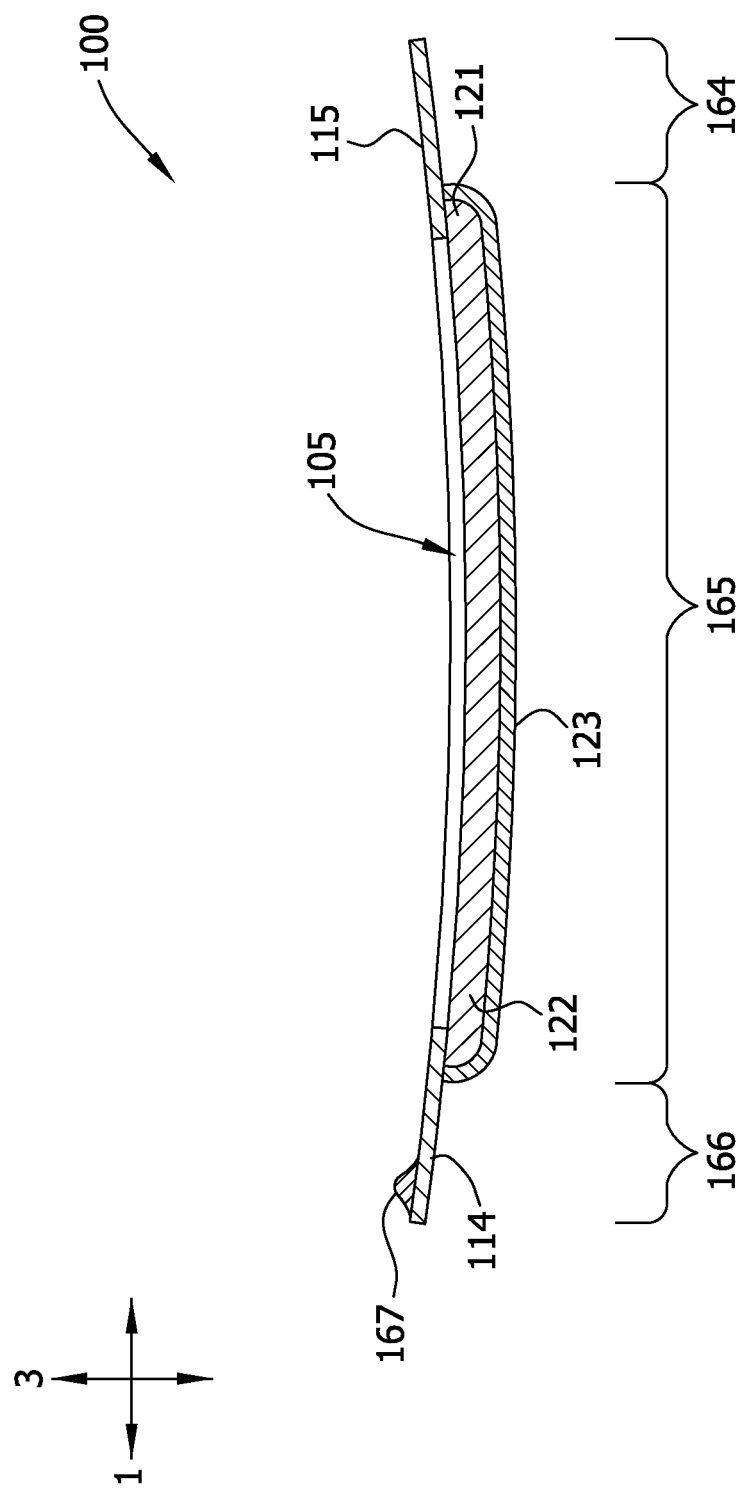
FIG. 11 shows a cross-section view of FIG. 10 along lines 11-11.

To obtain an effective attachment to the body of the wearer, the shell 114 can be configured to be anatomically correct for a wearer. As is shown in FIG. 10, the shape of the absorbent article 100 is such that it will correctly and securely fit in the vulva region of a wearer. The general shape of the absorbent article shown in FIG. 10 has been found to effectively attach to the vulva region of female wearers of the absorbent article. Additional features may be included to ensure an anatomically correct shape. For example, in the posterior region of the absorbent article 100, more particularly, the posterior region of the shell on the first side 115, the shell 114 may be imparted with a three-dimensional protrusion 167, as shown in FIGS. 10 and 11. The protrusion 167 acts to fit comfortably in the perinea region of the wearer. The protrusion 167 may be formed from the shell material or may be formed from the body adhesive 144. By providing the three-dimensional protrusion 167, the absorbent article 100 can effectively fit to the typical body shape of the female wearer, thereby preventing leaks form the posterior region of the absorbent article. The protrusion 167 may also serve as a guide to the wearer in placement of the absorbent article 100 on the body of a wearer prior to use.

Figure 12:
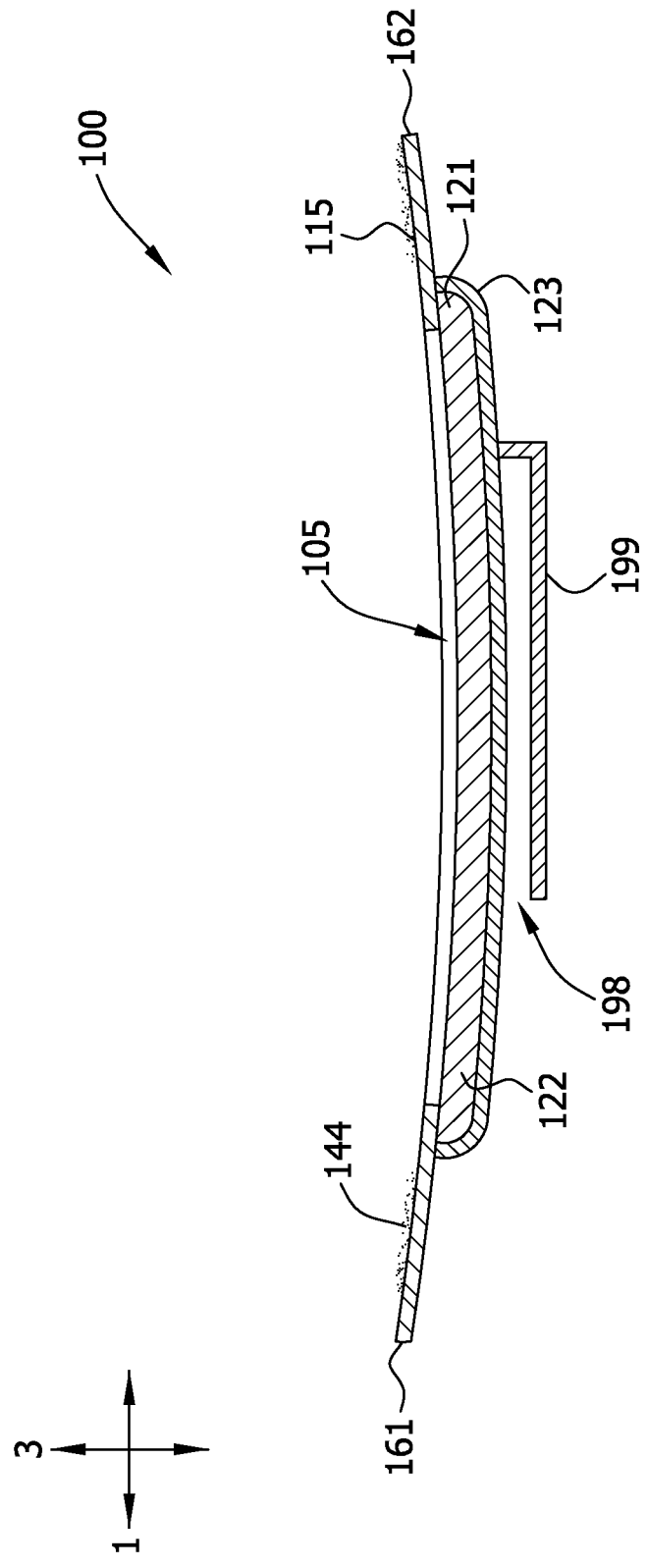
FIGS. 12 and 13 show embodiments of the present invention with placement guides.
Figure 13:
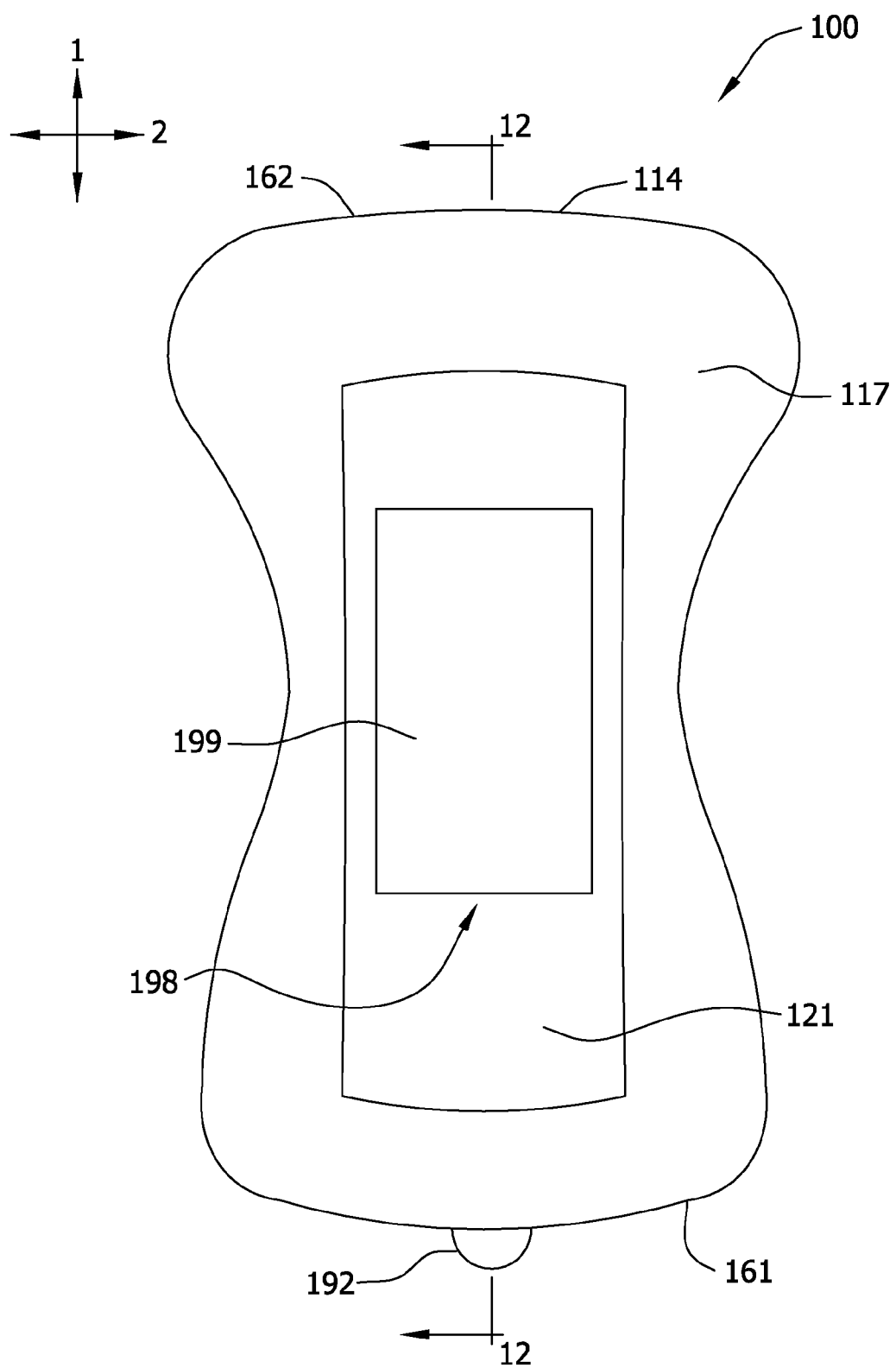
Figure 14:
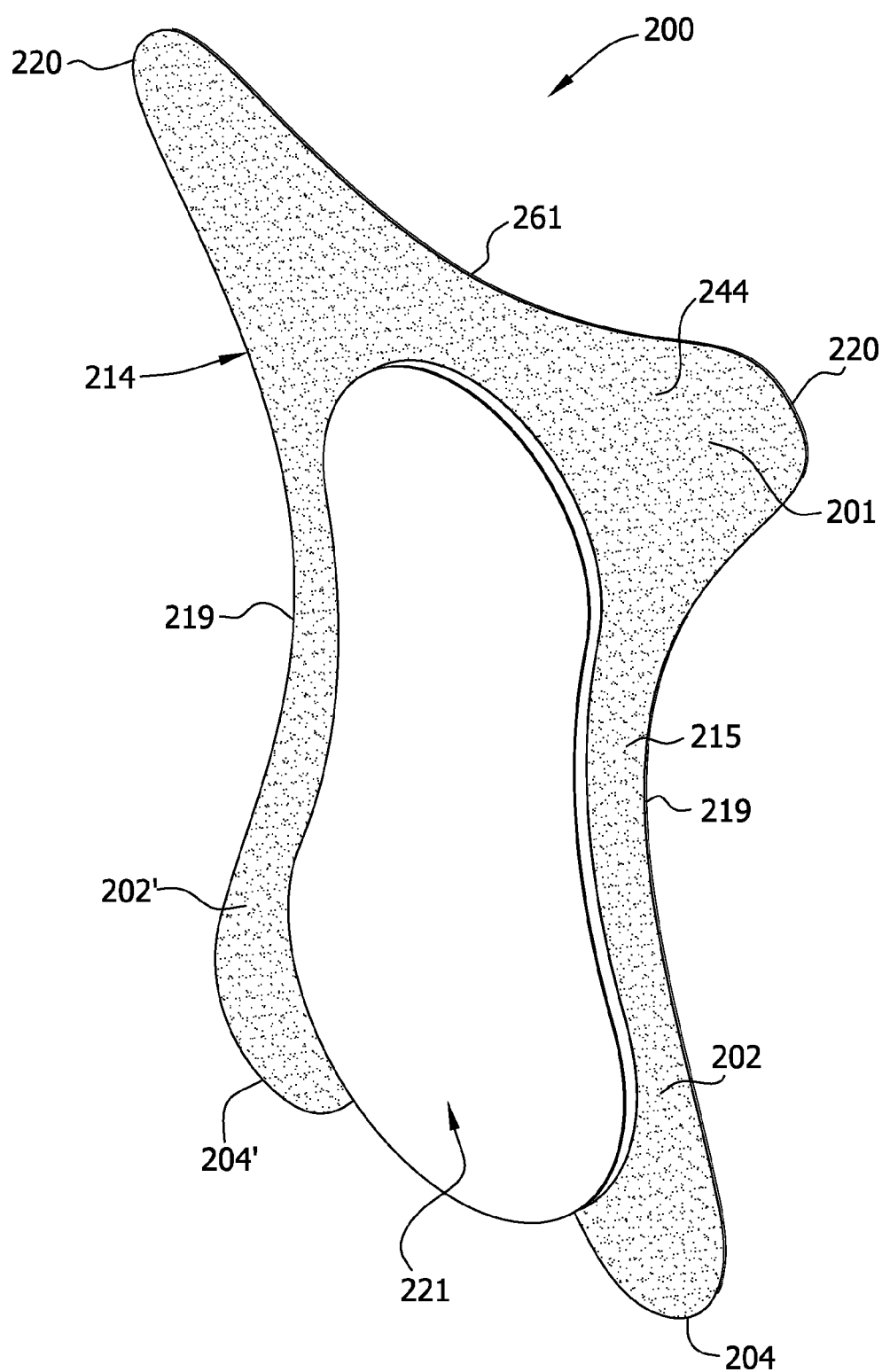
FIG. 14 shows a perspective view of another embodiment of an absorbent article of the present invention.
Figure 15:
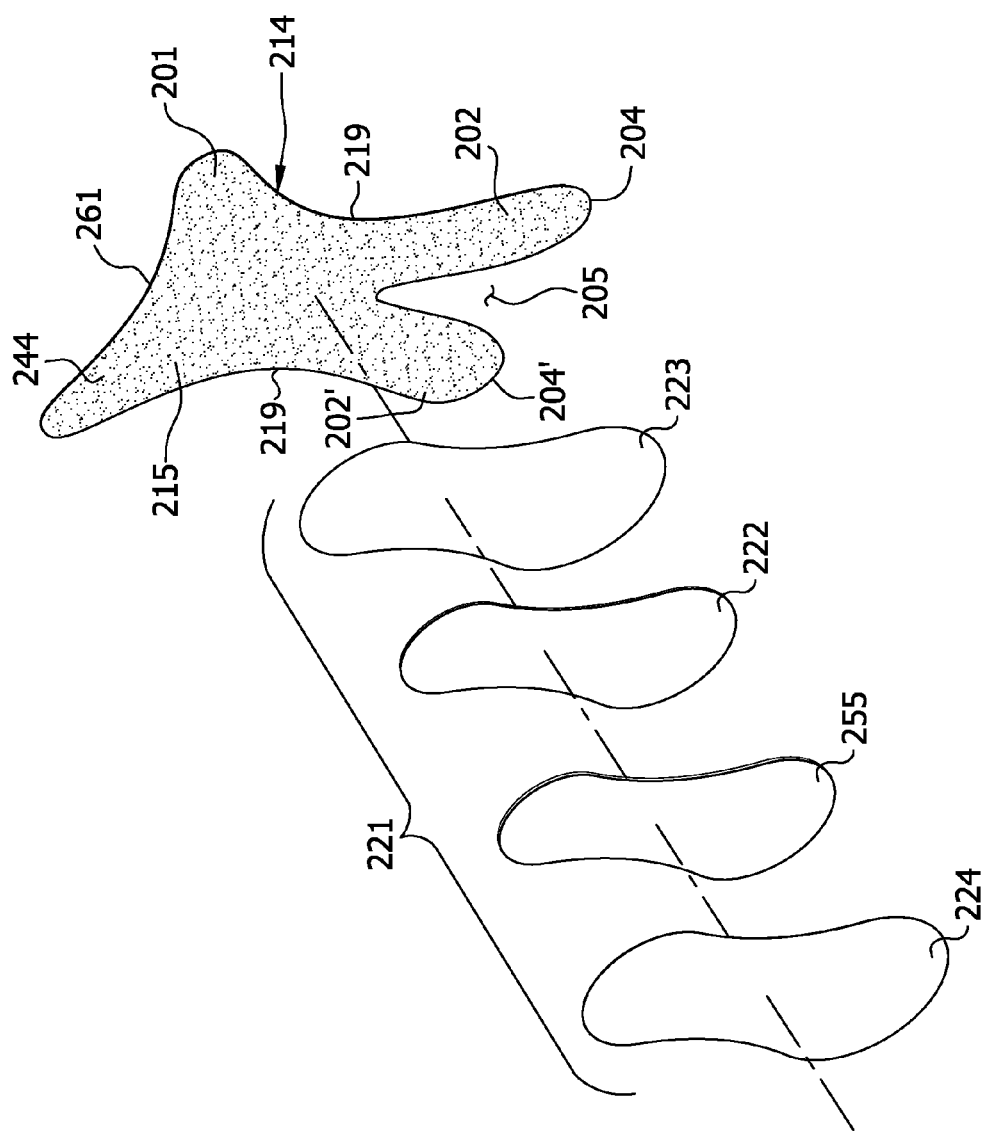
FIG. 15 shows an exploded perspective of the absorbent article.

The absorbent article 100 of the present invention may have other features which aid the wearer to place and remove the absorbent article from the body. As is shown in FIGS. 12 and 13, the second side 117 of the shell 114 or the backsheet 123 may be provided with positioning aids such as a finger pocket 199, shown in FIG. 12, or finger grooves in the shell 114 (not shown) material or backsheet 123 of the absorbent structure 121 as is shown in FIG. 12. Generally, the finger pocket 199 has an opening 198 positioned such that a wearer inserts their fingers towards the posterior region 166 or second end 162 of the absorbent article 100. The pocket 199 gives the wearer a location to place her fingers during placement of the absorbent article 100 onto the wearer's body. The pocket 199 may be an opening wide enough for the wearer to place at least two fingers in the pocket. Alternatively, there may be two or more openings which allow the wearer to place only one finger in each opening. Other similar positioning aids may be used to help guide a wearer to properly place the absorbent article for use. For example, grooves may be placed in the second side 117 of the shell 114 or backsheet 123 of the absorbent structure. This may allow the wearer to feel the location of the absorbent structure relative to the vulva region during application of the absorbent article 100 to the vulva region of the body. The pocket 199 may also assist the wearer in removing the absorbent article from their body or removing the absorbent structure when it needs to be replaced.

The absorbent article 100 may also be provided with a removal aid which provides the wearer with an easy way to grasp and remove the absorbent article applied to the body. One particular removal aid is shown in FIG. 13 including a tab 192 located on the first end 161 of the shell which is not adhered to the body or is devoid of adhesive. Alternatively, other removal aids, such as having an area of the first end 161 being devoid of the body attaching adhesive 144 may be used. Other types of removal aid which may be present include loops and pull strings. The removal aid allows the wearer to effectively begin the process of gently removing the absorbent article from the body of the wearer, without the need of having to find a portion of the shell which may not be completely attached.

Other features or additives may be incorporated into the absorbent article of the present invention. For example, the absorbent article may contain an odor control agent, or a fragrance, skin wellness agents and other similar additives used in currently available absorbent articles. Any odor control agent or fragrance known to those skilled in the art may be used in the absorbent article 100 of the present invention. The odor control agent or fragrance may be added in various components of the absorbent article, including the shell 114, the absorbent structure 121, or the body adhesive 144. Skin wellness additives may be added onto the absorbent structure, any portion of the first surface 115 of the shell 114 attached to the wearer or in the body adhesive 144.

Generally, to apply the absorbent article 100 to the body of a wearer, the release sheet 146, protecting the absorbent structure and adhesive, if present, is removed from first surface of the shell. Next, the wearer positions the absorbent structure of the portion of the body in which absorbency is needed. If positioning pockets or other positioning aids are present on the absorbent structure, the wearer may optionally use these positioning aids to properly place the absorbent article for use. In the case of sanitary napkins and incontinence absorbent articles for females, the absorbent is positioned over the vagina area such that the absorbent structure will absorb body fluids. The wearer then checks to ensure that the first region 101 of the shell or the adhesive 144, if present, is contacting the skin around the vagina area.

If the absorbent article is intended to have a front and a back portion, the wearer first identifies the anterior region 164 and/or the posterior region 166 of the absorbent article. To aid in identification of the anterior and posterior regions, indicia located on the release sheet 146, shell 114 or absorbent structure 121 viewable through the opening 105 in the shell 114 to indicate the anterior region and/or posterior region of the absorbent article may be present. Indicia can be simply lettering or a picture to indicate the front or back of the absorbent article. Once the anterior region and posterior region are identified by the wearer, the wearer places the absorbent article in the same manner described above. Examples of indicia which may be used include, color, wording, diagrams and the like, which would indicate to a wearer the anterior and posterior regions of the absorbent article.

In each case, the absorbent structure, which is designed to cover the labia majora of the wearer, may be positioned with the aid of the absorbent structure 121 or the opening 105. More specifically, the absorbent structure and/or the opening, when sized and shaped to the approximate size of the labia majora, can serve to guide the placement of the absorbent structure 121 over the labia majora. Once properly placed, pressure is applied by the wearer to the second side 117 and or backsheet 123 of the shell which will allow the first surface of the shell to contact the skin of the wearer, or to allow any adhesive applied to the first surface to be applied to the skin of the wearer.

By having the absorbent article 100 attached to the body of a wearer, the absorbent article 100 will tend to move with the skin of the wearer. This results in a comfortable to wear absorbent article which will be less likely to leak than conventional absorbent articles. The absorbent article has a very close-to-the-body fit which may provide improved discretion for the wearer.

Other benefits of the absorbent article 100 of the present invention may also be provided. For example, when the first side 115 of the shell has an adhesive applied thereto, upon removal of the absorbent article after use, the wearer may fold the first side of the shell onto itself to dispose of the used absorbent article. An effective seal may be formed around the perimeter of the shell, thereby effectively encapsulating the absorbent structure within a closure and the backing sheet of the absorbent layer. As a result, any odors associated with the absorbed fluids will be contained within the shell material and backing layer. Another use of the absorbent article of the present invention is a tampon backup absorbent article. The absorbent article could be effective in hiding the withdraw string of a tampon, while providing additional leakage protection.

The absorbent article described above can be an individual absorbent article or may be part of an absorbent system, offering the wearer a wide variety of options to fill the needs of the wearer. For example, the shell could be provided to wearers in a variety of shapes or sizes to allow wearers to select the appropriate shape or size for their given body shape. Likewise, the body adhesive may be provided in a variety of adhesive strengths to match the adhesive strength needed or desired by the wearer. By providing a variety of adhesive or other attachment means, a wearer could select the shells to match body type, body condition and other various factors that may vary from one wearer to another. Similarly, the absorbent structure could be provided in various absorbent capacities so that the wearer could select the appropriate absorbency to match the wearer's needs.

The absorbent system may be provided to wearers in a variety of packaging arrangements. In one packaging arrangement, a plurality of shells having different properties may be provided in separate packages or could be provided in a single package. It is generally a better packaging arrangement if shells having similar properties, shapes or sizes are provided in a single package. That is, in a given package, the wearer is provided with a plurality of shells all having the same shape, size, and properties, such as the body attachment properties. Regarding the absorbent structures, the absorbent structures could be provided to the wearer in packages sorted by absorbent capacity or various absorbent capacity structures could be provided in a single package. By having all absorbent structures in a single package with a single absorbent capacity, a wearer is able to select the correct absorbent capacity for their typical needs. However, by providing different absorbent capacity absorbent structures in a single package, the wearer will be provided with the ability to select the absorbent structure with the appropriate absorbent capacity for a given situation, without the need to purchase multiple packages of absorbent structures.

Figure 16:
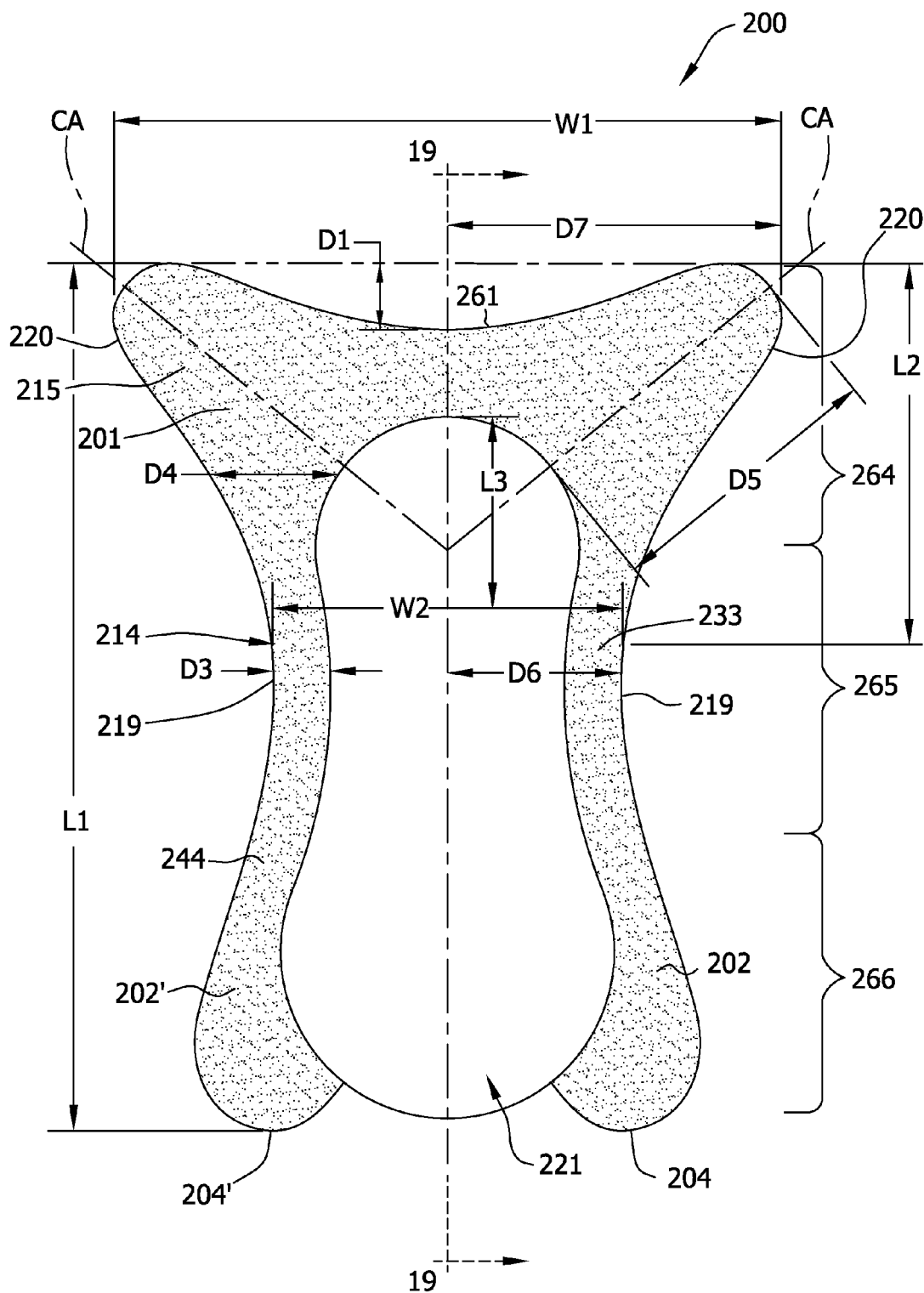
FIG. 16 shows a top view of the absorbent article.
Figure 17:
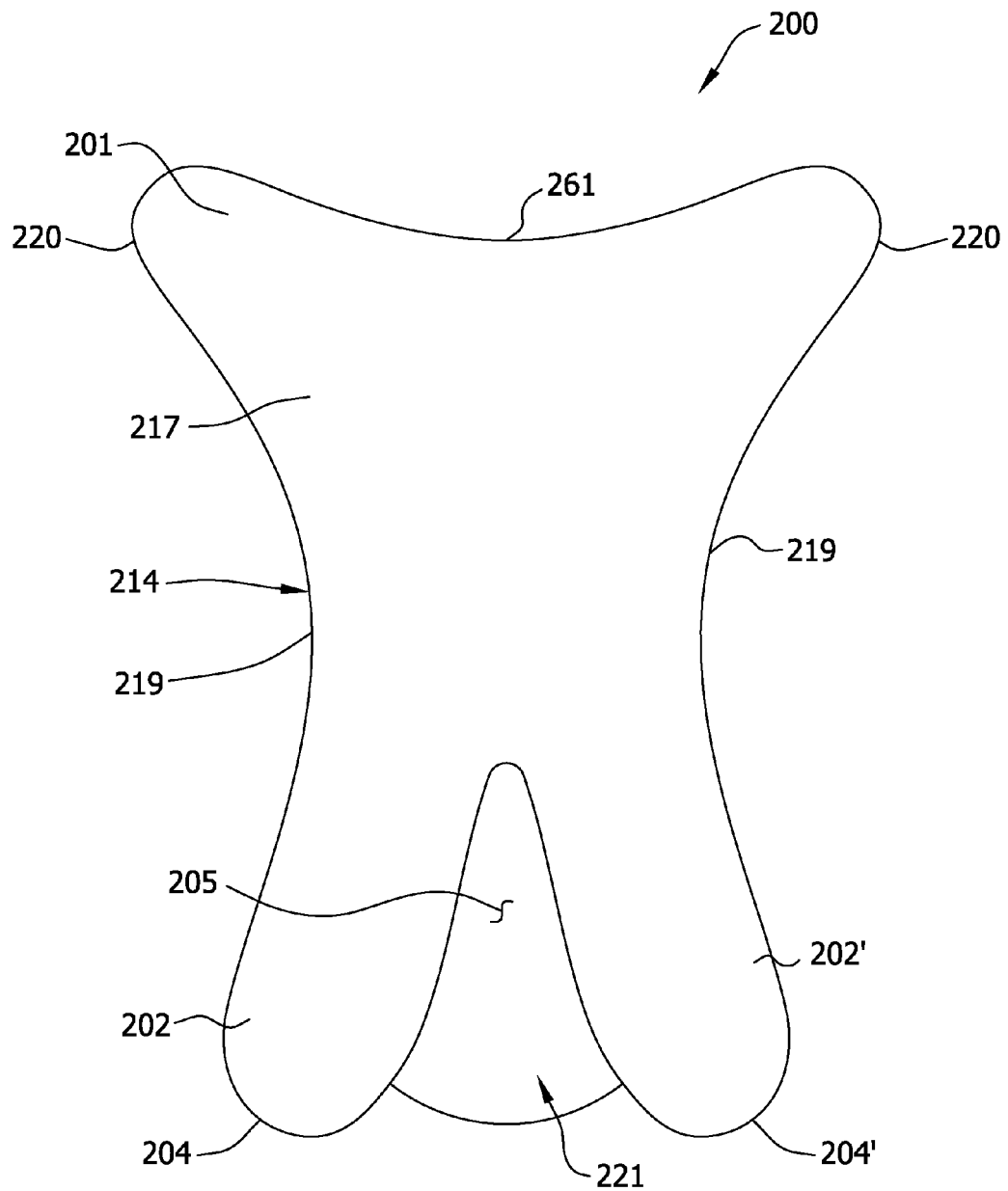
FIG. 17 shows a bottom view of the absorbent article.

In another embodiment, a body adhesive absorbent article 200, which is illustrated in FIGS. 14-21, also comprises a shell 214 and an absorbent structure 221 and has a longitudinal axis X and a transverse axis Y. The shell 214 has a first region 201, a pair of lateral side regions 202, 202' extending from the first region, and an opening 205 (FIG. 15) extending longitudinally at least in part between the side regions. The shell 214 also has a first side 215, which defines a body-facing surface (FIG. 14), and a second side 217, which defines a garment-facing surface (FIG. 17). In the illustrated embodiment, the first side 215 of the shell 214 has a body adhesive 244 on at least a portion thereof for adhering the absorbent article 200 directly to the wearer's skin, and particularly, to a female wearer's skin surrounding her vulva region for the illustrated absorbent article. The body adhesive 244 contacts the skin and hair, if present, in the vulva region and possibly the pubic region and/or the perinea region of the wearer's body, thereby supporting and holding the shell 214 and absorbent structure 221 against the body of the wearer during use. A peel sheet or release sheet (not shown) may be used to prevent the body adhesive 244 from becoming contaminated, thus losing its ability to stick to the body of the wearer and/or prematurely adhering to an unintended surface.

Generally, the size and shape of the absorbent structure 221, depending on its intended use, will dictate the size of the shell 214. The shape of the shell 214 is selected so that the absorbent article 200 will have a comfortable feeling for the wearer and inhibit the absorbent article against becoming detached from the body of the wearer during use thereby providing protection against leaks. In one suitable embodiment, the absorbent article 200, including the shell 214 and absorbent structure 221, is dimensioned and shaped to fit approximately 75 percent of adult females. It is understood, however, that the absorbent article 200 can be dimensioned and shaped to fit more or fewer females. It is also contemplated that different sizes of the absorbent article 200 may be provided to accommodate a greater percentage of females.

With reference to FIG. 16, the absorbent article 200 (and hence the shell 214) can be suitably divided into three general longitudinal regions: an anterior region 264, a posterior region 266 and a central region 265 extending longitudinally between and interconnecting the anterior and posterior regions. Each of these regions 264, 265, 266 is sized and shaped for alignment with different body regions of a wearer of the absorbent article. More specifically, the anterior region 264 of the article 200 is adapted to be disposed adjacent the wearer's lower abdomen region. The central region 265 is adapted to be disposed between the upper thigh region of the wearer to cover the wearer's perineum region and vaginal region. The posterior region 266 of the article 200 is adapted to be disposed in the gluteal region of the wearer.

In the illustrated embodiment, the anterior region 264, the central region 265, and the posterior region 266 of the absorbent article 200 are of roughly equal length, with each region corresponding generally to about ⅓ of a total length L1 of the absorbent article 200. The length L1 is defined herein as the longitudinal distance from a longitudinally outermost extent of the article 200 (and in the illustrated embodiment, the shell 214) in the anterior region 264 to a longitudinally outermost extent of the article (and in the illustrated embodiment, the shell) in the posterior region 266. As an example, the length L1 of the shell 214 (and hence the absorbent article 200 in the illustrated embodiment) may suitably be in the range of about 170 mm to about 220 mm, and more suitably in the range of about 190 mm to about 200 mm. As an additional example, the absorbent article 200, and more particularly the shell 214, has a length L1 of about 194 mm. It is understood that the absorbent article 200 may have a length L1 different that those set forth above without departing from some aspects of this invention. It is also contemplated that two or all three of the article regions 264, 265, 266 may instead be of unequal lengths depending on the desired fit and the intended body placement of the article without departing from the scope of this invention.

The absorbent structure 221 of FIGS. 14-21 is suitably adhered to the first side (i.e., body-facing surface) 215 of the shell 214 and is sized and located relative to the shell such that the shell extends both longitudinally and transversely outward beyond the periphery of the absorbent structure in at least the anterior region 264 and the central region 265, and more suitably in at least a portion of the posterior region 266 as well. The absorbent structure 221 is offset longitudinally, i.e., not centered lengthwise on the transverse or lateral axis of the absorbent article, such that the shell 214 extends longitudinally outward beyond the absorbent structure a greater distance in the anterior region 264 of the article 200 than in the posterior region. It is understood, though, that the absorbent structure 221 may be longitudinally centered so that the shell 214 extends equally longitudinally outward beyond the absorbent structure, or may be offset longitudinally toward the anterior region 264 so that the outward longitudinal extension of the shell beyond the absorbent structure is greater in the posterior region 265 than in the anterior region without departing from the scope of this invention.

As illustrated in FIG. 16, the anterior region 264 of the absorbent article 200 comprises the first region 201 of the shell 214 and includes a portion of the absorbent structure 221. Since much of the first side (i.e., body-facing surface) 215 of the shell 214 is exposed (i.e., not covered by the absorbent structure 221) in the anterior region 264 of the absorbent article 200, a relatively large surface area of the first side of the shell has body adhesive 244 applied thereto for adhering the shell, and hence the absorbent article, to the wearer.

A first end 261 of the absorbent article 200, and more particularly a longitudinal edge of the anterior region 264 defining this first end of the absorbent article 200, is suitably contoured along the width of the shell at this first end to accommodate the lower abdomen region of the wearer. In the illustrated embodiment, for example, the longitudinal extent (e.g., length) of the shell 214 relative to the transverse axis of the article is non-uniform across the width of the shell at the first end 261 of the article, and more suitably increases as the shell extends transversely outward from the longitudinal axis of the article to transversely, or laterally opposite sides 219 of the article and more particularly laterally opposite side edges of the shell. Accordingly, a greatest longitudinal extent of the shell 214 is generally adjacent the intersection of the longitudinal end 261 with the respective sides 219 of the article (i.e., the shell in the embodiment of FIG. 16). More suitably, the longitudinal edge of the shell 214 (i.e., at first end 261 of article 200 in the illustrated embodiment) is generally arcuate as it extends across the width of the shell at its longitudinal edge. It is understood, however, that the contour of the longitudinal edge of the shell 214 in the anterior region 264 of the article may be V-shaped, U-shaped or other suitable shape without departing from the scope of this invention.

The contoured longitudinal edge of the shell 214 (i.e., first end 261 of the article 200 in the illustrated embodiment) thus broadly defines a recess in the anterior region 264 of the article (and thus of the shell in this instance). This recess defines a longitudinal distance D1 between the longitudinally outermost extent of the longitudinal edge of the shell 214 in the anterior region 264 and the longitudinal extent of the longitudinal edge of the shell at the longitudinal axis of the article 200 in the anterior region. In one suitable embodiment, the distance D1 of the recess is in the range of about 5 mm to about 35 mm, and more suitably about 12 mm to about 18 mm. As one example, the distance D1 of the recess at the anterior region 264 in the embodiment of FIG. 16 is approximately 15 mm.

The sides 219 of the illustrated article 200 are suitably defined by transversely opposite side edges of the shell 214. These side edges of the shell 214 are contoured so that the overall width of the article 200 (i.e., the distance between the transversely opposite sides 219 thereof), and more particularly the width of the shell in the illustrated embodiment, is non-uniform along the length L1 of the article to define leg cutouts for accommodating the upper thighs of the wearer. In one suitable embodiment, the width of the article 200 and hence the shell 214 increases from a narrowest width W2 in the central region 265 of the article toward each of the longitudinally opposite ends (261 and 204, 204') of the article. Still more suitably, the width of the article 200 and more suitably the shell 214 is also greater in the anterior region 264 of the article than in the posterior region 266. In the illustrated embodiment, for example, a greatest width W1 of the article 200 is defined by the transverse side edges of the shell 214 adjacent the longitudinal edge of the shell (e.g., first end 261 of the article 200) in the anterior region 264 of the article. As additional examples, the greatest width W1 of the article 200 and more particularly the shell 214 is in the range of about 52 mm to about 180 mm and more suitably about 140 mm to about 170 mm. In the illustrated embodiment of FIG. 16, the greatest width W1 of the article 200 is approximately 150 mm. The narrowest width W2 of the article 200 and more particularly the shell 214 is in the range of about 45 mm to about 85 mm, and more suitably about 60 mm to about 80 mm. In the illustrated embodiment, for example, the narrowest width W2 of the shell 214 is approximately 78 mm. In other embodiments, a ratio of the length L1 of the shell 214 (and hence the article 200 in the illustrated embodiment) to the narrowest width W2 of the shell 214 (and hence article 200) is in the range of about 3 to about 1, and more suitably about 2 to about 1.

In the article 200 illustrated in FIG. 16, the sides 219 of the article 200 and more particularly the transverse side edges of the shell 214 are generally arcuate along substantially the entire length L1 of the article. Alternatively, the sides 219 may be arcuate along only a portion of the length L1 of the article. It is also understood that the sides 219 defining the leg cutouts may be V-shaped, U-shaped or other suitably shape, or they may be uniform (e.g., straight or longitudinal) along substantially the entire length L1 of the article 200. It is also understood that the sides 219 of the article may be contoured to define article 200 widths other than those set forth above without departing from the scope of this invention. It is further understood that the greatest width of the article 200 may be other than in the anterior region 264, and/or the narrowest width may be other than in the central region 265 of the article and remain within the scope of this invention.

Still referring to FIG. 16, the contoured longitudinal edge of the shell 214 (e.g., first end 261 of the article 200) at the anterior region 264, together with the contoured transverse side edges of the shell (e.g., article sides 219) where these side edges generally intersect the longitudinal edge of the shell, define a pair of transversely spaced tabs 220 in the anterior region. Each tab 220 has a central axis CA extending in part transversely outward of the shell 214 and in part longitudinally outward of the shell. Each of the tabs 220 suitably has body adhesive 244 on the body-facing surface (e.g., first side 215) for adhering the tabs directly to the wearer and more suitably to the abdomen region of the wearer. In one particularly suitable embodiment, the tabs 220 are sized to extend to a region of the wearer that has little or no pubic hair to facilitate better adherence to the wearer's skin. For example, in one embodiment each of the tabs 220 extends outward along its central axis CA away from the peripheral edge of the absorbent structure 221 a distance D5 in the range of about 20 mm to about 90 mm, and more suitably about 45 mm to about 70 mm. Each tab 220 also has a transversely outermost extent (which in the illustrated embodiment defines the greatest width W1 of the shell 214 and hence the article 200) defining a distance D6 from the longitudinal axis of the article to the transversely outermost extent of a respective one of the tabs (which is approximately half of the width W1 of the shell). In a particularly suitable embodiment, a ratio of the distance D6 (that the tab 220 extends transversely outward) to the distance D5 (the length of the tab along its central axis CA) is in the range of about 1 to about 2. In another suitable embodiment, a ratio of the distance D6 to a distance between the longitudinal axis of the shell 214 and a side edge of the absorbent structure 221 (i.e., about half of the width W5 shown in FIG. 21) is in the range of about 2 to about 5.

Each of the tabs 220 further has a longitudinally outermost extent (which in the illustrated embodiment defines the outermost extent of the longitudinal edge of the shell 214) in the anterior region 264 defining a length L2 from the transverse axis of the shell 214 to the longitudinally outermost extent of the tab 220. This length L2 is suitably in the range of about 50 mm to about 120 mm, and more suitably about 70 mm to about 100 mm. As illustrated in FIG. 16, the absorbent structure 221 extends longitudinally into the anterior region 264 of the article and has a longitudinally outermost extent defining a length L3 from the transverse axis to the longitudinally outermost extent of the absorbent structure in the anterior region. For example, this length L3 may suitably be in the range of about 30 mm to about 90 mm, and more suitably about 50 mm to about 70 mm. In another embodiment, a ratio of the length L2 (the longitudinally outermost extent of the tabs 220) to the length L3 (the longitudinally outermost extent of the absorbent structure 221 in the anterior region 264) is in the range of about 3 to about 1 and more suitably about 2 to about 1.

Figure 20:
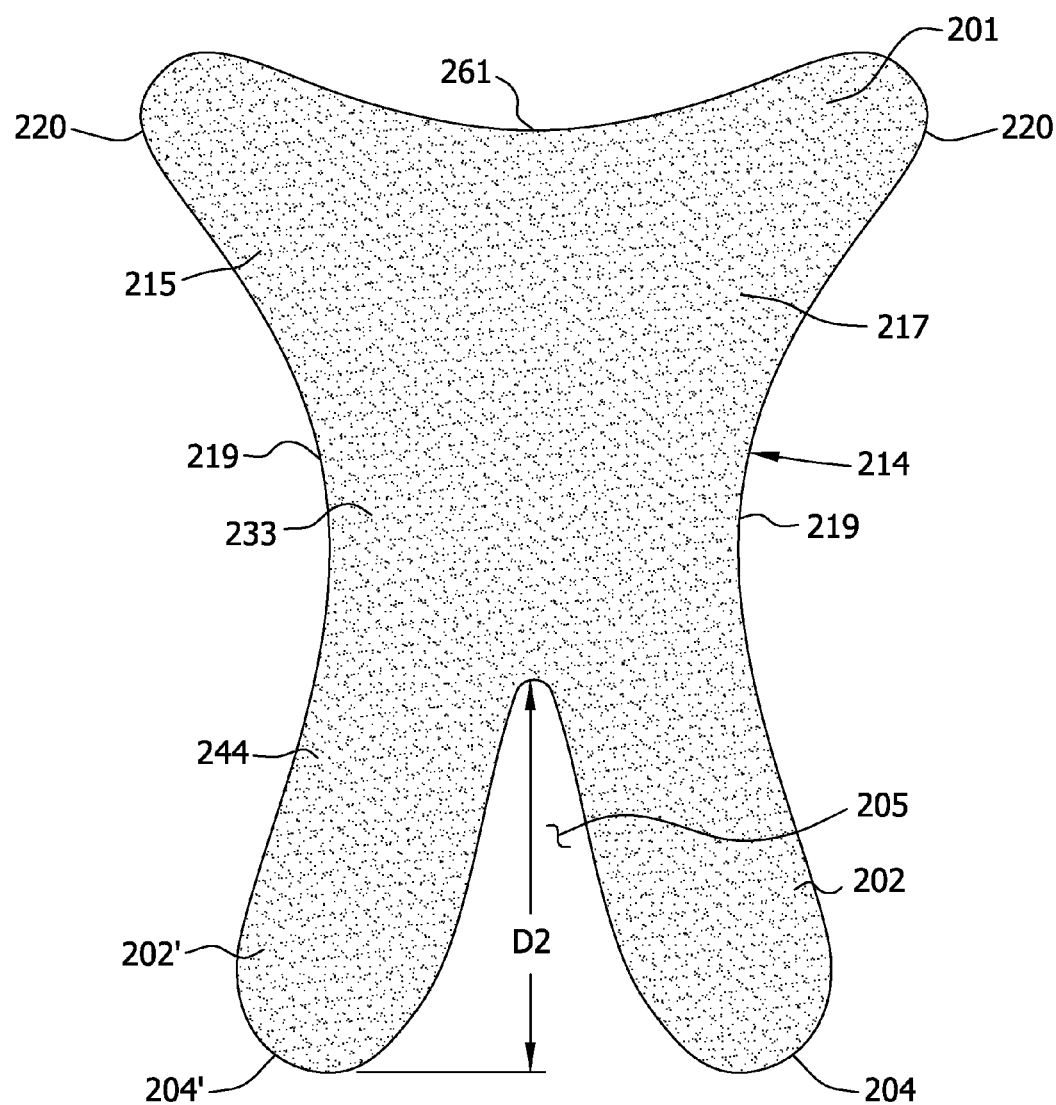
FIG. 20 shows a top view of a shell of the absorbent article.

With reference now to FIGS. 16 and 20, the posterior region 266 of the absorbent article 200 includes the opening 205 in the shell 214 with portions of the lateral side regions 202, 202' broadly defining a pair of transversely spaced tabs disposed on opposite sides of the opening. The posterior region 266 disposition of these tabs is such that the tabs are aligned generally with the buttocks of the wearer rearward of the perineal region. In the illustrated embodiment, the opening 205 is in the form of a generally V-shaped ingress extending longitudinally on the longitudinal axis of the article 200 such that the tabs are free to flex relative to the central region 265 of the article and generally independent of each other to accommodate normal movement of the wearer's thighs and buttocks. In one particularly suitable embodiment, the ingress 205 extends longitudinally inward from the distal end 204, 204' of the absorbent article 200 (and more particularly a greatest longitudinal extent of the shell in the posterior region 266) a distance D2 in the range of about 5 mm to about 100 mm, and more suitably about 50 mm to about 80 mm. In the illustrated embodiment, for example, the ingress 205 has a distance D2 of about 75 mm. In another embodiment, the distance D2 of the ingress 205 is in the range of about 5 percent to about 60 percent of the length L1 of the shell 214, and more suitably about 25 percent to about 40 percent of the length L1. In other embodiments, a ratio of the distance D1 of the recess in the anterior region 264 of the shell 214 to the distance D2 of the ingress 205 in the posterior region 266 is in the range of about 4 to about 1, and more suitably between about 3 and about 1. In still another embodiment, a ratio of the distance D1 of the recess in the anterior region 264 of the shell 214 to the total length L1 of the shell is suitably in the range of about 0.03 to about 0.2 and more suitably in the range of about 0.06 to about 0.09. It is understood, however, that the ingress 205 can be larger or smaller without departing from some aspects of this invention.

Figure 18:
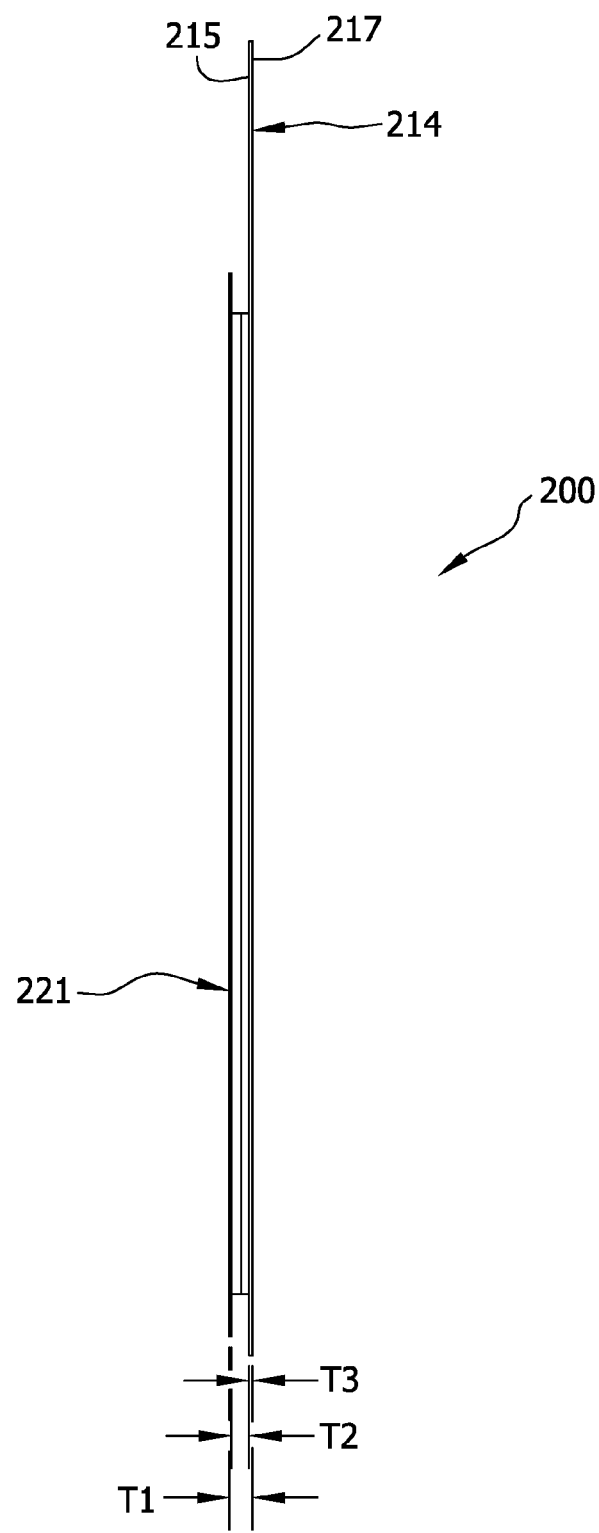
FIG. 18 shows a side view of the absorbent article.
Figure 19:
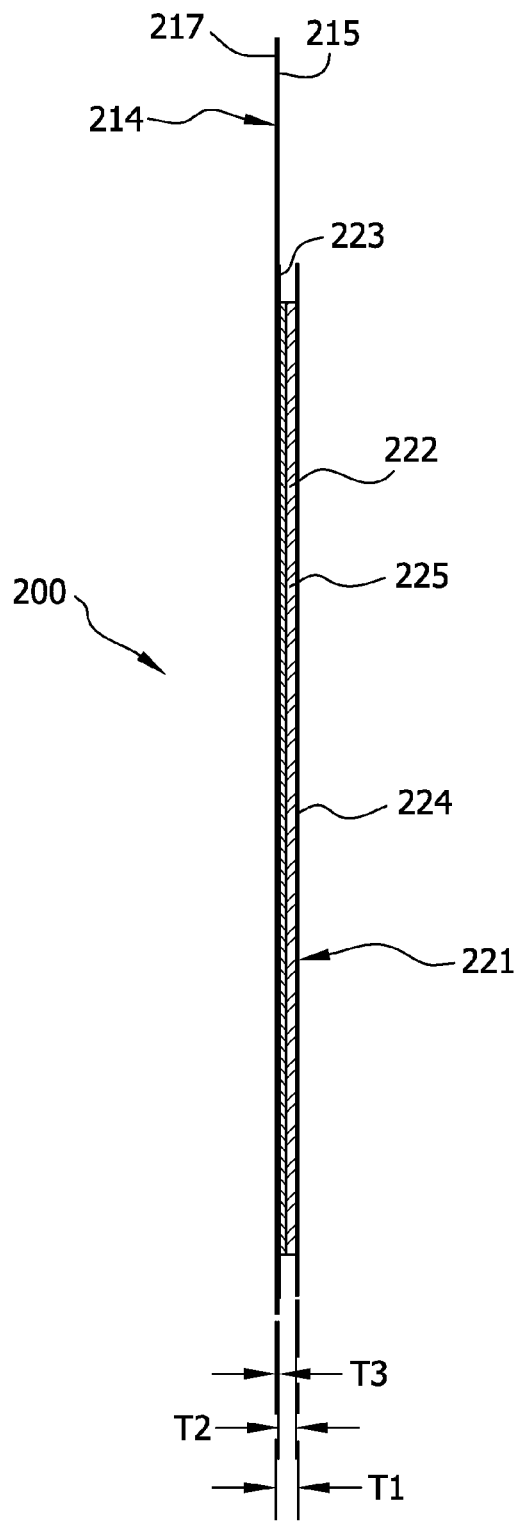
FIG. 19 shows a side cut-away view of the absorbent article taken along line 19-19 of FIG. 16.

Turning now to FIGS. 18 and 19, the absorbent structure 221 can comprise a single layer structure or be constructed of multiple layers. The illustrated absorbent structure 221, for example, comprises an absorbent core 222, an intake layer 225, a top sheet 224, and a liquid impermeable backsheet 223. A total thickness T1 of the absorbent article 200 is suitably in the range of about 1 mm to about 12 mm, and more suitably about 2.5 mm to about 5 mm. As one example, the thickness T1 of the illustrated absorbent article is approximately 3.5 mm. It is understood, however, that the thickness T1 may be other than as set forth above depending at least in part on the intended use of the absorbent article 200. For example, an absorbent article 200 in which the absorbent structure 221 is intended to be used in the manner a maxi-pad may have a greater thickness T1 than an absorbent article in which the absorbent structure is to be used in the manner of a panty-liner. In another suitable embodiment, the absorbent structure 221 has a thickness T2 in the range of about 1 mm to about 12 mm, and more suitably in the range of about 1.5 mm to about 5 mm. In the illustrated embodiment, for example, the thickness T2 of the absorbent structure is approximately 3 mm. The shell 214 itself may have a thickness T3 between about 0.03 mm and about 5.0 mm, and more suitably about 0.1 mm to about 3.0 mm. In one particularly suitable embodiment, the thickness T3 of the shell 214 is between 0.25 mm and about 3.0 mm. In the illustrated embodiment, for example, the shell 214 has a thickness T3 of about 0.5 mm.

Figure 21:
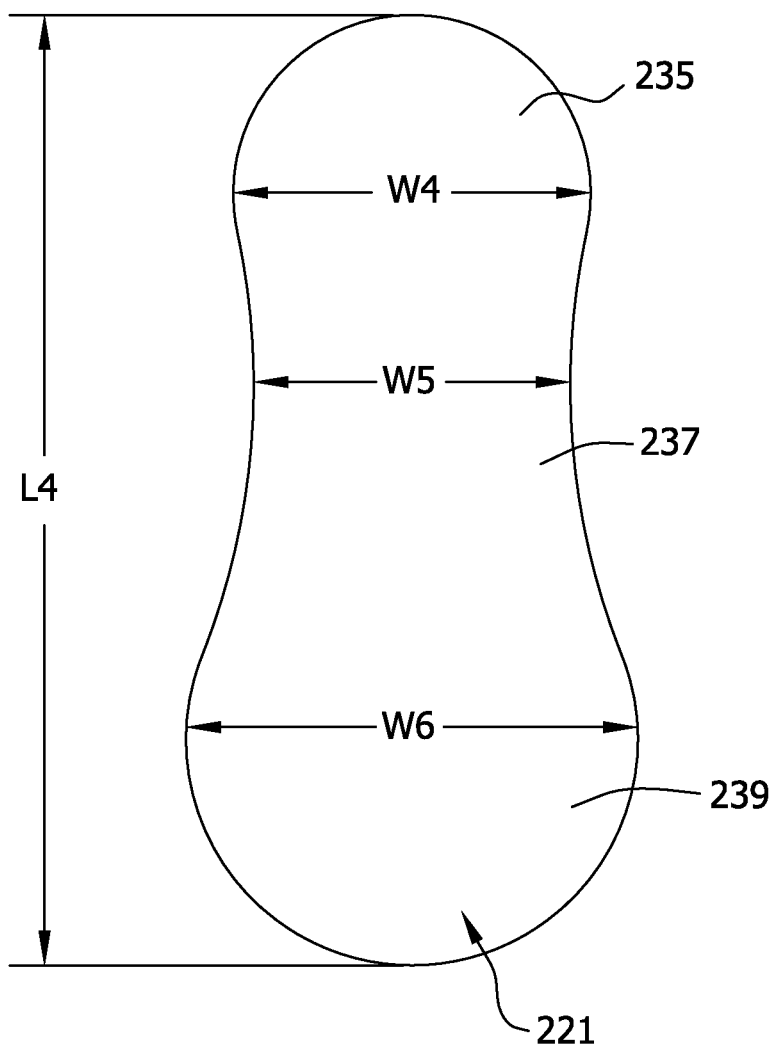
FIG. 21 shows a top view of an absorbent structure of the absorbent article.

With reference now to FIG. 21, the illustrated absorbent structure 221 has an upper portion 235, a middle portion 237, and a lower portion 239. The absorbent structure is generally hourglass shaped, with the upper portion 235 suitably having a width W4 between about 10 mm and about 80 mm, and more suitably about 30 mm to about 60 mm. In the illustrated embodiment, for example, the width W4 of the upper portion 235 is approximately 47 mm. The middle portion 237, which is the narrowest portion of the absorbent structure 221, may have a width W5 between about 10 mm and about 80 mm, and more suitably about 30 mm to about 60 mm. In the illustrated embodiment, the width W5 of the middle portion 237 is approximately 40 mm. The lower portion 239 has a width W6 between about 10 mm and about 120 mm, and more suitably about 40 mm to about 80 mm. In the illustrated embodiment, for example, the width W6 of the lower portion 239 is approximately 63 mm. In another suitable embodiment, the absorbent structure 221 has a longitudinal length L4 in the range of about 80 mm and about 180 mm, and more suitably about 110 mm to about 150 mm. As one example, the longitudinal length L4 of the illustrated absorbent structure 221 is about 145 mm. It is understood, however, that the absorbent structure may be sized in width and/or length other than as set forth above without departing from the scope of this invention. It is also understood that the absorbent structure 221 may be any suitable shape other than a generally hourglass shape within the scope of this invention.

With reference back to FIG. 16, the absorbent structure 221 is secured to the first side (i.e., body-facing surface) 215 of the shell 214, such that at least a portion of the absorbent structure covers the opening or ingress 205 in the shell. The absorbent structure 221 may be attached to the shell 214 in a permanent manner, meaning that the absorbent structure is generally intended not to be removable by the wearer of the absorbent article 200. Alternatively, it may be removably and in some embodiments refastenably) attached to the shell 214, such that the absorbent structure 221 may be removed (and in some embodiments reattached) by a wearer.

The shell 214 and absorbent structure 221 are sized relative to each other such that a portion of the shell extends outward beyond the peripheral edge of the absorbent structure along at least a portion of the peripheral edge of the absorbent structure. In this manner, a portion of the shell 214 about the periphery of the absorbent structure 221 is uncovered with the first side (i.e., body-facing surface) 215 of the shell exposed and available for adhesion to the wearer. For example, the shell 214 in one suitable embodiment extends outward beyond the peripheral edge of the absorbent structure 200 at least in the anterior region 264 and central region 265, and more suitably also in a portion of the posterior region 266. In accordance with one embodiment, for example, the shell 214 extends outward of the peripheral edge of the absorbent structure 221 a distance D3 in the range of at least about 3 mm, more suitably in the range of about 5 mm to about 15 mm and even more suitably about 8 mm to about 13 mm. In one embodiment, the entire first side 215 of the uncovered portion of the shell 214 has body adhesive 244 thereon for adhering the shell and thereby the absorbent article to the wearer.

As illustrated in FIG. 16, the distance that the shell 214 extends outward beyond the peripheral edge of the absorbent structure 221 is suitably non-uniform about the periphery of the absorbent structure. More particularly, the shell 214 extends transversely outward beyond each of the side edges of the absorbent structure 221 a greater distance in the anterior region 264 than in the central region 265. It is understood, however, that shell 214 may extend a uniform distance outward of the absorbent structure 221, or may extend outward according to a different pattern than illustrated in FIG. 16, and remain within the scope of this invention. In another suitable embodiment, the first side (i.e., body-facing surface) 215 of the shell 214 has a total surface area in the range of about 50,000 $mm^2$ to about 20,000 $mm^2$, and more suitably about 30,000 $mm^2$ to about 40,000 $mm^2$. The absorbent structure 221 has a total body-facing surface area of about 4,500 $mm^2$ to 45,000 $mm^2$ and more suitably about 15,000 $mm^2$ to about 20,000 $mm^2$. Thus, between about 10,000 $mm^2$ and about 45,000 $mm^2$, and more suitably about 18,000 $mm^2$ to about 22,000 $mm^2$ of surface area of the first side 215 of the shell 214 remains uncovered by the absorbent structure 221. Stated another way, about 40 percent to about 95 percent, and more suitably about 40 percent to about 65 percent of the shell 214 is uncovered by the absorbent structure 221.

As one example, in the illustrated embodiment the shell 214 has a total surface area of about 34,000 $mm^2$ of which about 20,000 $mm^2$ is uncovered and available to have body adhesive 244 applied thereto. The illustrated absorbent structure 221 has a total body-facing surface area of about 18,000 $mm^2$ of which about 14,500 $mm^2$ covers or overlies the shell 214. Accordingly, about 60 percent of the illustrated shell 214 has body adhesive 244 and can be used to adhere the absorbent article 200 to the wearer's skin. It is understood, however, that less than the entire exposed area of the shell 214 can have body adhesive 244 thereon. It is also understood that body adhesive can be applied to the absorbent structure 221 to adhere or partially adhere the absorbent structure to the wearer's skin.

Additional embodiments of an absorbent article 10 of the present specification are illustrated in FIGS. 22 through 41. As in the previous embodiments, one component of the absorbent article 10 is a shell 14 having a first side 15 and a second side 17. The shell 14 serves to provide the overall contour or silhouette of the absorbent article of the present invention. In addition, the shell 14 also provides a surface for attachment or adhesion of the absorbent article 10 to the body of a user.

Figure 22:
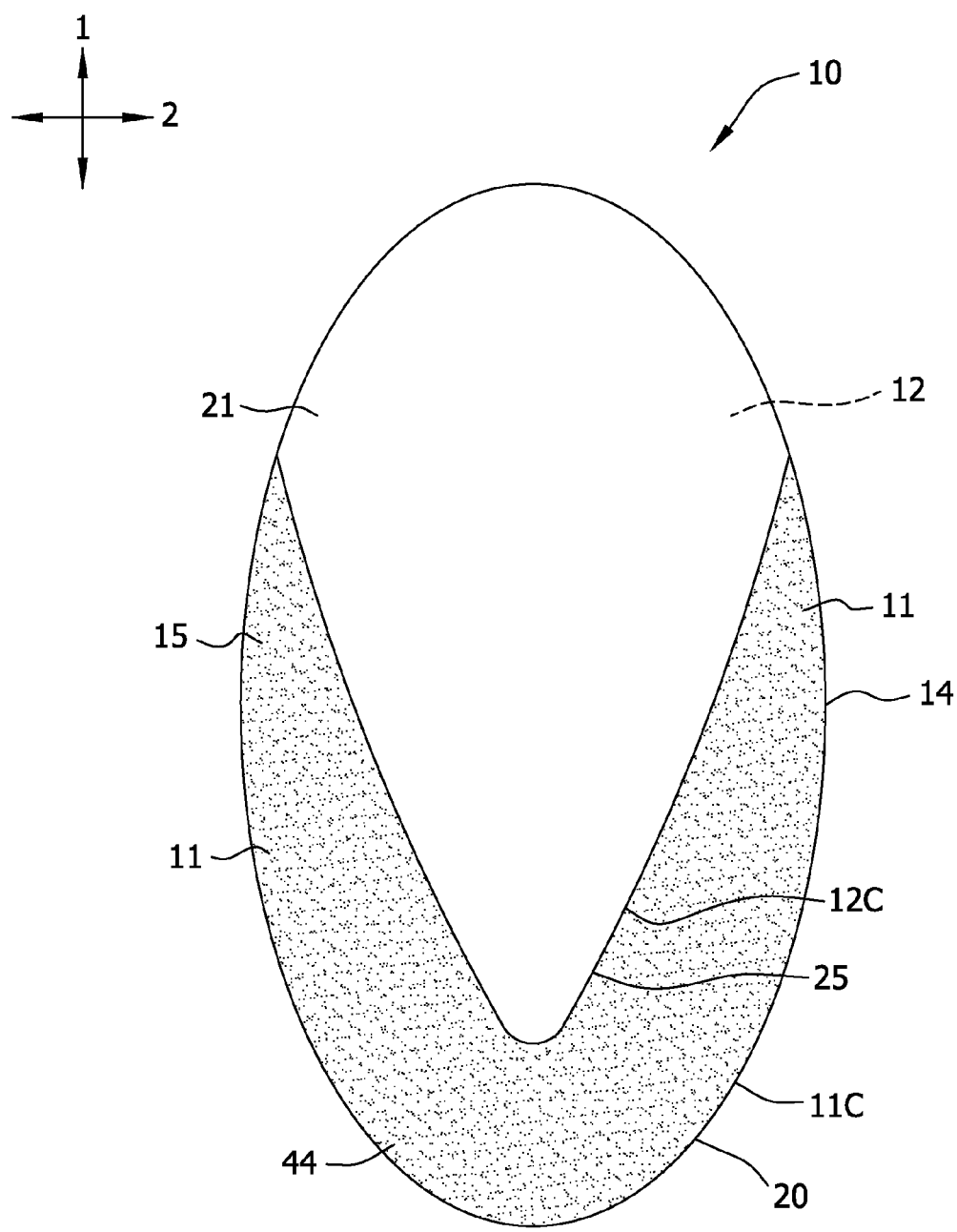
FIGS. 22 and 23 each show a top view of other embodiments of an absorbent article of the present invention.
Figure 23:
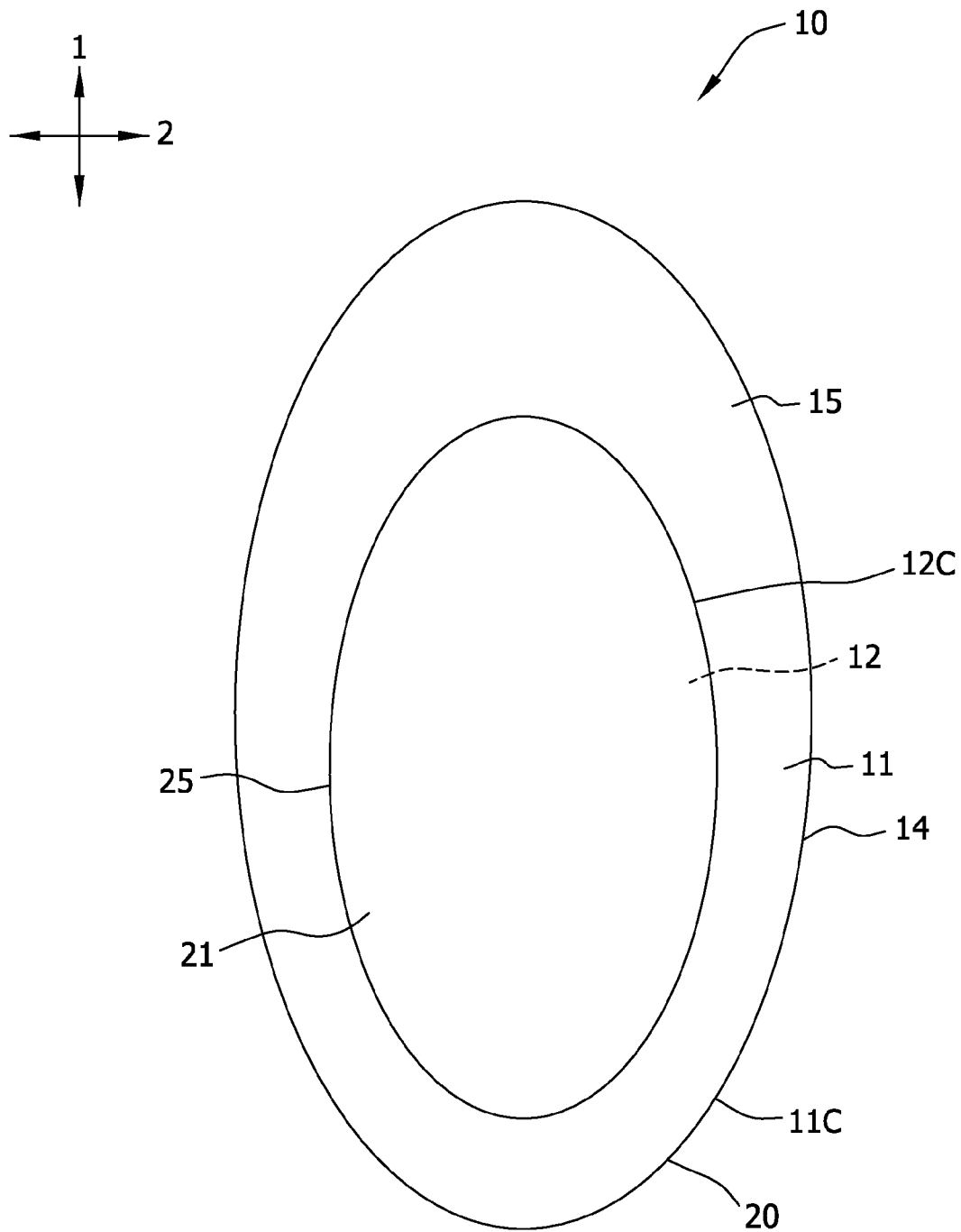

The first side 15 of the shell 14 is the body facing side of the absorbent article 10 and the second side 17 of the shell 14 is the garment facing side of the absorbent article. The first side 15 of the shell 14 has a first area 11 and a second area 12. The first area 11 surrounds or bounds the majority of the second area 12, as is clearly shown in FIG. 22. By "surrounds or bounds the majority", it is meant that at least 51% of a circumference 12C of the second area 12 contacts the first area 11. Generally, at least 60% of the circumference 12C of the second area 12 contacts the first area 11. In a particular embodiment, at least 75% of the circumference 12C of the second area 12 is in contact with the first area 11. In another particular embodiment, at least 90% of the circumference 12C of the second area 12 is in contact with the first area 11. In a further embodiment of the present invention, at least 95% of the circumference 12C of the second area 12 is in contact with the first area 11. In still a further embodiment of the present invention, the first area 11 completely surrounds the second area 12 of the shell 14 as is shown in FIG. 23.

In one embodiment, the first area 11 of the first side of the shell 14 is designed or adapted to contact, attach or adhere to the wearer's skin. In one particular embodiment, the first area 11 of the shell 14 is designed or adapted to contact a female wearer's skin surrounding the vulva region of the female torso when the absorbent article 10 is applied to the wearer. Generally, the shell 14 is sized and shaped such that the extent of the first area of the shell only contacts and attaches or adheres to the skin surrounding and proximate to the vulva area and possibly the pubic and perinea regions of the wearer. In addition to contacting the skin in the vulva, pubic and perinea regions of the wearer, the first area 11 of the first area of the shell 14 may also contact and attach or adhere to any hair in the vulva area of the user which may be present. The first area 11 is the portion of the first side 15 of the shell 14 which holds the absorbent article in place on the user.

Generally, the second area 12 of the shell 14 is the portion of the shell 14 which provides absorbency to the absorbent product. That is, the second area 12 of the first side to the shell is any area of the first side of the shell which has an absorbent structure attached thereto, or has absorbent properties. In one particular embodiment of the present invention, the second area 12 of the shell 14 has an absorbent structure 21 contained therein or attached to the shell 14 in the second area. It is noted that the second area 12 may be a single contiguous area or may be two or more distinct areas. Generally, the second area 12 is a single contiguous area from an ease of manufacturing standpoint. In an alternative embodiment, the second area 12 of the shell may contain an absorbent material integrated into the shell 14, such that the second area 12 of the shell is absorbent without the presence of an additional absorbent structure. The second area 12 shell may have an absorbent material coated or impregnated into the shell material.

Figure 25:
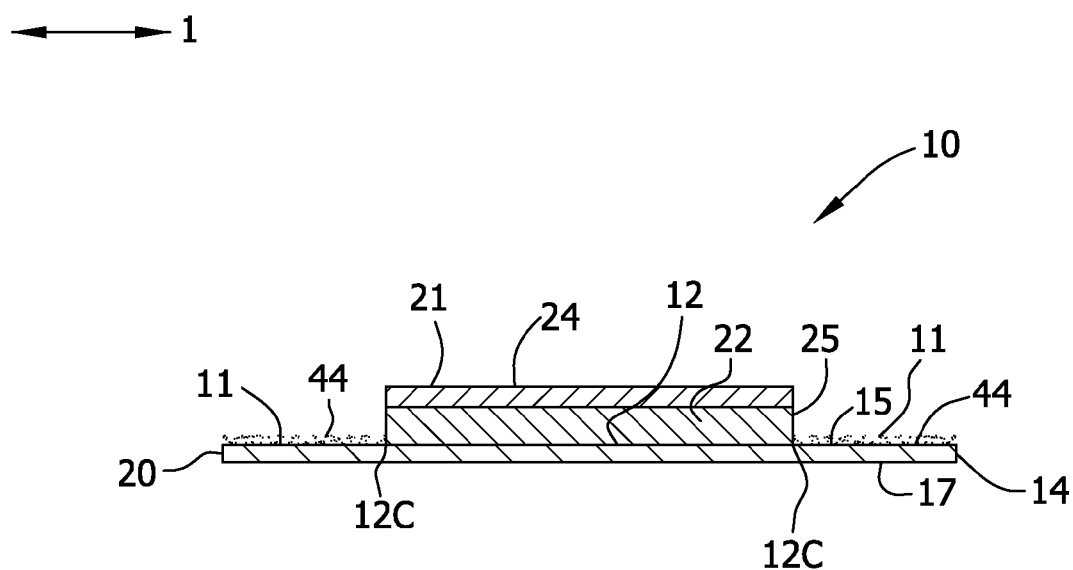

The shell 14 of the absorbent article 10 may be prepared from a variety of materials and can be liquid impermeable or liquid permeable. The shell 14 may, for example, include a polymeric film, a woven fabric, a nonwoven fabric or the like, as well as combinations or composites thereof. For example, the shell 14 may include a polymer film laminated to a woven or nonwoven fabric. A laminate shell 14 structure is shown in FIG. 25, having an upper layer 21 and a lower layer 20, wherein the upper layer is the body-facing side of the shell 14 and the lower layer is the garment facing side of the shell 14. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the shell 14 can operatively permit a sufficient passage of air and moisture vapor out of the absorbent article 10, particularly out of an absorbent structure 21 while blocking the passage of bodily fluids and odors often associated with bodily fluids. An example of a suitable shell material can include a breathable, microporous film, such as those described in, for example, U.S. Pat. No. 6,045,900 to Haffner et al., the entire disclosure of which is incorporated herein by reference and made a part hereof. Other shell materials which are extensible may be used in the present invention. Examples of extensible backsheet materials are described in U.S. Pat. No. 5,611,790, issued Mar. 18, 1997, to Osborn, III et al., herein incorporated by reference in its entirety.

In one particular embodiment of the present invention, the shell 14 may be a laminate of a woven or nonwoven fabric with a silicone polymer, wherein the silicone polymer has adhesive properties. The second side 17 of the shell will be woven or nonwoven fabric and the first side 15 of the shell will be silicone polymer. One commercially available laminate is an Oleeva Fabric® 1 available from Bio Med Sciences, Inc., which have offices at 7584 Morris Court, Suite 218 Allentown, Pa. 18106. The Oleeva Fabric® is a silicone sheeting having adhesive properties laminated to a fabric backing. The silicone sheeting will form the body facing first side 15 of the shell material. Relating this particular structure to the Figures, in FIG. 25, the silicone polymer is the upper layer 141 of the shell 14 and the nonwoven or woven layer is the lower layer 142 of the shell.

Bicomponent films or other multi-component films can also be used as the shell 14 material. In addition, woven and/or nonwoven fabrics which have been treated to render them operatively liquid-impermeable can also be used as an effective shell 14 material. Another suitable shell material can include a closed-cell polyolefin foam, a polyurethane polymer material, a silicone polymer or other similar materials. Silicone polymers having naturally occurring adhesive properties, or silicone polymers having a silicone adhesive layer applied thereto are of particular interest for the shell material. Such silicone polymers will allow the first area 11 of the shell 14 to adhere to the body of the user without the need of an additional adhesive. These materials may be laminated to another material such that the second side 17 of the shell 14, which is the garment facing side of the absorbent article 10, so that the adhesive nature of the silicone polymer does not adhere the garment to the undergarment of the user. In another embodiment of the present invention, the shell material may be prepared from an interpenetrating polymer network or two or more polymers. Generally, one of the polymers of the interpenetrating polymer network may be a silicone material. Examples of interpenetrating polymer networks are described in U.S. Pat. No. 5,759,560, issued to Dillion, which is hereby incorporated by reference in its entirety.

The shell material should be selected such that the overall properties of the shell allow the shell material to move the skin of the user during normal use and normal movements by the user during use. The shell 14 should not be too rigid, such that the shell detaches from the skin of the user during use and the shell should not be so flexible that the shell tends to twist and bunch during use. The shell 14 should have sufficient flexibility to conform to the skin of the user and become similar to a second skin of the user.

Generally, the shell material should have sufficient thickness to allow the shell 14 to mold to the body of the user, but not too thick that the shell 14 becomes uncomfortable for the user to wear. In addition, the shell 14 should not be so thin that it ineffectively forms a seal with the skin of the user when applied to the user, or becomes detached from the skin of the user during use and normal movement of the user during use or that it does not adequately conform to the shape and skin of the user at the point of attachment to the user. Depending on the material used for the shell, the typical thickness of the shell is between 0.03 mm and about 5.0 mm, more particularly between 0.1 mm and 3.0 mm. In one particular embodiment, the thickness of the shell is between 0.25 mm and about 3.0 mm. Again, the actual thickness used is dependent of several factors including rigidity of the material, the flexibility of the material and the ability of the material to assume the shape of the skin of the user at the location of use, which is typically the vulva region of a user.

The second side 17 of the shell 14 forms the garment-facing side of the absorbent article when worn by a user. The shell 14 material should be selected such that the second side of the shell will freely move against the undergarment or clothing of a user. One way to achieve this result is to have the second side 17 of the shell 14 to have a fairly low coefficient of friction. This will allow the second side 17 of the shell 14 to freely move against the undergarment or other clothing worn by the user. If the second side 17 of the shell 14 does not freely move against the undergarment or other clothing worn by the user, the absorbent article may catch on the undergarment or clothing, which may result in the absorbent article being prematurely and undesirably removed from the user or may cause the absorbent article to be shifted from its desired placement against the body of a user.

In order to achieve the desired coefficient of friction on the second side 17 of the shell 14, the materials used to prepare the shell could be selected such that the second side 17 of the shell material will inherently have the desired coefficient of friction. Alternatively, the second side 17 of the shell 14 may be treated with a coating composition, such a polytetrafluoroethylene containing coating, a silicone containing coating or other similar coating having low coefficient of friction properties. Alternatively, the shell 14 could be made from a laminate of two or more materials such that the first side 15 of the shell 14 is prepared from a material which meets the needed properties of the first side 15, while the material selected for the second side 17 of the shell 14 meets the desired coefficient of friction such that the second side 17 will freely move against the undergarment or garment being worn by a user.

Figure 26:
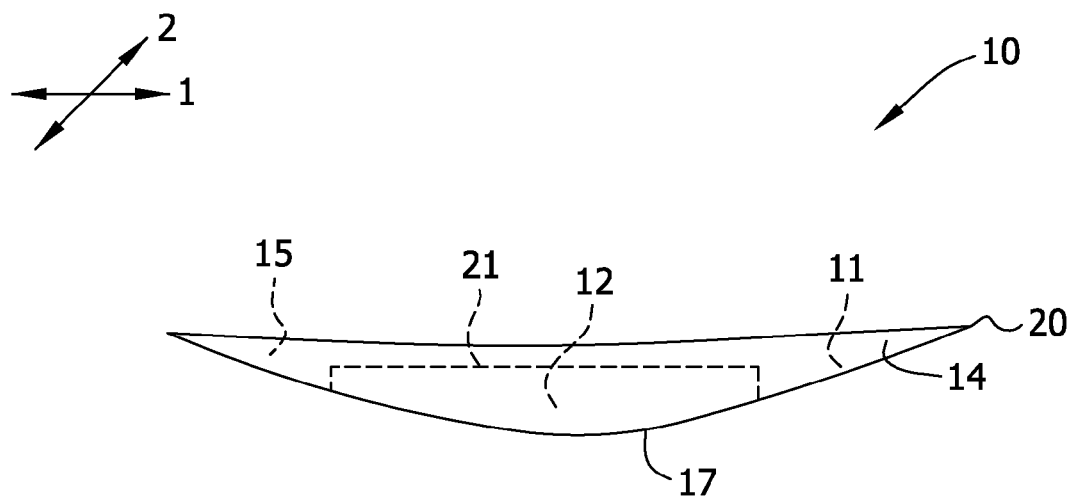
FIG. 26 shows a side view of another embodiment of an absorbent article of the present invention wherein the shell has a concave shape.

The shell 14 of the absorbent article 10 may be flat or may have a three-dimensional shape. As is shown in FIG. 26, which is a side perspective view of the absorbent article the shell 14 has a three-dimensional concave shape. Alternatively, as is shown in cross-sectional side views of FIGS. 24, 25 and 27, the shell 14 may have a generally flat shape. By providing the absorbent article 10 with a three-dimensional concave shape as is shown in FIG. 26, placement of the article may be easier for the user. Generally, the three-dimensional shape could be such that it closely matches the overall general curvature of the vulva region and optionally the pubic and perinea regions of most women, when the absorbent article is used as a pantiliner, sanitary napkin or a feminine incontinence article. To form the shell 14 with a three-dimensional shape, the shell may be molded in any manner known to those skilled in the art, for example heat molding. The manner in which the three-dimensional shape is imparted to the shell 14 is not critical to the present invention.

Figure 28:
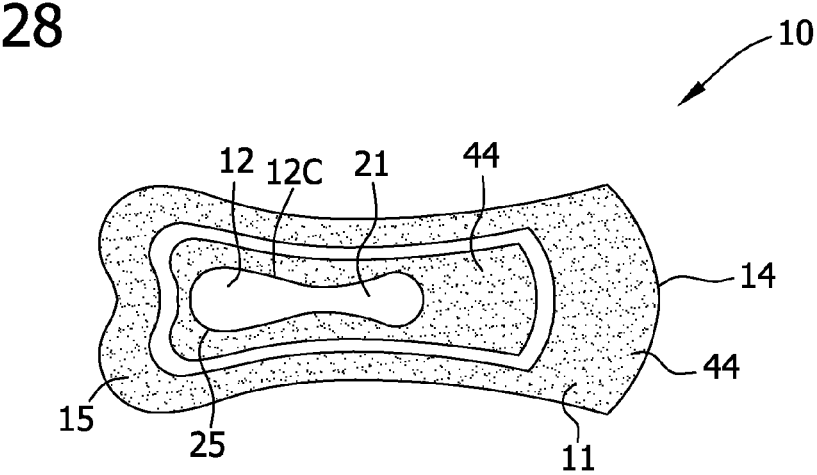
FIGS. 28-30 each show a top view of an embodiment of an absorbent article of the present invention having a different shell shape.
Figure 29:
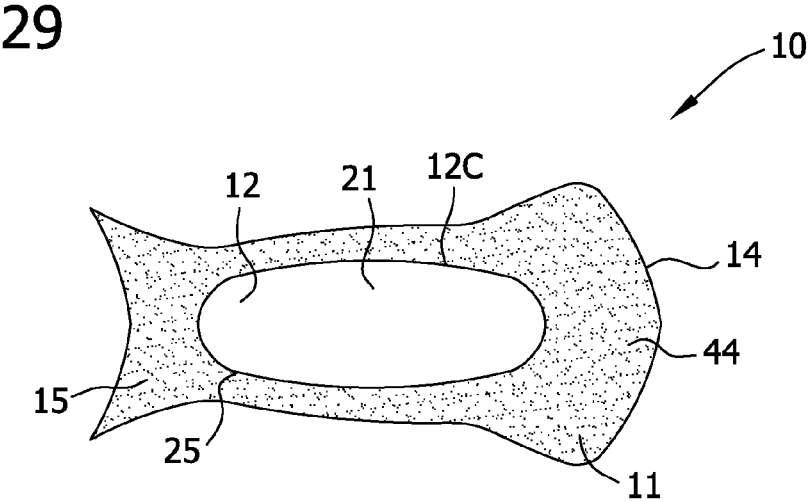
Figure 30:
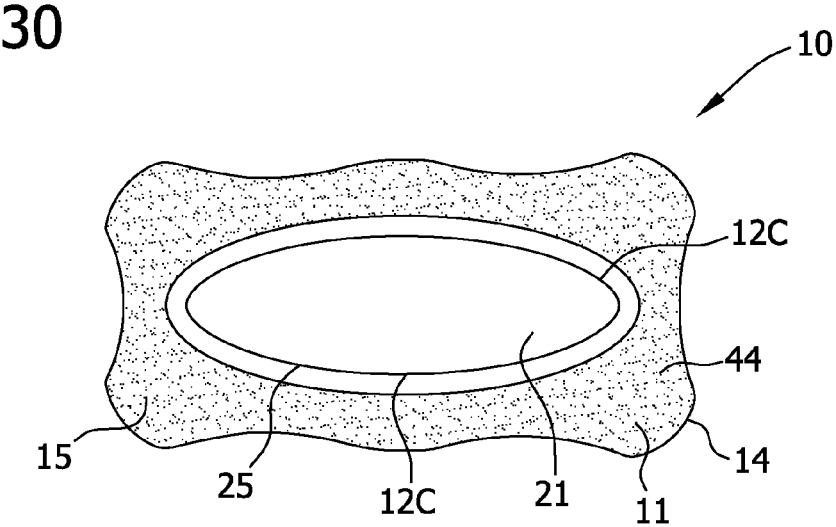

When the shell 14 is a flat shape, meaning that the shell does not have a third dimension other than thickness, the shell 14 should be made to be flexible enough that the shell 14 can conform to the body of the user at the point of attachment. In addition to being flat, the overall shape of the shell 14 may be contoured, as is shown in FIG. 28-30. In one embodiment, the contour shape may be such that the narrowest point of the contour is in the crotch area of the shell 14 nearest the vulva region, as is shown in FIG. 29. The contour shape shown in FIG. 28 is one of many possible shapes the shell 14 and absorbent article may be prepared. Other shapes may be used, without departing from the scope of the present invention. Generally, the shape selected should be such that the shell 14 and absorbent article 10 are comfortable for the user to wear, while providing leakage protection to the user. It is noted that a contour shape may also be used in conjunction with a three-dimensional shell. Further discussion of the overall shape of the absorbent article may be found below.

The shell may be any desired color or may be translucent. In addition, the shell may have a matt finish, satin finish or a smooth finish. The particular finish color or translucency can be a matter of choice for the manufacturer of the absorbent article of the present invention. However, a translucent shell may assist the user in placing the absorbent article 10 since the user may be able to see where the article is compared to the genitalia of the user.

The absorbent structure 21 is designed to absorb body exudates, including menstrual fluid, blood, urine, and other bodily fluids, such as sweat and vaginal discharges. The absorbent structure 21 has a longitudinal direction 1 and a lateral direction 2. This absorbent structure 21 may be a single layer or may be multiple layers. Typically, the absorbent structure 21 has an absorbent core 22. This absorbent core 22 may contain one or more layers of absorbent materials. That is the absorbent core 22 may be a single layer of absorbent materials or may be a multilayer structure. Each of the layers can contain similar materials or different materials. In the absorbent article 10 of the present invention, the materials which may be used to form the absorbent core 22 include those materials conventionally used in absorbent articles and includes materials, such as, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A desired material is wood pulp fluff, for it is low in cost, relatively easy to form, and has good absorbency.

The absorbent core 22 can also be formed from a composite comprised of a hydrophilic material which may be formed from various natural or synthetic fibers, wood pulp fibers, regenerated cellulose or cotton fibers, or a blend of pulp and other fibers. One particular example of a material which may be used as the absorbent core is an airlaid material. The absorbent core 22 may have other properties including extensibility, which will allow the absorbent core to be extended or fit to a particular user. One example of extensible absorbent cores is described in U.S. Pat. No. 5,611,790, issued Mar. 18, 1997, to Osborn, III et al., herein incorporated by reference in its entirety.

In one embodiment, the absorbent core 22 may also include a superabsorbent material, in addition to or in place of the hydrophilic material, which increases the ability of the absorbent core to absorb a large amount of fluid in relation to its own weight. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent materials can be inserted as particles or in sheet form. The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Hydroxyfunctional polymers have been found to be good superabsorbents for sanitary napkins. Such superabsorbents are commercially available from Evonik Industries, among others, and are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

Figure 24:
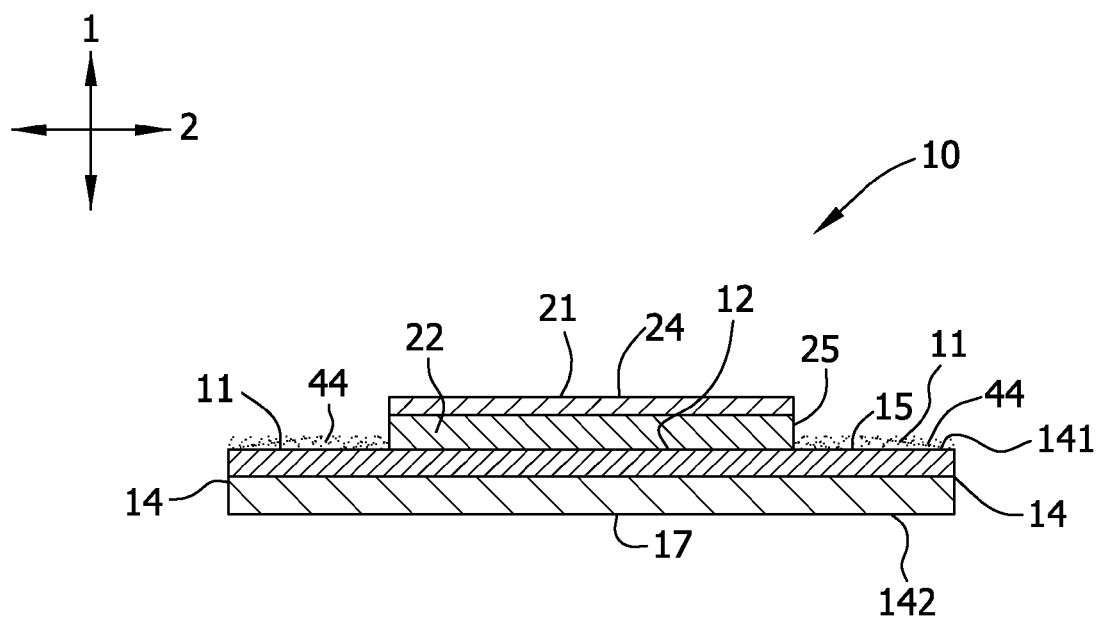
FIGS. 24 and 25 show side cross-sectional views of still other embodiments of absorbent articles of the present invention.
Figure 27:
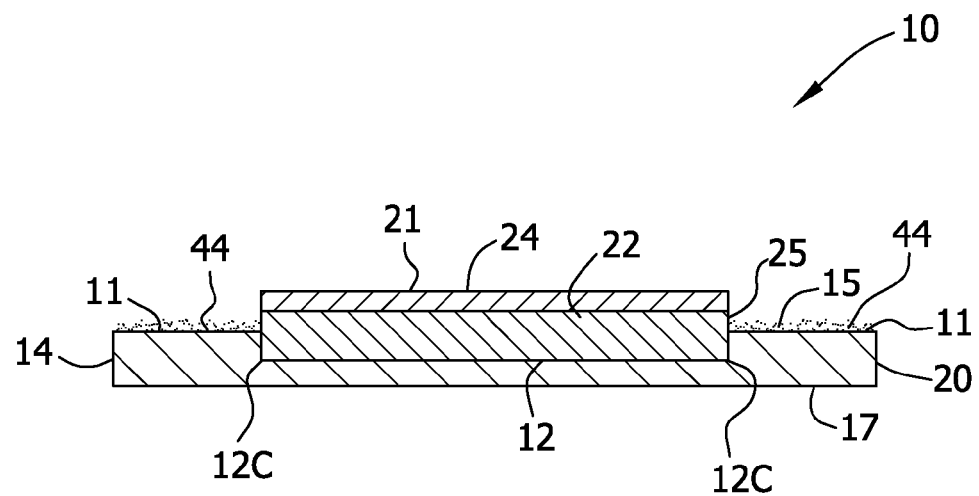
FIG. 27 shows a cross-sectional side view of an absorbent article of the present invention with the absorbent core recessed into the shell.

Generally, the absorbent core 22 will be positioned adjacent the shell 14, as is shown in FIGS. 24, 25 and 27. In addition, the absorbent core 22 may be recessed into the shell 14 as is shown in FIG. 27.

In addition to the absorbent core 22, the absorbent structure 21 may have other additional layers which aid the absorbent core 22 in capturing and holding the bodily fluid into the absorbent core 22. These other layers, when present and in combination with the absorbent core 22, form the absorbent structure 21 of the absorbent article 10. There may be a single layer or multiple layers in addition to the absorbent core in the absorbent structure 21. Alternatively, the absorbent structure 21 may have a single layer, which is generally the absorbent core 22.

One particular example of an additional layer which may be used in addition to the absorbent core 22 in the absorbent structure 21 is a body-side liner or top sheet 24, which is generally a liquid permeable material, which allows bodily fluids to pass through the top-sheet into the absorbent core. It is noted that the terms "body-side liner" and "top sheet" may be used interchangeable. The body side liner 24 also may provide a user with a dry feeling by separating the absorbent core 22 from the body of the user. That is, the body-side liner 24 is placed between the absorbent core 22 and the body of the user and such that the absorbent core 22 is between the body side liner 24 and the shell 14.

In the present invention, generally the body side liner 24 will only extend to the edge 25 of the absorbent core, as is shown in FIG. 24. However, the body side liner 24 may extend beyond the edge 25 of the absorbent core 22 and may be attached to the first side of the shell. Generally, if the body side liner 24 extends beyond the absorbent core 22, the body side liner will be attached to the first side 15 of the shell 14. Also, if the body side liner 24 extends beyond the absorbent core 22, the body side liner 24 will generally not cover the entire first area 11 of the first side 15 of the shell 14.

Optionally, the body side liner 24 may be formed from one or more materials. The body-side liner or top sheet 24 should be able to manage different body excretions depending on the type of product. In feminine care products, often the body-side liner or top sheet 24 must be able to handle menses and urine. In the present invention, the body-side liner or top sheet 24 may include a layer constructed of any operative material, and may be a composite material. For example, the body-side liner or body-contacting layer can include a woven fabric, a nonwoven fabric, a polymer film, a film-nonwoven fabric laminate or the like, as well as combinations thereof. Examples of a nonwoven fabric useable in the body-side liner or top sheet 24 include, for example, an airlaid nonwoven web, a spunbond nonwoven web, a meltblown nonwoven web, a bonded-carded web, a hydroentangled nonwoven web, a spunlace web or the like, as well as combinations thereof. Other examples of suitable materials for constructing the body-side liner or top sheet 24 can include rayon, bonded-carded webs of polyester, polypropylene, polyethylene, nylon, or other heat-bondable fibers, finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials. When the body-side liner is a film or a film laminate, the film should be apertured or otherwise be made to allow fluids to flow through the body-side liner to the absorbent core.

Other examples of suitable materials for the body-side liner or top sheet 24 are composite materials of a polymer and a nonwoven fabric material. The composite materials are typically in the form of integral sheets generally formed by the extrusion of a polymer onto a nonwoven web, such as a spunbond material. In a particular arrangement, the body-side liner or top sheet layer 24 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the liner or body contacting layer. The apertures or other openings can help increase the rate at which bodily liquids can move through the thickness of the liner or body contacting layer and penetrate into the other components of the article (e.g. into the absorbent core 22). The selected arrangement of liquid permeability is desirably present at least on an operative portion of the body-side liner or top sheet 24 that is appointed for placement on the body-side of the article. The body-side liner or top sheet 24 can provide comfort and conformability, and can function to direct bodily exudates away from the body and toward the absorbent core 22. The body-side liner or top sheet 24 can be configured to retain little or no liquid in its structure, and can be configured to provide a relatively comfortable and non-irritating surface next to the body tissues of a wearer. In the present invention, the top sheet or body-facing surface of each absorbent article may be embossed, printed or otherwise imparted with a pattern.

Additional layers or substrates, including for example, the liquid acquisition and distribution layer, also referred to as a surge or transfer layer, and an optional tissue layer are also incorporated into the absorbent structure 21 of the absorbent product 10, for example, between the body-side liner or top sheet 24 and the absorbent core 22. The liquid acquisition and distribution layer may be shorter than the absorbent core or have the same length as the absorbent core 22. The liquid acquisition and distribution layer serves to temporarily hold an insulting fluid to allow the absorbent core sufficient time to absorb the fluid, especially when a superabsorbent material is present.

In another embodiment, the absorbent core, transfer layer and other components, such as tissue layers, may be free floating (unattached) between the shell 14 and the top sheet 24, and only are secured along only the peripheral edges thereof. Alternatively, the absorbent core 22, transfer layer, if present, and any other layer or component, if present, may be attached to one or both of the shell 14 and top sheet 24 and/or to each other.

The absorbent structure 21, including the absorbent core, is generally attached to the first side 15 of the shell 14 in the second area 12 of the shell. The attachment may be in a permanent manner, meaning that the absorbent structure is generally intended not to be removable by the user of the absorbent article 10. Alternatively, the absorbent structure 21 may be made to be removable by the user, meaning that the absorbent structure 21 may be removed and replaced with another absorbent structure 21 by the user of the absorbent article 10. When the absorbent structure 21 is attached to the shell 14 in a permanent manner, meaning that the absorbent structure is not intended to be removed by the user, a construction adhesive may be used. Examples of useable construction adhesives include any adhesive which will effectively hold the absorbent structure 21 in place, so as not to be separated from the shell 14. Commercially available construction adhesives usable in the present invention include, for example include Rextac adhesives available from Huntsman Polymers of Houston, Tex., as well as adhesives available from Bostik Findley, Inc, of Wauwatosa, Wis. Other means may be used to hold the absorbent structure 21 to the shell including other bonding means, including heat bonding and ultrasonic bonding. When the absorbent structure 21 is removably attached, the absorbent structure 21 is held in place on the shell 14 by a means which will allow the user to remove the absorbent structure. One such means of holding the absorbent structure is by using a pressure sensitive adhesive. Suitable pressure sensitive adhesives include any commercially available pressure sensitive adhesive. Examples of suitable pressure sensitive adhesives usable to removably hold the absorbent structure 21 in place on the shell 14 include pressure sensitive adhesives available from Henkel International. By providing an absorbent structure which is removable, the shell may be reused several times without the need to again place the shell when the absorbent needs to be replaced. Also by having a removable absorbent structure, the absorbent structure can be selected by the user prior to use. This would allow the user to select an appropriate level of protection for a given day or allow the user to select a size or shape of the absorbent which the user finds to be more comfortable.

As is stated above, the absorbent structure 21 is located in the second area 12 of the shell 14 and on the first side 15 of the shell member. This size and shape of the absorbent structure may be varied depending of the intended use of the absorbent article and will be discussed in more detail below.

The absorbent structure 21 may have a relatively flat structure, as shown in FIGS. 24-27. Alternatively, the absorbent structure may have a three-dimensional shape other than a relatively flat shape. The absorbent structure may have an anatomically correct shape such that the absorbent structure fits within the labia of the user. Anatomically correct shapes of absorbent are generally know to those skilled in the art and are generally found in the interlabial art field. The absorbent structure may be designed to be partially or fully interlabial. Alternatively, a three-dimensional shaped absorbent structure may also be used in the absorbent article 10 which is designed not to fit within the labia majora of the user. That is, the absorbent structure 21 is positioned completely outside the labia during use. The size, location and shape of the absorbent structure 21 may also be selected for an intended use. For example, in an overnight use, the absorbent may be located further back on the user towards the perinea region of the user. In an overnight use, the absorbent structure may be larger than in a product intended for daytime use. In a daytime use, the absorbent structure will generally be centrally located of the vulva region.

In an alternative embodiment of the present invention, the absorbent structure 21 is contained within the shell material. That is, the absorbent structure 21 is an integral part of the shell 14 and a separate absorbent structure is not present. One way to achieve an integral absorbent structure is to have a shell which is prepared from a material which is a laminate of two or more materials. The first side 15 of the shell 14 contains an absorbent material within the body facing side of the laminate. For example, superabsorbent particles or materials may be incorporated into the material making up the body facing layer of the laminate. Another way is to place a very light coating onto the first side 12 of the shell material, wherein the coating contains superabsorbent particles or materials. Of course other absorbent materials, other than superabsorbent materials may be used in place of or in addition to the superabsorbent materials.

Figure 31:
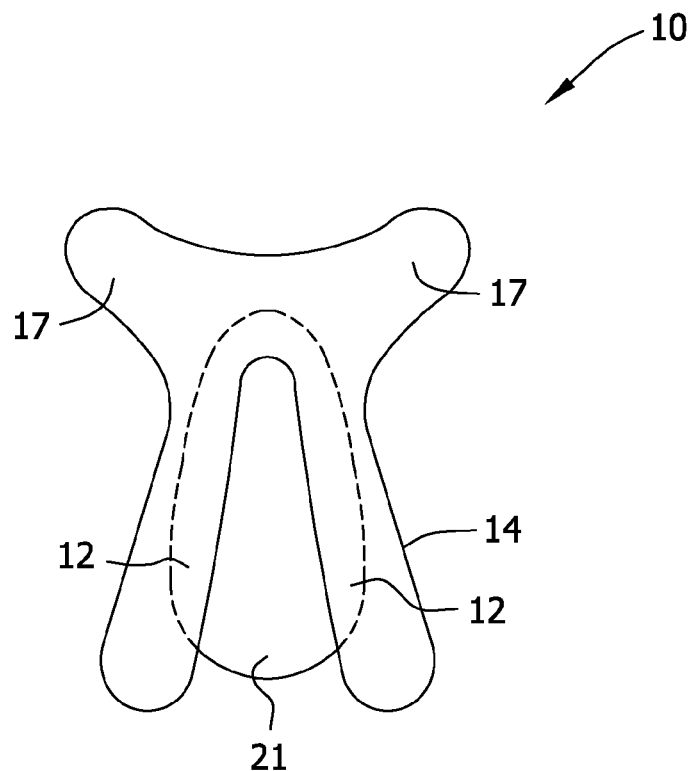
FIG. 31 shows a bottom view of an embodiment of an absorbent article of the present invention where only a portion of the absorbent structure is positioned over shell.
Figure 32:
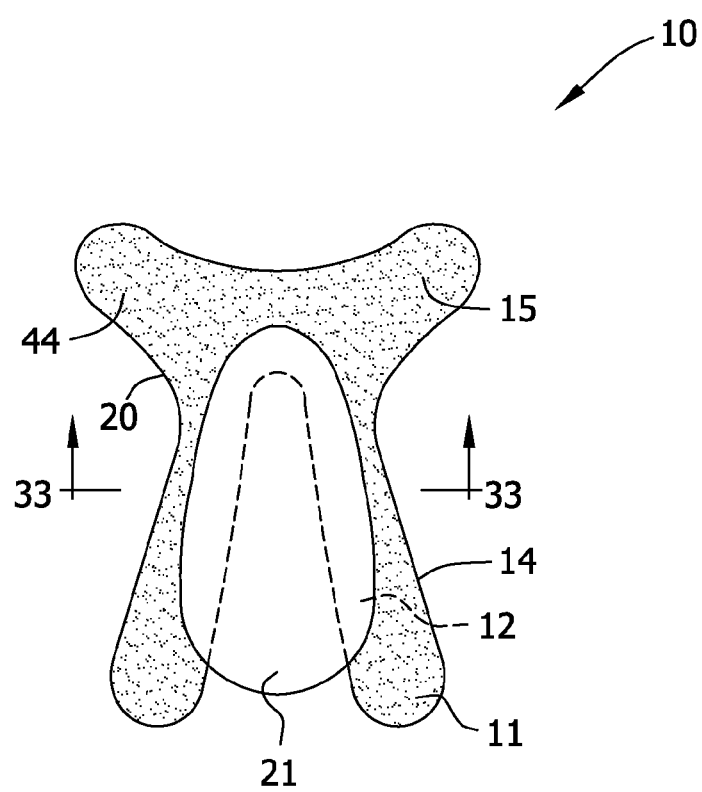
FIG. 32 shows a top view of an embodiment of an absorbent article of the present invention where only a portion of the absorbent structure is positioned over shell.
Figure 33:
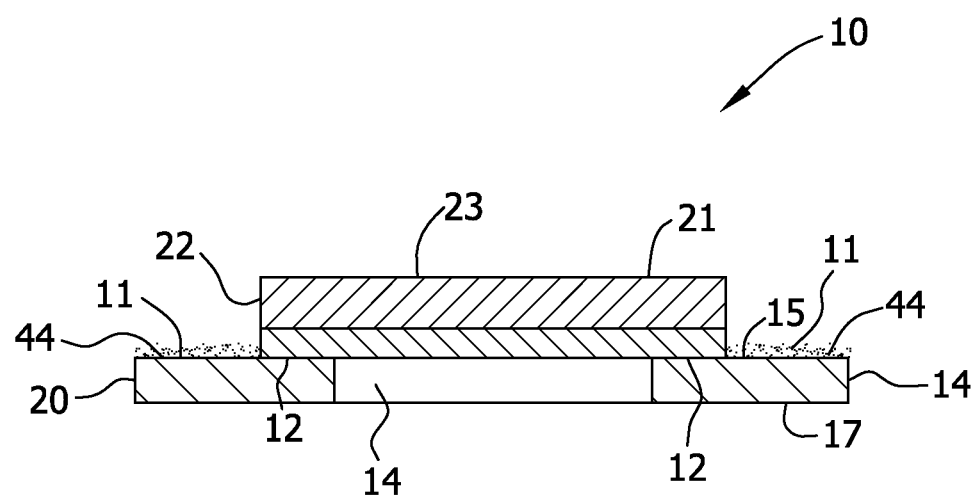
FIG. 33 shows a cross-sectional view taken along sectional line 33-33 of FIG. 32.

The absorbent structure 21 may be located entirely over the shell 14, as is shown in FIGS. 22-27, meaning at the shell 14 material is located beneath the absorbent structure 14. Alternatively, the absorbent structure 21 may be positioned over the shell 14, such that only a portion of the absorbent structure 21 is over the shell 14. This configuration is shown in FIGS. 31-33. FIG. 31 is a bottom view and FIG. 32 is a top view of an absorbent article 10 within the present invention. As can be seen only a portion of the absorbent structure 21 is positioned over the shell 14. FIG. 33 shows a cross-sectional view of the absorbent article 10 taken along line 33-33 in FIG. 32. As with the other embodiments of the present invention, the portion of the first side 15 of the shell 14 in which the absorbent structure is attached is the second area 12 of the shell 14. Surrounding the second area 12 is the first area 11 of the shell 14. The second side 17 of the shell 14 is the side of the absorbent article which faces the user during use. By having an absorbent article with the structure shown in FIG. 33, it is also beneficial for the absorbent structure to have an additional layer 23. This additional layer will serve to provide liquid impermeability to the absorbent structure, such that any fluids entering the absorbent core will not flow through the core to clothing of a user.

This additional layer 23 may be prepared from a variety of materials and is generally, this additional layer constructed of any material which will function to be operatively liquid impermeable. The additional layer, may be a polymeric film, a woven fabric, a nonwoven fabric or the like, as well as combinations or composites thereof. For example, the shell 14 may include a polymer film laminated to a woven or nonwoven fabric. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the additional layer can operatively permit a sufficient passage of air and moisture vapor out of the absorbent article 10, particularly out of an absorbent structure 21 while blocking the passage of bodily fluids and odors often associated with bodily fluids. Examples of suitable materials for the additional layer 23 include a breathable, microporous film, such as those described in, for example, U.S. Pat. No. 6,045,900 to Haffner et al., the entire disclosure of which is incorporated herein by reference and made a part hereof.

As is stated above, the first area 11 of the shell 14 serves either directly or indirectly attaches to the body of a user. Stated another way, the shell is the body attachment member and the first area 11 is the portion of the shell 14 which is attached to the body of the user. Depending on the material selected for the shell, the shell may actively attach to the body of the user using electrostatic means; suction means or a body adhesive may be placed on the first area 11 of the shell 14 to attach the absorbent article to the body of a user. Electrostatic means which can be used is by selecting the shell material to be a material which has an affinity for the body of a user, such that the shell material "clings" to the body of the user. Examples of such materials include ethylene vinyl acetate, low density polyethylene and other similar materials know to those skilled in the art. Suction means may be achieved by shaping the shell to conform to the body of the user, much like a contact lens fits to the eye. Generally, suction means can be achieved by forming the shell 14 into a three-dimensional shape. The easiest way to achieve body attachment is to place a body adhesive in the first area 11 of the shell 14.

The body adhesive 44 is positioned on the first area 11 of the first side 15 of the shell 14. The body adhesive 44 contacts the skin and hair, if present, in the vulva region and possibly the pubic region and/or the perinea region of the wearer's body, thereby supporting and holding the absorbent article 10 against the body of the wearer during use. The body adhesive 44 can overlie a portion of the first area 11 or can overlie the entire first area 11 of the shell 14. Generally, the body adhesive 44 will be present on a least the outer portion or near the circumference 11C of the first area near the edge 20 of the absorbent article. As is shown in FIGS. 22-25, 27, 30, 32 and 33, the adhesive may cover the entire first area 11 of the absorbent article. Alternatively, the body adhesive 44 may be placed on a portion of the first area 11, as is shown in FIGS. 28 and 29. The body adhesive 44 may also be placed in a pattern of the first area 11. The body adhesive 44 can be applied to the first area 11 of the shell 14 of using any known process including, inkjet printing, screen printing or extruding the body adhesive 44 from one or more nozzles, slot coating and the like.

Generally, any pressure sensitive adhesive known to those skilled in the art may be used, provided that the pressure sensitive adhesive is not a known irritant to human skin or that the adhesive is so aggressive that it causes pain to the user when the absorbent article is removed from the skin. It is also desirable that the adhesive is selected such that the adhesive does not leave a substantial amount of an adhesive residue on the surface of the skin of the user, when the absorbent article 10 is removed by the user after use. Particularly suitable pressure sensitive adhesive materials are disclosed in the commonly assigned U.S. Pat. No. 6,213,993 to Zacharias et al., U.S. Pat. No. 6,620,143 to Zacharias et al., the entire disclosure of each is incorporated herein by reference and made a part hereof. Other suitable adhesives are disclosed in U.S. Pat. No. 5,618,281 to Batrabet et al., the entire disclosure of which is incorporated herein by reference and made a part hereof. Other known body adhesives, such as those described in U.S. Pat. No. 6,316,524 to Corzani et al. which is hereby incorporated in its entirety, may also be used. Other examples of pressure sensitive adhesives include, Hydrogels, Hydrocolloids, Acrylics based adhesives, rubber based adhesives, such as Kraton based adhesives.

Figure 34:
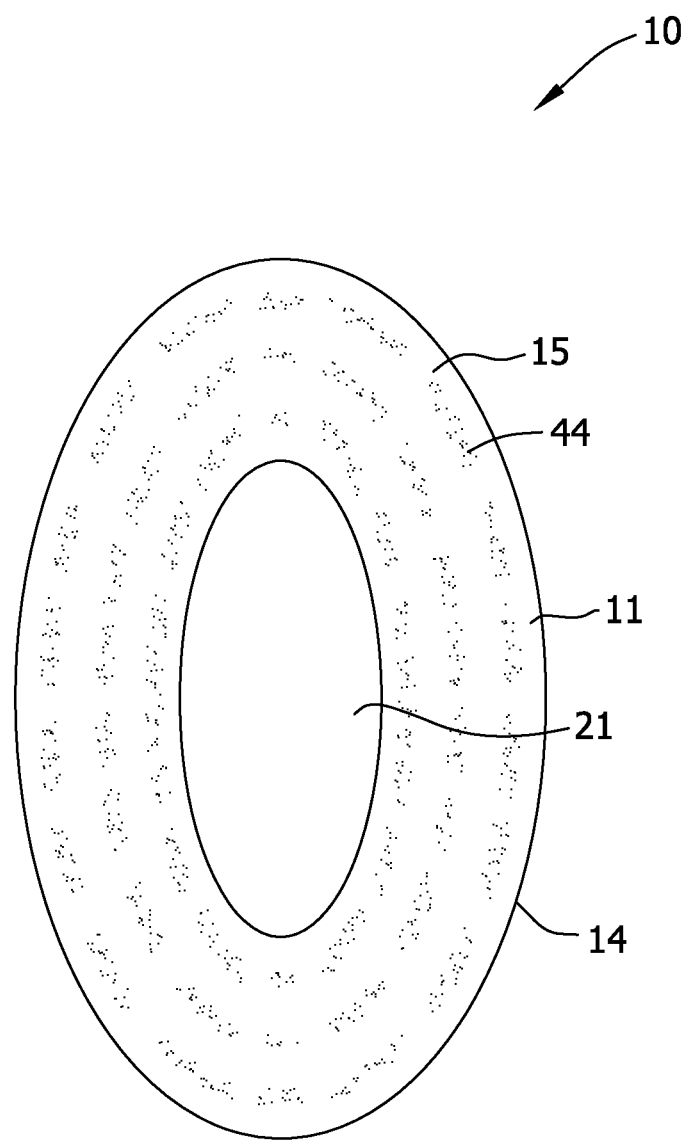
FIG. 34 shows a top view of an embodiment of an absorbent article of the present invention wherein the body adhesive is applied in an open pattern.

The body adhesive 44 may be positioned on the first area 11 of the shell 14 in an open pattern or a closed pattern. By "open pattern" is meant that the adhesive can have an intermittent or discontinuous pattern which does not substantially encircle the entire first area 11. For example, there are breaks in the body adhesive at certain portions of the first area 11. An open pattern of adhesive is shown in FIG. 28. "Closed pattern" means the adhesive 44 would encircle the entire second area 12 of the shell. Preferably, the pattern of the body adhesive 44 will substantially surround the absorbent structure located in or on the second area 12 of the shell 14. As shown in FIGS. 22, 23, 24, 25, 27, 30, 32 and 33, the body adhesive 44 is applied in a closed pattern, since the entire body adhesive is applied in a continuous fashion around the first area. An "open" pattern of the adhesive is shown in FIG. 34, which shows the adhesive applied in a discontinuous fashion. Additionally, the adhesive may be applied in portions of the first area 11, as is shown in FIGS. 28 and 29. In the present invention, the closed pattern can be advantageous since the body adhesive 44 may form a seal with the body of the user which will assist in preventing leaks from the absorbent article 10. The body adhesive may form a dam, which may prevent leaks from the entire perimeter of the absorbent article.

In one embodiment of the present invention, as is shown in FIGS. 22-25, 27, 30, 32 and 33, the body adhesive 44 may be placed on the entire first area 11, just outside of the absorbent structure 21. In another alternative embodiment of the present invention, as is shown in FIG. 28, the body adhesive 44 may be placed along the outer portions of the first area 11 near the periphery of the shell 14. The body adhesive 44 may also be placed on the absorbent structure 21. Generally, however, the body adhesive 44 is confined to being placed on the first area 11 of the shell 14, since placing the body adhesive on an area of the absorbent product 10 which contacts the female genitalia such as the labia majora may cause discomfort to the wearer of the absorbent product.

The adhesive may be applied in a pattern of small discrete dots so as to leave numerous areas free from adhesive. Alternatively, the adhesive may be applied as a continuous bead, or may be applied as a series of semi-continuous beads. Other suitable adhesive patterns may be selected for applying the body adhesive 44 to the body-contacting first area 11 of the absorbent article 10. For example, adhesive patterns can be oval, swirls, various linear or non-linear arrays of adhesive longitudinally, and/or transversely oriented and reticulated webs having unobstructed interstices between the adhesive fibers or combinations thereof. As stated above, the adhesive patterns may be open or closed. The weights of adhesives are limited to less than about 800 g/m2, and generally less than about 400 g/m2. Generally, the weight of the adhesive is at least 20 g/m2. Typically, the adhesive is applied in an amount of about 100 to about 400 g/m2. The limitations on the basis weight of the adhesive are important to provide the correct adhesive characteristics for applying directly to the wearer's vulva region and optionally the pubic and perinea regions of the wearer's body. If the basis weight is too high, the absorbent article will have a sticky feeling or otherwise uncomfortable feeling. If the basis weight of the adhesive is too low, there may be insufficient adhesion to the body of the user.

Generally, the body adhesive 44 is applied in a manner which is symmetrical about the longitudinal axis 1 which bisects the absorbent article 10 and divides the absorbent article 10 into substantially equal portions. This symmetrical pattern provides the wearer a balanced feel when wearing the absorbent article 10. The symmetrical pattern also reduces the perception of any associated discomfort when the absorbent article 10 is removed from the body.

Figure 35:
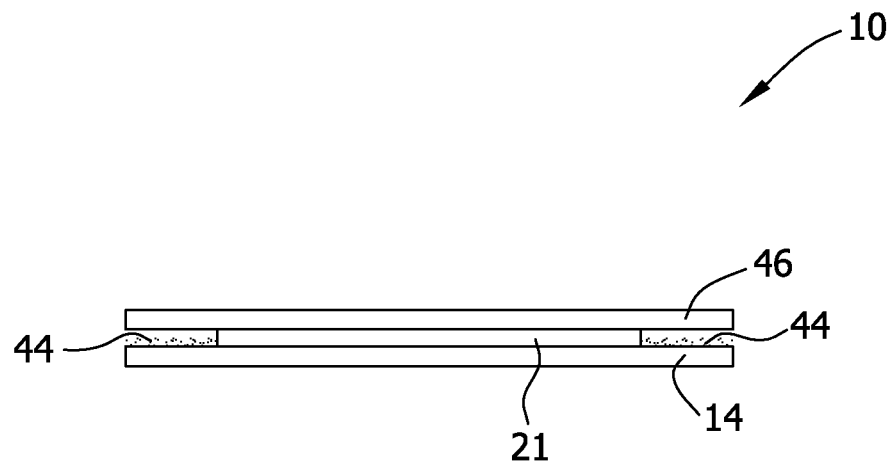
FIGS. 35-37 each show an absorbent article of the present invention having a release sheet applied thereto.
Figure 36:
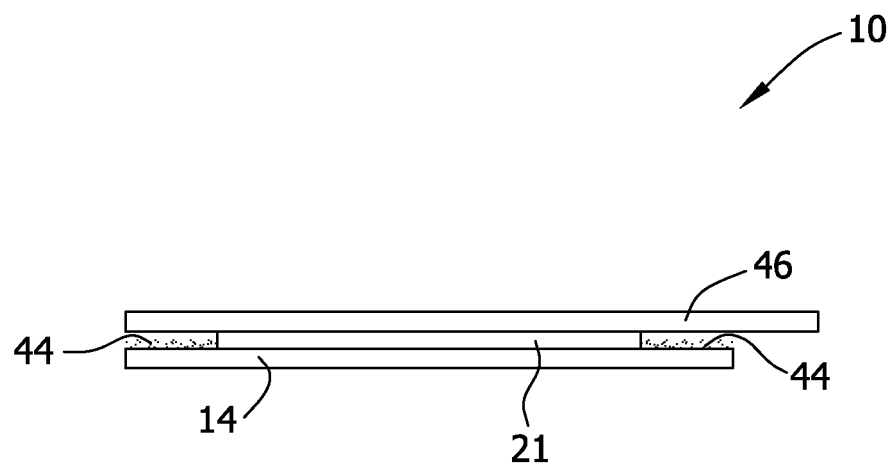
Figure 37:
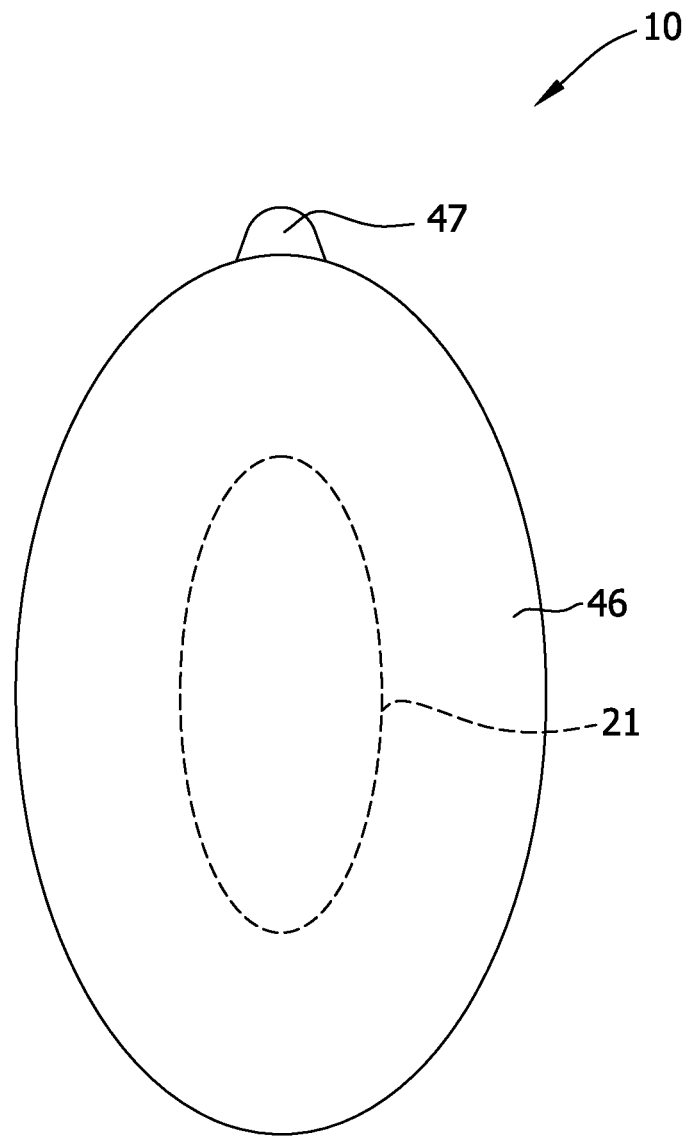

As is shown in FIGS. 35 and 36, to protect the body adhesive 44, a peel sheet or release sheet 46 may be used to prevent the body adhesive 44 from becoming contaminated, thus loosing its ability to stick to the body of an user and/or prematurely adhering to an unintended surface. Suitable materials for use as a peel strip 46 are well known in the art and are commercially available. Examples of suitable peel sheets or release sheets include, a silicone coated Kraft paper, a silicone coated film or the like. Other release coating includes coating containing polytetrafluoroethylene. The peel sheet or release sheet 46 may extend beyond one or both of the ends and/or sides of the shell, as shown in FIG. 36. Alternatively, the release sheet 46 may be sized to only cover the body adhesive on the first area 11 of the shell 14, as is shown in FIG. 35. In yet another embodiment of the present invention, release sheet may extend beyond the adhesive at one or more locations, such as one of the ends or one of the sides of the shell as is shown in FIG. 37 by providing the release sheet 46 with a tab 47 for the user to grasp to remove the release sheet 46 from the absorbent article 10 and the body adhesive 44 on the absorbent article. When the release sheet 46 extends beyond the adhesive, it is generally easier for the user to remove the release sheet 46 to place the absorbent article 10 for use.

Alternatively, the release sheet 46 may be provided with a pressure sensitive adhesive to hold the release sheet 46 in place when the absorbent article is devoid of an adhesive for body attachment. In this configuration, the release sheet serves to protect the absorbent structure and first side of the shell from dirt and damage prior to use.

In another alternative, a release sheet may not be necessary. For example, the absorbent article may be rolled, folded onto itself or stacked upon each other. In these configurations, a release sheet is not needed. If rolled, the body adhesive 44 will generally contact the second side 17 of the shell 14. The body adhesive 44 should releasably stick to one second side of the shell by readily releasing when unrolled by the user or wearer. In addition, the body adhesive 44 should not leave a residue on the second side 17 of the shell. This should similarly occur when the absorbent articles 10 are stacked upon each other such that the body adhesive 44 of one article will attach the second side of the shell of a second article. In another possible configuration, the absorbent article may 10 be folded along the longitudinal axis 1 of the lateral axis such that the body adhesive 44 in one area comes into contact with body adhesive in another area. In the folded configuration, the body adhesive should be selected such that the body adhesive will release from itself when manipulated by a user.

The dimensions and shape of the shell 14 should be such that it is appropriately sized for its intended use. The same is true for the size and shape of the absorbent structure. Generally, the size and shape of the absorbent structure 21 will dictate the size of the shell 14. The shape of the shell 14 is selected so that the absorbent article will have a comfortable feeling for the user, which providing protection against leaks and preventing the absorbent article from becoming dislodged from the body of the user during user. Generally, the shell will be curved to fit the body of a user. The shell 14 also generally gives the absorbent article 10 its overall size and shape in the longitudinal 1 and lateral 2 directions.

When the absorbent article is intended for use as a pantiliner, a sanitary napkin or a feminine incontinence article, the shell 14 should be wider and longer than the absorbent structure 21 attached to the second area 12 of the shell 14. The absorbent structure should be at least as wide and as long as the labia majora of the user. As a result, to fit most women, the absorbent structure is longer in the longitudinal direction than it is wide in the lateral direction of the absorbent structure. Generally, for most women, the labia majora are generally between about 40 mm and about 70 mm in width and between about 80 mm and 150 mm in length. Ideally, the absorbent structure should be wider than the labia majora and slightly longer than the labia minora and slightly longer than or equal to the labia majora. Generally, the absorbent should be between about 40 mm and 90 mm in width in the lateral direction and between about 95 mm and about 150 mm in length the longitudinal direction. The shape of the absorbent structure 21 will generally tend to be oblong and may be an oval, a rectangle, tear drop shaped, hourglass shaped or racetrack shaped. As can be seen in FIGS. 22, 28, 30, 32, 34 and 38, the absorbent structure 21 has a generally elliptical or oval shape to match the size and shape of the vaginal area of most women. An example of a teardrop shaped absorbent is shown in FIG. 22.

Generally, the shape of the shell 14 may vary from a generally oval shape, as shown in FIGS. 22 and 23 to a shape which is a generally hourglass-like shape, shown in FIG. 29. By generally hourglass shape, it is meant a shape in which the sides 19 of the shell 14 converge towards one another at a point away along the longitudinal axis 1 of the shell 14 to form a narrowest portion 33 of the absorbent article. Generally, the hourglass-like shape provides a cut-out for the user's legs. By having an hourglass-like shape, the shell 14 will not be attached to the legs of a user during use. This will provide more comfort for the user of the absorbent article 10. The shape of the shell 14 should be selected such that the absorbent article 10 will be comfortable to wear, while providing very effective leakage protection to the user. The shell 14 and the absorbent structure 21 should be able to adapt to the curvature of a user's body during use. Other possible shapes for the shell 14 are also shown in FIGS. 28, 29, 30, and 31. Other shapes not specifically shown may also be used, provided that the shape will provide comfort to the user of the absorbent article.

To obtain an effective attachment of the absorbent article to the user, when the absorbent article is used as a sanitary napkin or an incontinence article, generally the width of the shell should be at least 10 mm on either side of the labia majora. Generally, the shell 14 of the absorbent article 10 will have a width, in the lateral direction 2, between about 50 mm up to 200 mm or more. Typically, the shell will be between about 60 and 120 mm at its narrowest point. This will allow the shell 14 to have a first area 11 that can be effectively attached to the skin of a user on either side of the labia majora.

Figure 38:
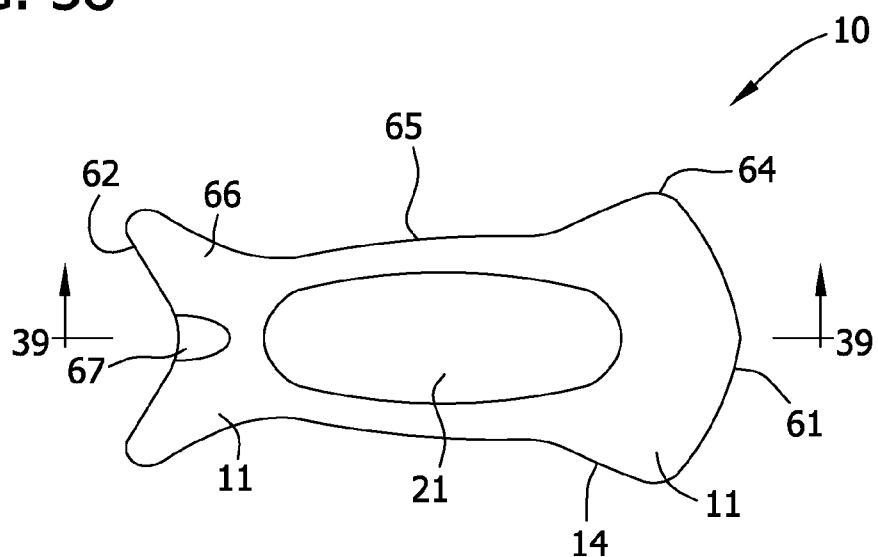
FIG. 38 shows a top view of another absorbent article of the present invention having a design for attachment to specific area of the body.

In addition, the absorbent article 10 may also be configured to have an anterior region 64, a central region 65 and a posterior region 66, as is shown in FIG. 38. A particular embodiment is shown in FIG. 34 of an absorbent article having a configuration designed to fit specific areas of the vulva region of a user. By providing specific portions for attachment to specific areas of the body of the user, the absorbent article may be configured to better fit the body of the user. The anterior region 64 of the absorbent article will be the portion of the absorbent article between the absorbent structure 21 and the first end 61 of the absorbent article 10. The posterior region 66 of the absorbent article 10 will be the portion of the absorbent article between the absorbent structure 21 and the second end 62 of the absorbent article 10. Generally, the posterior region 66 will be designed to be placed between the vagina area and the anal area of the user. The anterior region 64 is designed to be placed on the mons Veneris region of a female user. The central region 65 of the absorbent article 10 is designed to cover the vagina area of the user and the skin area surround the lateral sides of the labia majora, when the absorbent article is used as a pantiliner, sanitary napkin or an incontinence article. In an alternative use, the absorbent article of the present invention may also be used as an underwear replacement, or a guard for a swimming suit.

Figure 39:
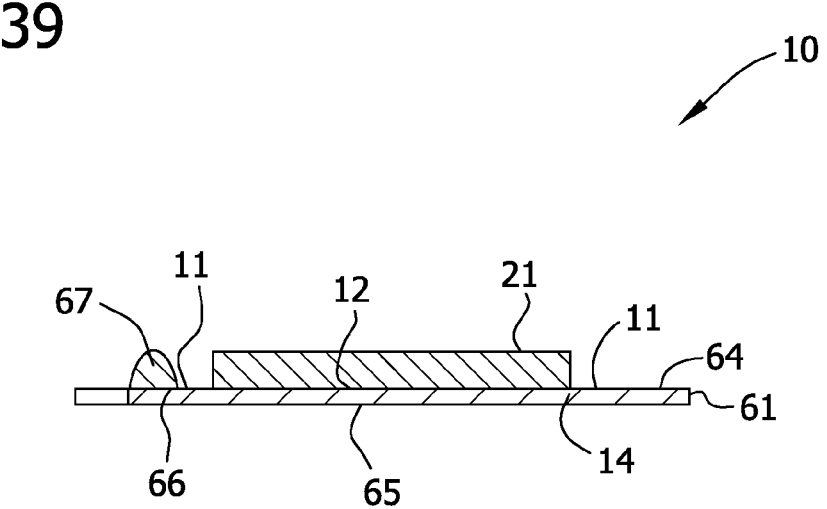
FIG. 39 shows a cross-section view taken along sectional line 39-39 of FIG. 38.

To obtain an effective attachment to the body of the user, the shell 14 can be configured to be anatomically correct for a user. As is shown in FIGS. 38 and 39, the shape of the absorbent article 10 is such that it will correctly and securely fit in the vulva region of a user. The general shape of the absorbent article shown in FIG. 39 has been found to effectively attach to the vulva region of female users of the absorbent article. Additional features may be included to ensure an anatomically correct shape. For example, in the posterior region of the absorbent article 10, more particularly, the posterior region of the shell on the first side 15, the shell 14 may be imparted with a three-dimensional protrusion 67, as shown in FIGS. 38 and 39. The protrusion 67 acts to fit comfortably in the perinea region of the user. The protrusion 67 may be formed from the shell material of may be formed from the body adhesive 44. By providing the three-dimensional protrusion 67, the absorbent article can effectively fit to the typical body shape of the female user, thereby preventing leaks form the posterior region of the absorbent article. The protrusion 67 may also serve as a guide to the user in placement of the absorbent article 10 on the body prior to use.

Figure 40:
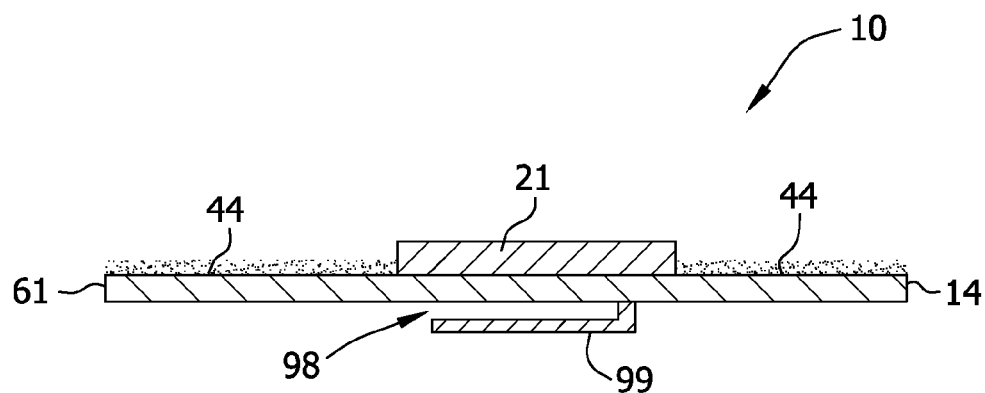
FIGS. 40 and 41 show embodiments of the present invention with placement guides.
Figure 41:
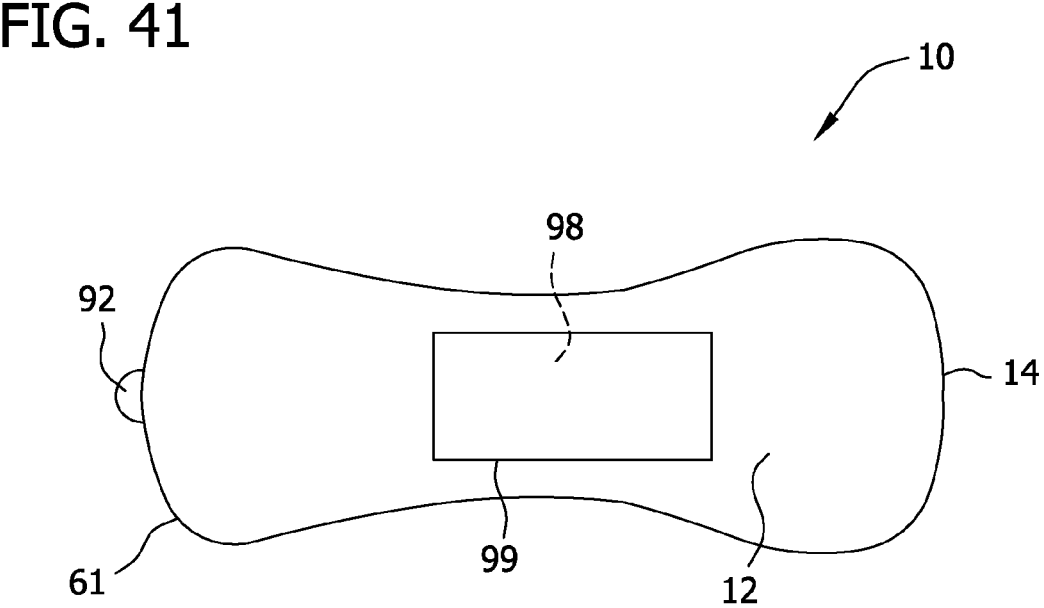

The absorbent article of the present invention may have other features which aid the user to place and remove the absorbent article from the body. As is shown in FIGS. 40 and 41, the second side 12 of the shell 14 may be provided with positioning aids, such as a finger pocket 99, or finger grooves in the shell material. The finger pocket 99 has an opening 98 toward the anterior region 64 or first end 61 of the absorbent article 10. The pocket 99 gives the user a location to place her fingers during placement of the absorbent article 10 onto the user's body. The pocket 99 may be an opening wide enough for the user to place at least two fingers in the pocket. Alternatively, there may be two or more openings which allows the user to place only one finger in each opening. Other similar positioning aids may be used to help guide a user to properly place the absorbent article for use. For example, grooves may be placed in the second side 12 of the shell 14 opposite the absorbent structure. This may allow the user to feel the location of the absorbent structure relative to the vulva region during application of the absorbent article 10 to the vulva region of the body. The pocket 99 may also assist the user in removing the absorbent article from their body.

The absorbent article 10 may also be provided with a removal aid which provides the user with an easy way to grasp and remove the absorbent article applied to the body. One particular removal aid is shown in FIG. 41 including a tab 92 located on the first end 61 of the shell which is not adhered to the body or is devoid of adhesive. Alternatively, other removal aids, such as having an area of the first end 61 being devoid of the body attaching adhesive 44. Other types of removal aid which may be present include loops, and pull strings. The removal aid allows the user to effectively begin the process of gentling removing the absorbent article from the body of the user, without the need of having to find a portion of the shell which may not be completely attached.

Other features or additives may be incorporated into the absorbent article of the present invention. For example, the absorbent article may contain an odor control agent, or a fragrance, skin wellness agents and other similar additives currently used in currently available absorbent articles. Any odor control agent or, fragrance known to those skilled in the art may be used in the absorbent article of the present invention. The odor control agent or fragrance may be added in various components of the absorbent article, including the shell 14, the absorbent structure 21 of the body adhesive 44. Skin wellness additives may be added onto the absorbent structure, any portion of the first area 15 of the shell not attached to the user or in the body adhesive 44.

Generally, to apply the absorbent article 10 to the body of a user, the release sheet 46, protecting the absorbent structure and adhesive, if present, is removed from first surface of the shell. Next, the user positions the absorbent structure of the portion of the body in which absorbency is needed. If positioning pockets or other positioning aids are present on the absorbent structure, the user may optionally use these positioning aids to properly place the absorbent article for use. In the case of sanitary napkins and incontinence absorbent articles for females, the absorbent is positioned over the vagina area such that the absorbent structure will absorb body fluids. The user then checks to ensure that the first area 11 of the shell or the adhesive 44, if present, is contacting the skin around the vagina area.

If the absorbent article is intended to have a front and a back portion, the user first identifies the anterior region 64 and/or the posterior region 66 of the absorbent article. To aid in identification of the anterior and posterior regions, indicia located on the release sheet, shell or absorbent to indicate the anterior region and/or posterior region of the absorbent article may be present. Indicia can be simply lettering or a picture to indicate the front or back of the absorbent article. Once anterior region and posterior region are identified by the user, the user places the absorbent article in the same manner described above.

In each case, the absorbent structure, which is designed to cover the labia majora of the user, may be positioned with the aid of the absorbent structure. More specifically, the absorbent structure, when sized and shaped to the approximate size of the labia majora, can serve to guide the placement of the absorbent structure over the labia majora. Once properly placed, pressure is applied by the user to the second surface of the shell which will allow the first surface of the shell to contact the skin of the user, or to allow any adhesive applied to the first surface to be applied to the skin of the user.

By having the absorbent article 10 attached to the body of a user, the absorbent article 10 will tend to move with the skin of the user. This results in a comfortable to wear absorbent article which will be less likely to leak than conventional absorbent articles. The absorbent article has a very close to the body fit which may provide improved discretion for the user.

Other benefits of the absorbent article 10 of the present invention may also be provided. For example, when the first side of the shell has an adhesive applied thereto, upon removal of the absorbent article after user, the user may fold the first side of the shell onto itself to dispose of the used absorbent article. An effective seal may be formed around the perimeter of the shell, thereby effectively encapsulating the absorbent structure within a closure. As a result, any odors associated with the absorbed fluids will be contained within the shell material.

Figure 42:
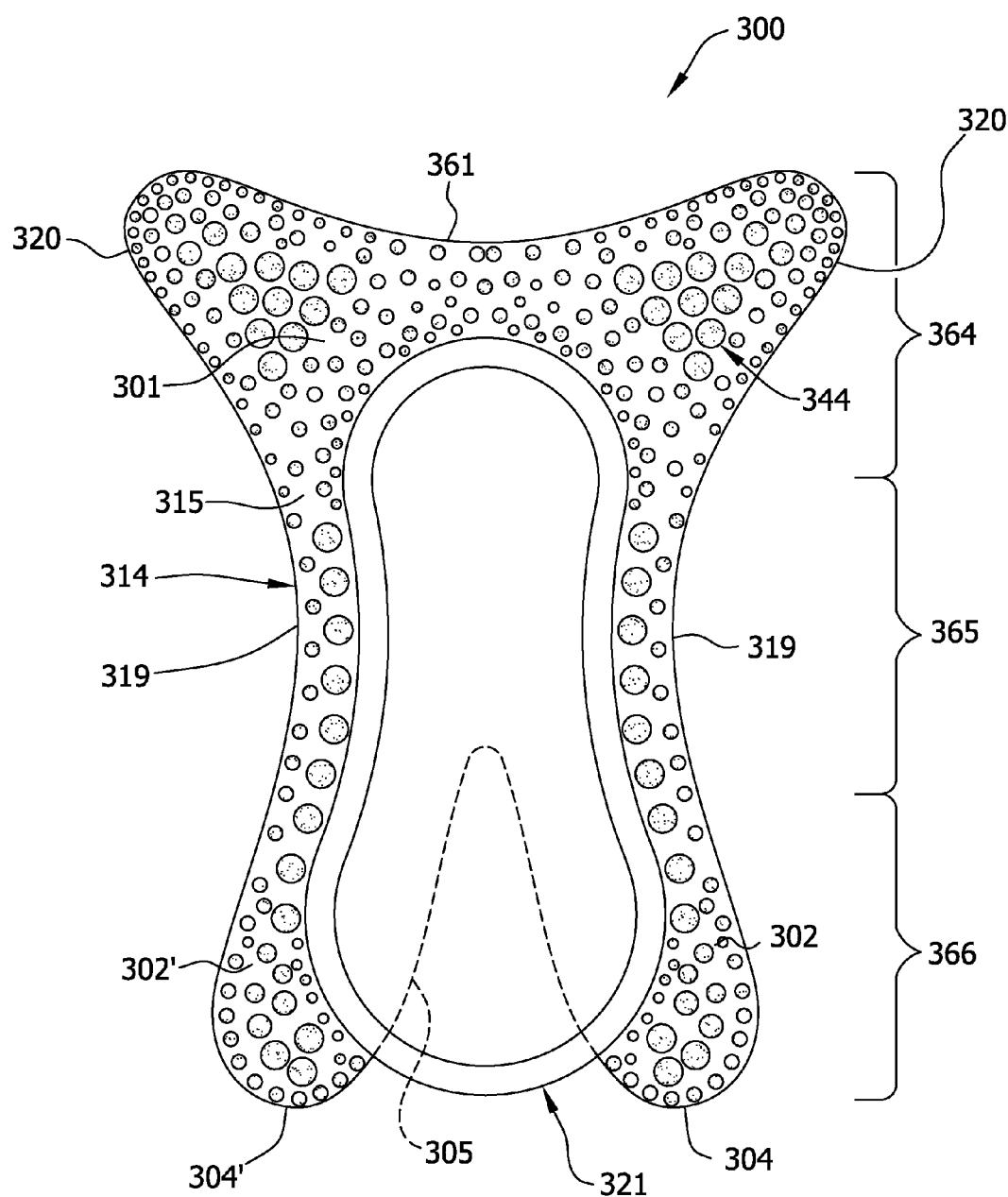
FIG. 42 shows a top view of still another embodiment of an absorbent article of the present invention, the article having an adhesive in a non-uniform pattern.

In yet another embodiment, a body adhesive absorbent article 300, which is illustrated in FIG. 42, comprises a shell 314 and an absorbent structure 321. The absorbent structure 321 is configured for disposition adjacent a female wearer's vaginal region to absorb bodily fluids discharged by the wearer. The shell 314 has a first region 301, a pair of lateral side regions 302, 302' extending from the first region, and an opening 305 extending longitudinally at least in part between the side regions. The shell 314 also has a first side 315, which defines a body-facing surface, and a second side, which defines a garment-facing surface (not shown for this embodiment but is substantially the same as the second side 217 of the body adhesive absorbent article 200 illustrated in FIG. 17).

In the illustrated embodiment, the first side 315 of the shell 314 has a body adhesive, indicated generally at 344, on at least a portion thereof for adhering the absorbent article 300 directly to the wearer's skin, and particularly, to a female wearer's skin surrounding her vulva region for the illustrated absorbent article. The body adhesive 344 contacts the skin and hair, if present, in the vulva region and possibly the pubic region and/or the perinea region of the wearer's body, thereby supporting and holding the shell 314 and absorbent structure 321 against the body of the wearer during use. A peel sheet or release sheet (not shown with respect to this embodiment) may be used to prevent the body adhesive 344 from becoming contaminated, thus losing its ability to stick to the body of the wearer and/or prematurely adhering to an unintended surface.

The size and shape of the shell 314 is selected so that the absorbent article 300 will have a comfortable feeling for the wearer and inhibit the absorbent article against becoming detached from the body of the wearer during use thereby providing protection against leaks. The absorbent article 300 (and hence the shell 314) can be suitably divided into three general longitudinal regions: an anterior region 364, a posterior region 366, and a central region 365 extending longitudinally between and interconnecting the anterior and posterior regions. Each of these regions 364, 365, 366 is sized and shaped for alignment with different body regions of a wearer of the absorbent article. More specifically, the anterior region 364 of the article 300 is adapted to be disposed adjacent the wearer's lower abdomen region. The central region 365 is adapted to be disposed between the upper thigh region of the wearer to cover the wearer's perineum region and vaginal region. The posterior region 366 of the article 300 is adapted to be disposed in the gluteal region of the wearer. In the illustrated embodiment, the anterior region 364, the central region 365, and the posterior region 366 of the absorbent article 300 are of roughly equal length, with each region corresponding generally to about ⅓ of a total length of the absorbent article 300. It is contemplated that two or all three of the article regions 364, 365, 366 may instead be of unequal lengths depending on the desired fit and the intended body placement of the article without departing from the scope of this invention.

The absorbent structure 321 is suitably adhered to the first side (i.e., body-facing surface) 315 of the shell 314 and is sized and located relative to the shell such that the shell extends both longitudinally and/or transversely outward beyond the periphery of the absorbent structure in at least the anterior region 364 and the central region 365, and more suitably in at least a portion of the posterior region 366 as well. The absorbent structure 321 is offset longitudinally, i.e., not centered lengthwise on the transverse or lateral axis of the absorbent article, such that the shell 314 extends longitudinally outward beyond the absorbent structure a greater distance in the anterior region 364 of the article 300 than in the posterior region. It is understood, though, that the absorbent structure 321 may be longitudinally centered so that the shell 314 extends equally longitudinally outward beyond the absorbent structure, or may be offset longitudinally toward the anterior region 364 so that the outward longitudinal extension of the shell beyond the absorbent structure is greater in the posterior region 365 than in the anterior region without departing from the scope of this invention.

A first end 361 of the absorbent article 300, and more particularly a longitudinal edge of the anterior region 364 defining this first end of the absorbent article 300, is suitably contoured along the width of the shell at this first end to accommodate the lower abdomen region of the wearer. In the illustrated embodiment, for example, the longitudinal extent (e.g., length) of the shell 314 relative to the transverse axis of the article is non-uniform across the width of the shell at the first end 361 of the article, and more suitably increases as the shell extends transversely outward from the longitudinal axis of the article to transversely, or laterally opposite sides 319 of the article and more particularly laterally opposite side edges of the shell. Accordingly, a greatest longitudinal extent of the shell 314 is generally adjacent the intersection of the longitudinal end 361 with the respective sides 319 of the article (i.e., the shell in the embodiment of FIG. 42). More suitably, the longitudinal edge of the shell 314 (i.e., at first end 361 of article 300 in the illustrated embodiment) is generally arcuate as it extends across the width of the shell at its longitudinal edge. The contoured longitudinal edge of the shell 314 (i.e., first end 361 of the article 300 in the illustrated embodiment) thus broadly defines a recess in the anterior region 364 of the article (and thus of the shell in this instance). It is understood, however, that the contour of the longitudinal edge of the shell 314 in the anterior region 364 of the article may be V-shaped, U-shaped or other suitable shape without departing from the scope of this invention.

The sides 319 of the illustrated article 300 are suitable defined by transversely opposite side edges 319 of the shell 314. These side edges 319 of the shell 314 are contoured so that the overall width of the article 300 (i.e., the distance between the transversely opposite sides 319 thereof), and more particularly the width of the shell in the illustrated embodiment, is non-uniform along the length of the article to define leg cutouts for accommodating the thighs of the wearer. In one suitable embodiment, the width of the article 300 and hence the shell 314 increases from a narrowest width in the central region 365 of the article toward each of the longitudinally opposite ends (361 and 304, 304') of the article. Still more suitably, the width of the article 300 and more suitably the shell 314 is also greater in the anterior region 364 of the article than in the posterior region 366. In the illustrated embodiment, for example, a greatest width of the article 300 is defined by the transverse side edges 319 of the shell 314 adjacent the longitudinal edge of the shell (e.g., first end 361 of the article 300) in the anterior region 364 of the article.

In the article 300 illustrated in FIG. 42, the sides 319 of the article 300 and more particularly the transverse side edges of the shell 314 are generally arcuate along substantially the entire length of the article. Alternatively, the sides 319 may be arcuate along only a portion of the length of the article 300. It is also understood that the sides 319 defining the leg cutouts may be V-shaped, U-shaped or other suitable shapes, or they may be uniform (e.g., straight or longitudinal) along substantially the entire length of the article 300. It is also understood that the sides 319 of the article may be contoured to define article 300 widths other than those set forth above without departing from the scope of this invention. It is further understood that the greatest width of the article 300 may be other than in the anterior region 364, and/or the narrowest width may be other than in the central region 365 of the article and remain within the scope of this invention.

Still referring to FIG. 42, the anterior region 364 of the absorbent article 300 comprises the first region 301 of the shell 314 and a portion of the absorbent structure 321. Since much of the first side (i.e., body-facing surface) 315 of the shell 314 is exposed (i.e., not covered by the absorbent structure 321) in the anterior region 364 of the absorbent article 300, a relatively large surface area of the first side of the shell is available for receiving adhesive 344 thereto for adhering the shell, and hence the absorbent article, to the wearer.

The contoured longitudinal edge of the shell 314 (e.g., first end 361 of the article 300) at the anterior region 364, together with the contoured transverse side edges of the shell (e.g., article sides 319) where these side edges generally intersect the longitudinal edge of the shell, define a pair of transversely spaced tabs 320 in the anterior region. Each of the tabs 320 suitably has body adhesive 344 on the body-facing surface (e.g., first side 315) for adhering the tabs directly to the wearer and more suitably to the abdomen region of the wearer. In one particularly suitable embodiment, the tabs 320 are sized to extend to a region of the wearer that has little or no pubic hair to facilitate better adherence to the wearer's skin.

With reference still to FIG. 42, the posterior region 366 of the absorbent article 300 includes the opening 305 in the shell 314 with portions of the lateral side regions 302, 302' broadly defining a pair of transversely spaced tabs disposed on opposite sides of the opening. The posterior region 366 disposition of these tabs is such that the tabs are aligned generally with the buttocks of the wearer rearward of the perineal region. In the illustrated embodiment, the opening 305 is in the form of a generally V-shaped ingress extending longitudinally on the longitudinal axis of the article 300 such that the tabs are free to flex relative to the central region 365 of the article and generally independent of each other to accommodate normal movement of the wearer's thighs and buttocks. It is understood that the ingress 305 can be larger or smaller without departing from some aspects of this invention.

The absorbent structure 321 is secured to the first side (i.e., body-facing surface) 315 of the shell 314, such that at least a portion of the absorbent structure covers the opening or ingress 305 in the shell. The absorbent structure 321 may be attached to the shell 314 in a permanent manner, meaning that the absorbent structure is generally intended not to be removable by the wearer of the absorbent article 300. Alternatively, it may be removably and in some embodiments refastenably) attached to the shell 314, such that the absorbent structure 321 may be removed (and in some embodiments reattached) by a wearer.

The shell 314 and absorbent structure 321 are sized relative to each other such that a portion of the shell extends outward beyond the peripheral edge of the absorbent structure along at least a portion of the peripheral edge of the absorbent structure. In this manner, a portion of the shell 314 about the periphery of the absorbent structure 321 is uncovered with the first side (i.e., body-facing surface) 315 of the shell exposed and available for adhesion to the wearer. For example, the shell 314 in one suitable embodiment extends outward beyond the peripheral edge of the absorbent structure 300 at least in the anterior region 364 and central region 365, and more suitably also in a portion of the posterior region 366.

The distance that the shell 314 extends outward beyond the peripheral edge of the absorbent structure 321 is suitably non-uniform about the periphery of the absorbent structure. More particularly, the shell 314 extends transversely outward beyond each of the side edges of the absorbent structure 321 a greater distance in the anterior region 364 than in the central region 365. It is understood, however, that shell 314 may extend a uniform distance outward of the absorbent structure 321, or may extend outward according to a different pattern than illustrated in FIG. 42, and remain within the scope of this invention.

In one suitable embodiment, as seen in FIG. 42, the body adhesive 344 covering the exposed portions of the first side 315 of the illustrated shell 314 (i.e., the portions of the shell not covered by the absorbent structure 321) has a non-uniform pattern. That is, the non-uniform pattern of body adhesive 344 can be formed with areas of greater and lesser densities of adhesive. The areas of the shell having a greater density of body adhesive 344 will adhere to the body with a greater adhesive strength than the areas with lower density. As a result, the non-uniform pattern can be configured to vary the adhesive strength (i.e., the ability of the adhesive to bond to the wearer's body), the breathability of the shell, and/or the stretchability of the shell.

The non-uniform pattern of adhesive 344 in the embodiment illustrated in FIG. 42 is selected so that the adhesive strength is greater at the tabs 320 of the anterior region 364 than in the portion of the anterior region between the tabs. In other words, the density of adhesive 344 is greater at the tabs 320 than at other portions of the anterior region 364 of the shell 314. The tabs 320 are suitable designed to extend beyond areas of the wearer's body typically covered by pubic hair whereas the portion of the anterior region 364 of the shell 314 between the tabs overlies an area of the wearer's body potentially covered by pubic hair. Thus, the adhesive strength is greater in areas with more skin surface available (i.e., no or lesser amounts of pubic hair) for adhering the article 300 to the wearer's body while reducing the adhesive strength in areas potentially covered by pubic hair or greater amounts of pubic hair to facilitate more comfortable removal of the article from the wearer.

In the illustrated embodiment, the density of adhesive and thereby the adhesive strength in the central region 365 of the shell 314 is greater adjacent the absorbent structure 321 and reduced adjacent the lateral sides 319 of the shell. This allows the shell 314 adjacent the lateral sides 319 thereof to stretch during use a greater distance than the portions of the shell adjacent the absorbent structure 321. In use, the shell 314 (if manufactured from a stretchable material) will be able to stretch between locations at which the shell is adhered to the wearer's body. Increasing the adhesive density adjacent the absorbent structure 321 in the central region 365 ensures that the absorbent structure remains in close proximately to the wearer's body during use and thereby reduces the potential for leaks. In the posterior region 366 of the shell 314, the illustrated embodiment has an area of increased adhesive density and thereby adhesive strength and is surrounded by an area of decreased adhesive density. As a result, the adhesive strength is decreased adjacent the absorbent structure 322 and the longitudinally ends 304, 304' of the shell.

In the illustrated embodiment of FIG. 42, the first side 315 of the shell 314 has a reduced density of adhesive 344 adjacent its peripheral edge thereby reducing the adhesive strength adjacent the perimeter of the article 300. This facilitates removal of the article 300 during use by allowing the wearer to more easily start the removal process. When wearer wants to peel the article 300 from her body, the wearer can manually grasp the peripheral edge of the shell 314 and a portion of the article 300 away from her body. The reduced adhesive density allows the portion of the article 300 to easily pull away from the wearer's body. This uplifted portion of the article 300 can be securely grasped by the wearer and used to peel the remaining, more adhered portions of the article from the wearer's body.

In one suitable embodiment, the shell 314 is formed from a material that is breathable, flexible, and/or stretchable. In this embodiment, the non-uniform pattern of adhesive can be used to vary the breathability and/or stretchability of the shell, which may be directly effected by the density of the adhesive. In one embodiment, the areas of the shell having lower adhesive densities are more breathable, flexible, and/or stretchable than areas having greater adhesive densities. The inverse may also be true, the areas of the shell having greater adhesive densities may be less breathable, flexible, and/or stretchable than areas having less adhesive densities. Thus, the non-uniform pattern can be used to selectively configure the breathability, flexibility, and/or stretchability of the shell.

In the embodiment illustrated in FIG. 42, the non-uniform pattern of adhesive 344 comprises discrete circular dots that vary in size and spacing. In the illustrated embodiment, the discrete dots include small, medium, and large sized dots. As a result of the body adhesive 344 being in discrete dots, a continuous area of the first side 315 of the shell 314 is free from the body adhesive. In this continuous area, the breathability, flexibility, and/or stretchability of the shell 314 can be maintained to some extent even when non-breathable, nonflexible, and/or non-stretchable adhesive 344 is used. It is understood that the dots can be other than circular and any suitable size without departing from the scope of this invention. For example, the dots can be triangular, square, diamond, or any other suitable shape or combination of shapes. It is also understood that the adhesive 344 can be applied in a continuous area that forms discrete areas of the first side 315 of the shell that are free from the adhesive. It is further understood that the adhesive 344 can be breathable, flexible, and/or stretchable.

In the illustrated embodiment, the varying sizes of the discrete dots and the varying spacing between the discrete dots provide a visual cue to the wearer that the density of the body adhesive 344 is varied in different portions of the first side 315 of the shell 314. These visual cues can convey to the wearer that the absorbent article 300 has sufficient adhesive strength to remain on the wearer's body during use while not being painful to remove, especially in more sensitive regions of the female body such as those covered with pubic hair or have a greater density of pubic hair. The visual cues may also convey to the wearer that the shell 314, while bonded to the wearer, remains breathable during use and even has a greater degree of breathability in selected areas. Also, the visual cue may indicate to the wearer that the shell 314 remains flexible and/or stretchable even while bonded to the wearer's body.

For example, larger adhesive dots of adhesive 344 or the adhesive being applied in geometries with increased surface coverage and/or less spacing between geometries or shapes will covey to the wearer the perception of increased attachment/bonding. More open space between the dots (or any other shape) of adhesive 344 or geometries will increase the perception of breathability to the wearer. Smaller dots of adhesive 344 or having more open space between the dots of adhesive in areas of the article 300 adapted to cover more sensitive regions of the female body will convey the perception of more comfortable attachment during use and release during removal. In one suitable embodiment, the visual cue has areas of open space resulting from smaller discrete dots and/or greater spacing between the dots of adhesive 344 for conveying to the wearer that the shell 314 remains flexible and/or stretchable even while bonded to the wearer's body.

In one suitable embodiment, the adhesive 344 can have different formulations in different areas of the shell 314. For example, the adhesive 344 can have a first formulation with a first adhesive strength in one or more areas of the shell 314 and a second formulation with a second adhesive strength that is less than the first adhesive strength in one or more other areas of the shell. The first formulation can be used in areas of the shell 314 were greater adhesive strength may be desired, such as areas where more stress is applied to the adhesive due to movement of the wearer. The second formulation, which has the lower adhesive strength, may be used in areas of the shell where less adhesive strength may be desired, such as in more sensitive areas of the female body.

The adhesive strength of the adhesive 344 can also be varied in different areas of the shell 314 by varying the thickness of the adhesive. In one embodiment, thicker adhesive 344 results in greater adhesive strength of the adhesive. In another suitable embodiment, the thickness of the adhesive 344 can be greater in areas adapted to cover regions of the female body covered by pubic hair. This facilitates the adhesive 344 penetrating the pubic hairs of the wearer and adhering to the wearer's skin beneath the hair. The thickness of the adhesive 344 can be thinner in areas adapted to cover regions of the wearer free from pubic hair or areas having lesser pubic hair densities. In this embodiment, the adhesive strength may be substantially the same or different in the different areas of the shell. In one suitable embodiment, the adhesive strength is less in areas of the shell 314 adapted to cover regions of the female body covered by pubic hair than in areas of the shell adapted to cover regions of the female body with less or no pubic hair.

Other suitable visual cues may be provided instead of or in addition to the variance in size and spacing of discrete dots of adhesive. For example, a colored adhesive can be used to provide a visual cue to the wearer that the density of adhesive 344 varies in different areas of the shell 314. The adhesive can be a single color or the color can vary in different areas corresponding to the different adhesive densities. Color can be described generally in terms of three elements, hue, chroma (or saturation) and lightness (sometimes called value or brightness). As used herein, varying or changing the color of the adhesive comprises changing at least one of hue, chroma or lightness. In one suitable embodiment, the adhesive 344 has a first color in one or more areas of the shell 314 indicating that the adhesive in these areas has a first adhesive strength and a second color in one or more different areas of the shell indicating that these areas have a second adhesive strength that is less than the first adhesive strength. The color can be added to the adhesive 344, printed on the adhesive, or printed on the shell 314 beneath the adhesive. It is also contemplated that color can be printed on the first side 315 of the shell 314 in areas free of adhesive instead of or in addition to providing color to the adhesive.

In one suitable embodiment, the adhesive 344 comprises an acrylate-based adhesive and an adhesion modifier but it is understood that any suitable adhesive can be used (e.g., a silicone-based adhesive). It has been found that the adhesion modifier can allow the adhesive to have a greater bonding strength with a substrate, yet remain gentle on the skin's surface. In one embodiment, the skin-adhesive composition can further include at least one skin benefit agent for providing improved skin health to the user. The acrylate-based adhesive may be any acrylate-based adhesive known in the art, provided that the adhesive is not a known irritant to human skin or that the adhesive is so aggressive that it causes pain to the user/wearer when the absorbent article 300 is removed from the skin. It is also desirable that the adhesive is selected such that the adhesive does not leave a substantial amount of adhesive residue on the surface of the skin of the wearer when the absorbent article 300 is removed by the wearer after use.

Suitable acrylate-based adhesive can typically be made from acrylate copolymers and tackifiers as known in the art. For example, typical acrylate-based adhesives include an alkyl acrylate, preferably a monofunctional unsaturated acrylate ester of a non-tertiary alkyl alcohol, wherein the alkyl group contains 1 to about 14 carbon atoms. Included within this class of monomers are, for example, isooctyl acrylate, isononyl acrylate, 2-ethylhexyl acrylate, decyl acrylate, dodecyl acrylate, n-butyl acrylate, and hexyl acrylate. In one embodiment, the acrylate-based adhesive includes acrylate-based pressure sensitive adhesives including acrylate monomers such as isooctyl acrylate, isononyl acrylate, and butyl acrylate. In another embodiment, the acrylate-based adhesives include polyacrylate hot-melt adhesives, such as the polyacrylate hot-melt adhesive, commercially available as NS 34-546B from Henkel International.

Suitable adhesion modifiers include, for example, colloidal particles, crosslinked acrylate copolymers, and combinations thereof. More particularly, colloidal particles well suited for use in the present disclosure include microcrystalline cellulose, fumed silica, silica, hydrated silica, and combinations thereof. Commercially available colloidal particles such as fumed silica (available as Cab-o-sil M5 from Cabot Corporation, Tuscola, Ill.) and blends of microcrystalline cellulose and cellulose gum (available as Avicel® 591 from FMC Corporation, Philadelphia, Pa.) are particularly suitable for use as adhesion modifiers.

In one suitable embodiment, the adhesion modifier may include polymer-like network or matrix structure, such as cross-linked acrylate crosspolymers. Cross-linked acrylate crosspolymers well-suited for use in the present disclosure include allyl methacrylates crosspolymer, allyl methacrylate/glycol dimethacrylate crosspolymer, lauryl methacrylate/glycol dimethacrylate crosspolymer and derivatives thereof. Suitable examples include Poly-Pore® E-200, Poly-Pore® L-200, Polytrap® 7603 and Polytrap® 6603 Adsorber which are all available from Amcol Health & Beauty Solutions (Arlington, Ill.). The Poly-Pore® and Polytrap® ingredients can be loaded with skin beneficial ingredients prior to inclusion in the skin-adhesive combination or are available pre-loaded from Amcol Health & Beauty Solutions as Polytrap® 6035 Cyclomethicone, Polytrap® 7100 Dimethicone Macrobeads, Polytrap® 6500 Dimethicone/Petrolatum Powder, Polytrap® 665TO (which is loaded with tocopherol), and Polytrap® 6038 Mineral Oil Macrobeads.

In one particularly suitable embodiment, both the shell 314 and the adhesive 344 applied to the shell are breathable. That is, they allow air to pass through. The adhesive 344 can be made breathable by the method in which the adhesive 344 is applied to the shell 314 or by adding suitable additives (e.g., foam) to the adhesive to render it breathable. Suitable methods for rendering the adhesive 344 breathable include melt-spraying and printing the adhesive 344 unto the shell 314. Melt-spraying and printing are known methods of applying adhesive to a substrate (e.g., the shell 314). It is also understood that in some embodiments, the adhesive 344 may not be breathable. In these embodiments, the adhesive 344 can be applied to the shell 314 using a suitable slot-coating method.

Figure 43:
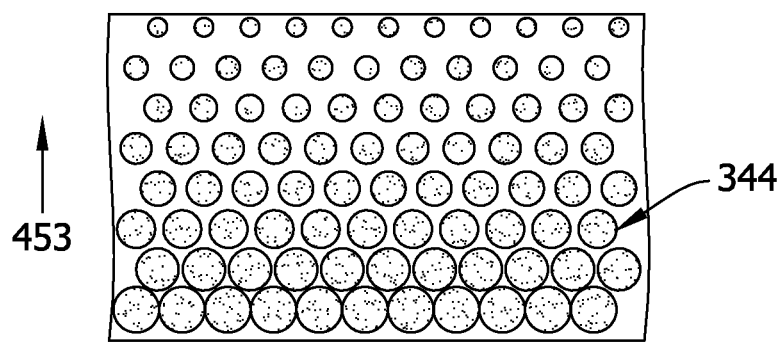
FIG. 43 shows one embodiment of a non-uniform pattern suitable for the adhesive of the absorbent article of FIG. 42.
Figure 44:
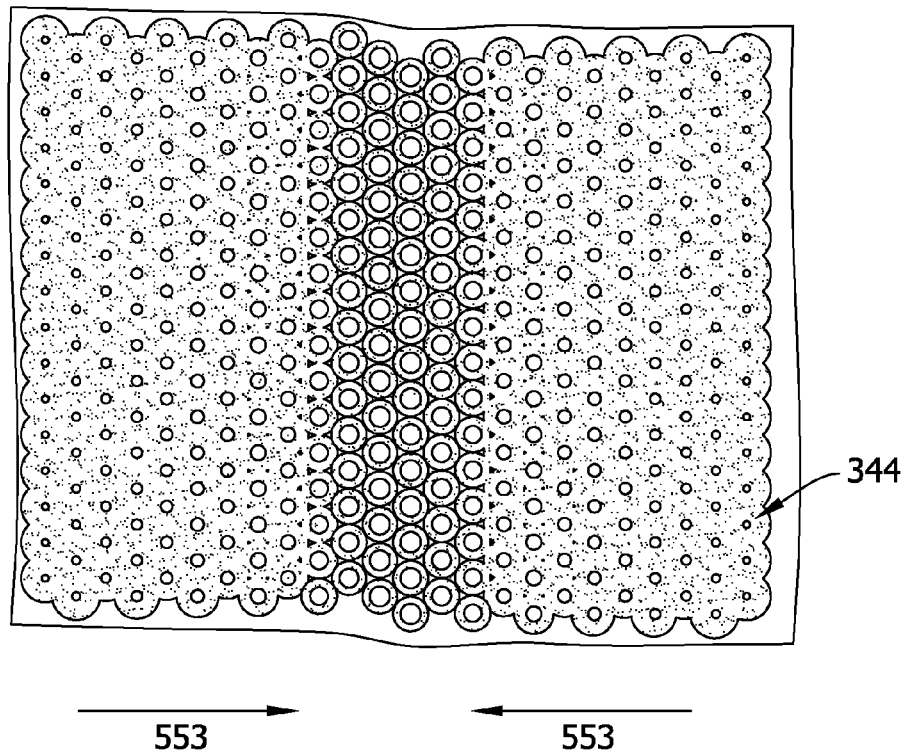
FIG. 44 shows another embodiment of a non-uniform pattern suitable for the adhesive of the absorbent article of FIG. 42.
Figure 45:
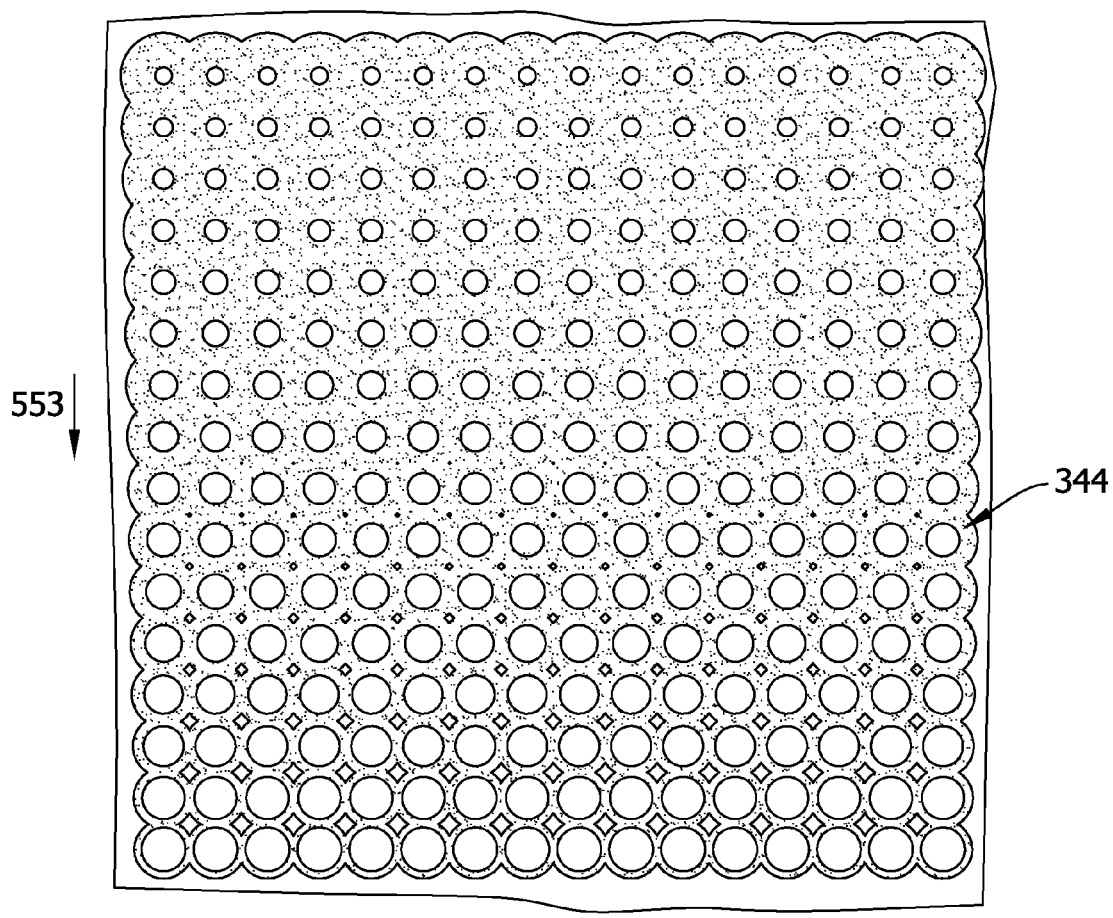
FIG. 45 shows yet another embodiment of a non-uniform pattern suitable for the adhesive of the absorbent article of FIG. 42.

FIGS. 43-45 illustrate exemplary embodiments of non-uniform patterns of body adhesive 344. In FIG. 43, the non-uniform pattern of adhesive 344 represents the pattern shown in FIG. 42 wherein the non-uniform pattern comprise a plurality of discrete circular dots that vary in spacing and size. The density of the adhesive 344 decreases in the direction of the arrow 453 seen in FIG. 43, which is upward as viewed. FIGS. 44 and 45 illustrate a non-uniform pattern comprising a continuous adhesive 344 that defines a plurality of discrete areas that are not covered by the adhesive. Arrows 553 provided in FIG. 44 indicate the directions in which the adhesive 344 decreases in density from higher density areas to a lower density area. In the embodiment illustrated in FIG. 44, the adhesive 344 in higher density areas define small, generally circular discrete areas of exposed shell (i.e., not covered by adhesive). The adhesive 344 in lower density areas define larger circular discrete areas and relatively small triangular discrete areas of exposed shell. FIG. 45 illustrates a continuous non-uniform pattern of adhesive 344 similar to that shown in FIG. 44 except that in a lower density area the exposed areas of shell comprise larger circular discrete areas and relatively small diamond shaped areas. It is understood that the discrete areas of exposed shell can be other shapes and sizes without departing from the scope of this invention.

Figure 46:
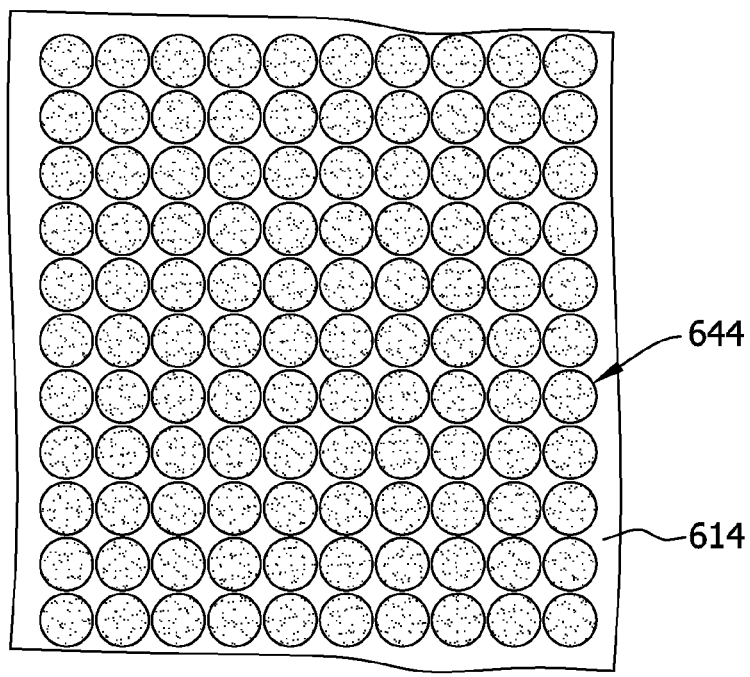
FIG. 46 shows an embodiment of a uniform pattern suitable for the adhesive of the absorbent article of FIG. 42.
Figure 47:
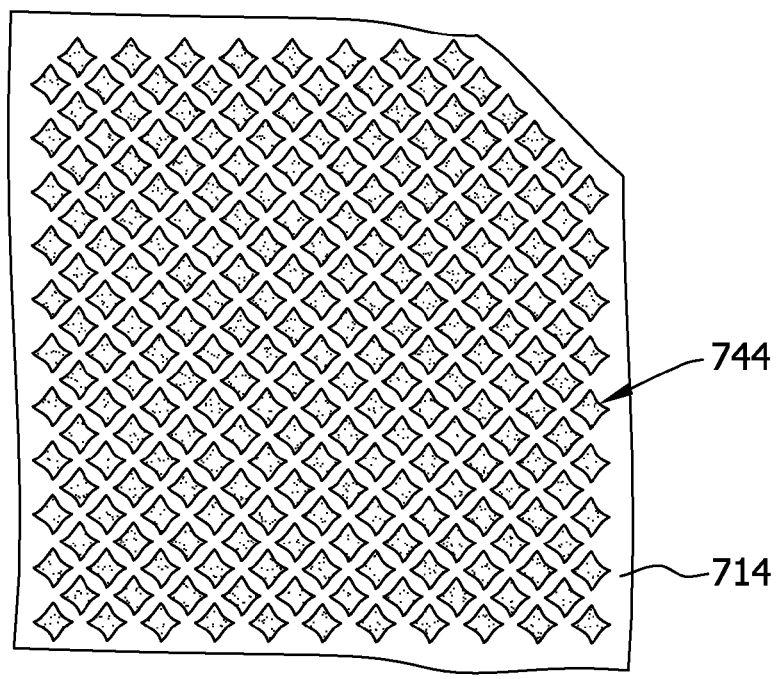
FIG. 47 shows another embodiment of a uniform pattern suitable for the adhesive of the absorbent article of FIG. 42.

FIGS. 46 and 47 illustrate suitable adhesive patterns having a uniform pattern that can be used on the shell 314. FIG. 46, for example, illustrates a patterned adhesive 644 being applied to a substrate 614. The adhesive 644 comprises a plurality of discrete circular dots having substantially the same size and with uniform spacing between the dots. FIG. 47 illustrates a patterned adhesive 744 applied to a substrate 714 and having a plurality of discrete diamond shaped dots having substantially the same size and with uniform spacing between the dots. It is understood that the adhesive can be applied in different uniform or non-uniform patterns (e.g., strips of adhesive) and the dots in the illustrated embodiments can have different shapes and sizes. In some embodiments having a uniform pattern adhesive, the density and/or the adhesive strength of the adhesive would generally be uniform throughout the exposed surface of the shell 314. In other embodiments having a uniform pattern adhesive, the adhesive density and/or strength can be non-uniform in specific areas or throughout the exposed surface of the shell 314, such as by varying the adhesive formulation or the adhesive thickness.

Figure 48:
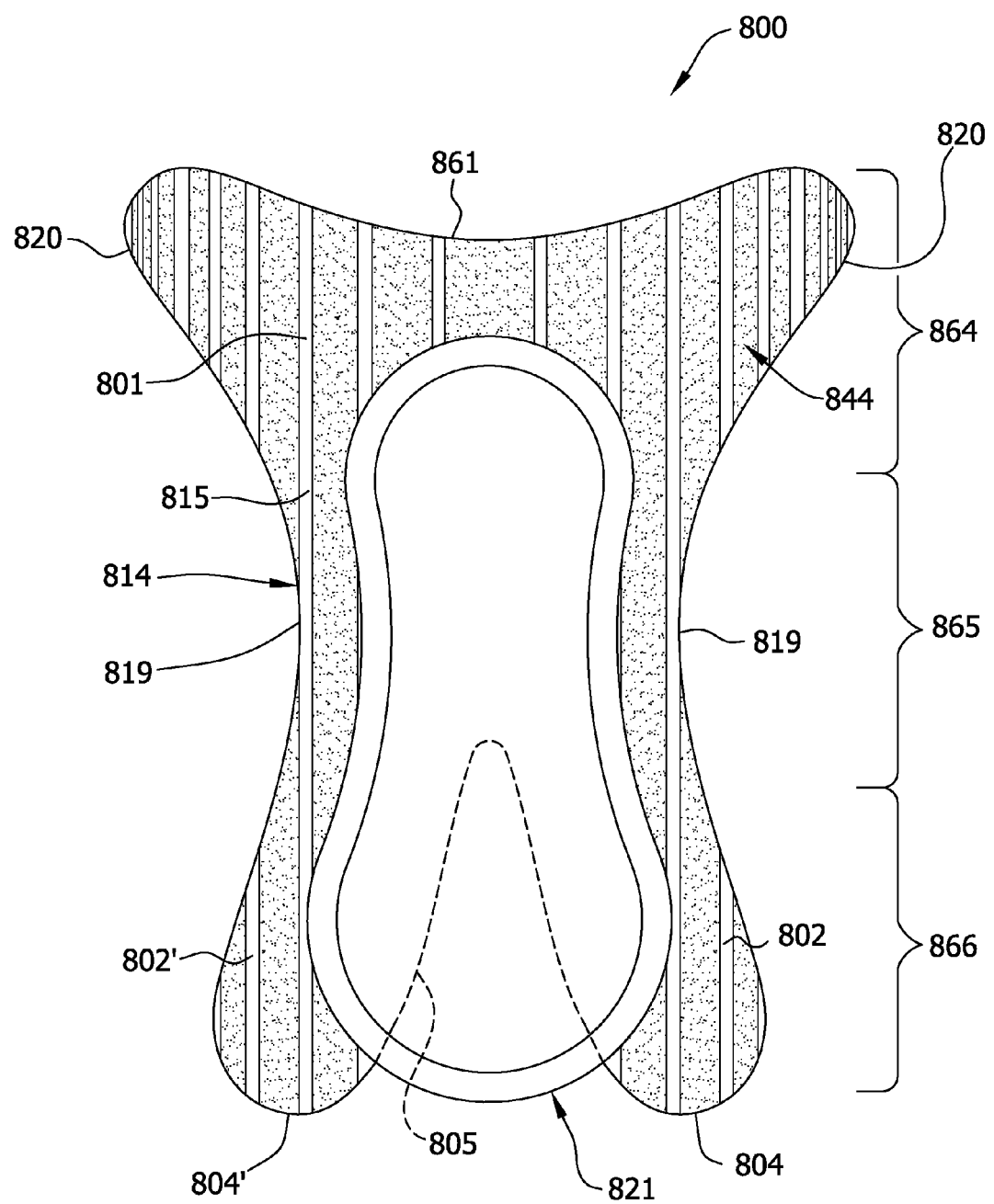
FIG. 48 shows a top view of another embodiment of an absorbent article of the present invention, the article having an adhesive in a non-uniform pattern.
Figure 49:
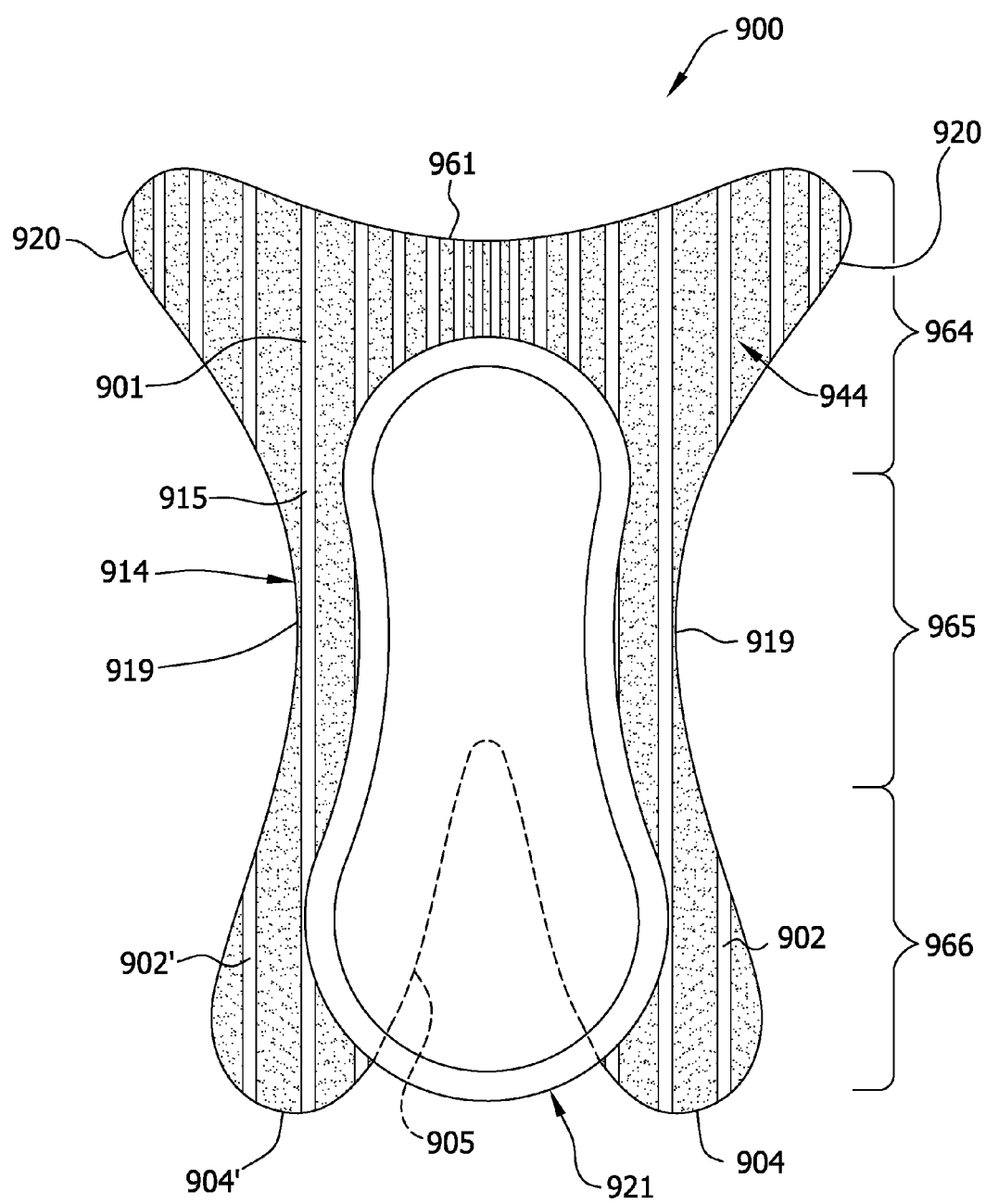
FIG. 49 shows a top view of yet another embodiment of an absorbent article of the present invention, the article having an adhesive in a non-uniform pattern.
Figure 50:
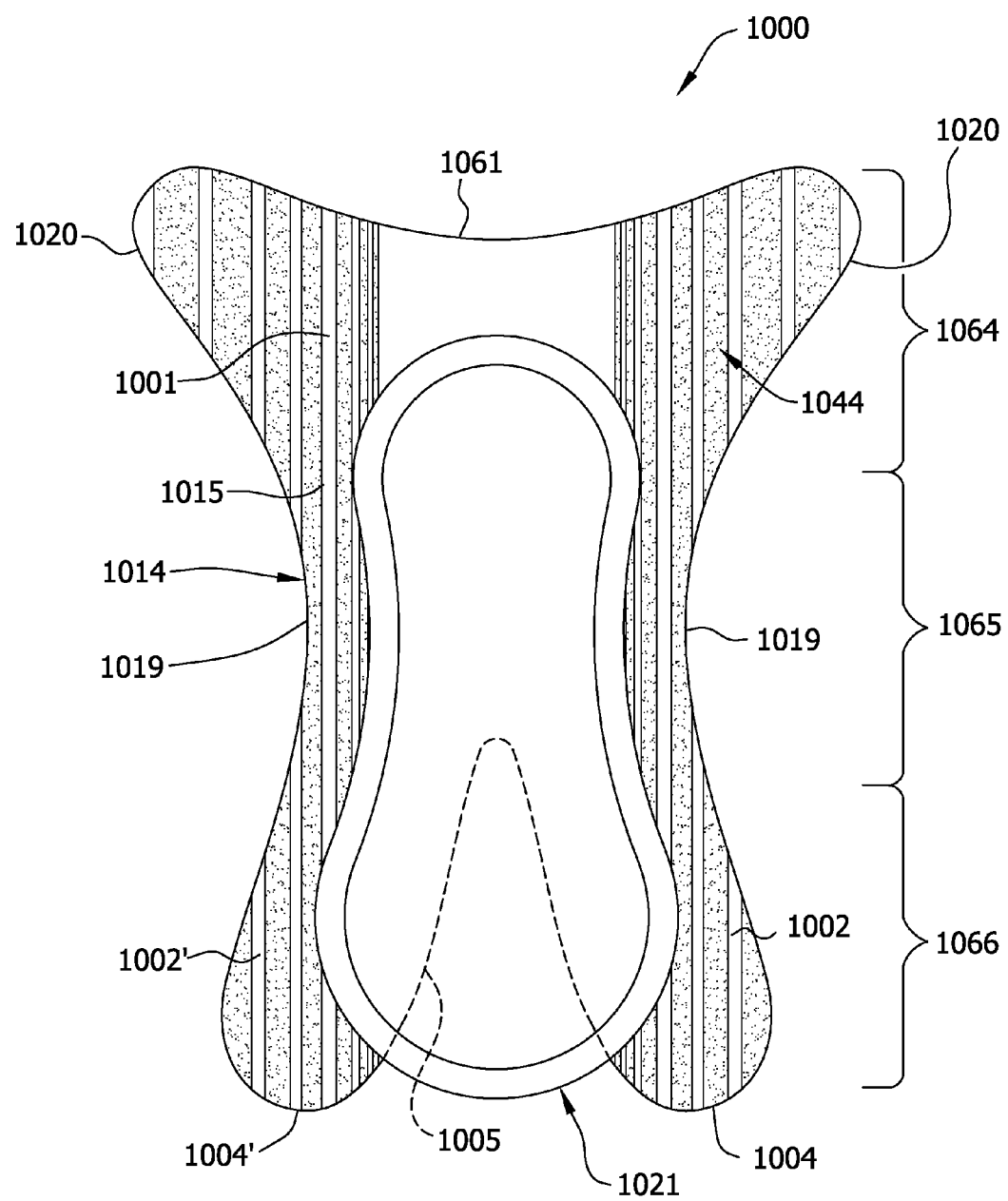
FIG. 50 shows a top view of still another embodiment of an absorbent article of the present invention, the article having an adhesive in a non-uniform pattern.

FIGS. 48-50 illustrate different embodiments of absorbent articles having non-uniform adhesive patterns in the form of strips. In FIG. 48, for example, an adhesive 844 is placed on a shell 814 of an article 800 in the form of strips that have varying widths. The widths of the discrete strips of adhesive 844 increase toward the longitudinal axis of the article 800. In other words, the strip of adhesive 844 generally aligned with the longitudinal axis of the article 800 has the greater width and the widths of the stripes decrease as they approach the lateral sides 819 of the shell 814. In this embodiment, the adhesive strength is greatest in the areas corresponding to the widest stripes of adhesive 844 and decreases in the areas having narrower stripes. The flexibility, stretchability, and breathability of the shell 814 are greater in the areas having narrower stripes than in the areas having wider stripes.

In FIG. 49, an adhesive 944 is applied to a shell 914 of an article 900 in the form of stripes having varying widths. In this embodiment, the widths of the discrete strips of adhesive 944 are greatest generally adjacent the side edges of an absorbent structure 921 of the article and are narrower generally along the longitudinal axis of the article 900 and adjacent each of lateral sides 919 of the shell 914. In this embodiment, the adhesive strength is greatest in the areas corresponding to the widest stripes of adhesive 944 and decreases in the areas having narrowing stripes. The flexibility, stretchability, and breathability of the shell 914 are greater in the areas having narrower stripes than in the areas having wider stripes.

FIG. 50 illustrates an adhesive 1044 is applied to a shell 1014 of an article 1000 in the form of stripes having varying widths. In this embodiment, the widths of the discrete stripes of adhesive 1044 are greatest generally adjacent lateral sides 1019 of the shell 1014 of the article 900. The widths of the stripes of adhesive 1044 are narrower as they approach the side edges of an absorbent structure 1021 of the article 1000. In this embodiment, an area of the shell 1014 corresponding to the longitudinal axis of the article 1000 and the adjacent surrounding areas are free from adhesive 1044 but it is understood that these areas can be coated with adhesive. In this embodiment, the adhesive strength is greatest in the areas corresponding to the widest stripes of adhesive 1044 and decreases in the areas having narrower stripes. The flexibility, stretchability, and breathability of the shell 1014 are greater in the areas having narrower stripes than in the areas having wider stripes.

Although the present invention has been described with reference to various embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A feminine care absorbent article comprising:
    an absorbent structure configured for disposition adjacent a female wearer's vaginal region to absorb bodily fluids discharged by the wearer; and
    a shell for supporting the absorbent structure at said vaginal region such that the absorbent structure does not enter the female wearer's labia majora, the shell having a body-facing surface and a garment-facing surface, the absorbent structure being attached to the body-facing surface of the shell such that the absorbent structure overlies the shell, the body-facing surface having an adhesive outboard of the absorbent structure for adhering the shell directly to the wearer's body, the adhesive being applied in a non-uniform adhesive pattern to a first area of the body-facing surface to provide a first adhesive strength, said adhesive being applied in a non-uniform adhesive pattern to a second area of the body-facing surface to provide a second adhesive strength that is less than the first adhesive strength at said first area, the shell defining an opening, the absorbent structure at least partially covering the opening.

2. The feminine care absorbent article set forth in claim 1 wherein the adhesive in the first area of the body-facing surface of the shell has a different thickness than the adhesive in the second area of the body-facing surface.

3. The feminine care absorbent article set forth in claim 2 wherein the second area of the body-facing surface is adapted to overlie a portion of at least one of the mons pubis and the labial cleft of the wearer's body, the thickness of the adhesive in the second area being greater than the thickness of the adhesive in the first area.

4. The feminine care absorbent article set forth in claim 1 wherein the adhesive is applied in a non-uniform adhesive pattern to the body-facing surface in stripes, with stripes in the first area of the body-facing surface having a width that is different than the width of stripes in the second area of the body-facing surface.

5. The feminine care absorbent article set forth in claim 1 wherein the first area of the body-facing surface of the shell is spaced from the absorbent structure.

6. The feminine care absorbent article set forth in claim 5 wherein the second area of the body-facing surface is adjacent to the absorbent structure.

7. The feminine care absorbent article set forth in claim 1 wherein the first area of the body-facing surface of the shell is adjacent to the absorbent structure.

8. The feminine care absorbent article set forth in claim 7 wherein the second area of the body-facing surface is spaced from the absorbent structure.

9. The feminine care absorbent article set forth in claim 1 wherein the absorbent article is selected from a group consisting of a pantiliner, a sanitary napkin, and an incontinence article.

10. A feminine care absorbent article comprising:
an absorbent structure configured for disposition adjacent a female wearer's vaginal region to absorb bodily fluids discharged by the wearer, the absorbent structure having a first length; and
a shell for supporting the absorbent structure at said vaginal region, the shell having a body-facing surface, a garment-facing surface, and an opening defined through the body-facing surface and the garment-facing surface, the body-facing surface having a first region and a second region, the first region having an adhesive applied in a non-uniform adhesive pattern with a first formulation and the second region having an adhesive applied in a non-uniform adhesive pattern with a second formulation that is different than the first formulation, the shell having a second length, the second length being in the range of about 170 mm to about 220 mm, the ratio of the second length to the first length being in the range of about 3 to about 1, the adhesive extending the entire second length, the absorbent structure being attached to the shell to close the opening.

11. The feminine care absorbent article of claim 10 wherein the adhesive with the first formulation has a first adhesive strength and the adhesive with the second formulation has a second adhesive strength that is less than the first adhesive strength.

12. The feminine care absorbent article of claim 10 wherein the adhesive with the first formulation has a different thickness than the adhesive with the second formulation.

13. The feminine care absorbent article of claim 12, wherein the thickness of the adhesive with the first formulation is greater than the thickness of the adhesive with the second formulation.

14. The feminine care absorbent article of claim 10, wherein the first region of the body-facing surface is adapted to overlie a portion of at least one of the mons pubis and the labial cleft of the wearer's body.

15. The feminine care absorbent article of claim 10, wherein the adhesive with the first formulation is applied to the body-facing surface in stripes and the adhesive with the second formulation is applied to the body-facing surface in stripes, with the stripes in the first region of the body-facing surface having a width that is different than the width of the stripes in the second region of the body-facing surface.

16. The feminine care absorbent article of claim 10, wherein the first region of the body-facing surface of the shell is spaced from the absorbent structure.

17. The feminine care absorbent article of claim 16, wherein the second region of the body-facing surface is adjacent to the absorbent structure.

18. The feminine care absorbent article of claim 10, wherein the first region of the body-facing surface of the shell is adjacent to the absorbent structure.

19. The feminine care absorbent article of claim 18, wherein the second region of the body-facing surface is spaced from the absorbent structure.

20. The feminine care absorbent article of claim 10, wherein the absorbent article is selected from the group consisting of a pantiliner, a sanitary napkin, and an incontinence article.

* * * * *